United States Patent
Zhang et al.

(10) Patent No.: US 8,466,339 B2
(45) Date of Patent: Jun. 18, 2013

(54) MIG-6 KNOCKOUT MICE AND ELUCIDATION OF ASSOCIATION OF MIG-6 WITH EARLY ONSET DEGENERATIVE JOINT DISEASE AND ROLE AS A TUMOR SUPPRESSOR

(75) Inventors: Yu-Wen Zhang, Grand Rapids, MI (US); George F. Vande Woude, Ada, MI (US)

(73) Assignee: Van Andel Research Institute, Grand Rapids, MI (US)

( * ) Notice: Subject to any disclaimer, the term of this patent is extended or adjusted under 35 U.S.C. 154(b) by 903 days.

(21) Appl. No.: 11/917,557

(22) PCT Filed: Jun. 15, 2006

(86) PCT No.: PCT/US2006/023257
§ 371 (c)(1),
(2), (4) Date: Dec. 27, 2010

(87) PCT Pub. No.: WO2006/138430
PCT Pub. Date: Dec. 28, 2006

(65) Prior Publication Data
US 2011/0099644 A1    Apr. 28, 2011

Related U.S. Application Data

(60) Provisional application No. 60/690,493, filed on Jun. 15, 2005, provisional application No. 60/789,612, filed on Apr. 6, 2006.

(51) Int. Cl.
*A01K 67/027* (2006.01)
*A01K 67/00* (2006.01)
*A01K 67/033* (2006.01)
*G01N 33/00* (2006.01)

(52) U.S. Cl.
USPC ............... 800/18; 800/3; 800/10; 800/25

(58) Field of Classification Search
None
See application file for complete search history.

(56) References Cited

U.S. PATENT DOCUMENTS

| | | | |
|---|---|---|---|
| 6,194,633 B1 * | 2/2001 | Koretzky et al. | 800/18 |
| 2003/0207840 A1 * | 11/2003 | Riggins et al. | 514/44 |
| 2004/0045043 A1 | 3/2004 | Finney et al. | |
| 2004/0241851 A1 | 12/2004 | Askew et al. | |
| 2006/0064769 A1 | 3/2006 | Jones et al. | |

FOREIGN PATENT DOCUMENTS

| | | |
|---|---|---|
| EP | 1 236 474 A | 9/2002 |
| EP | 1 466 974 A1 * | 10/2004 |
| WO | 03/010205 A | 2/2003 |

OTHER PUBLICATIONS

Hackel et al. Biol Chem. Dec. 2001;382(12):1649-62.*
Wong RW, Cell Mol Life Sci. Jan. 2003;60(1):113-8.*
Ferby, Ingvar et al: "Mig6 is a negative regulator of EGF receptor-mediated skin morphogenesis and tumor formation" Nature Magazine, vol. 12, No. 5, May 2006, pp. 568-573, XP002423443.
Kwak I et al: "Genetically Engineered Mouse Models for Lung Cancer" Annual Review of Physiology, Annual Reviews, Inc. Palo Alto, CA, US, vol. 66, 2004, pp. 647-663, XP009079601.
Mateescu R G et al: "Increased MIG-6 mRNA transcripts in osteoarthritic cartilage" Biochemical and Biophysical Research Communications, Academic Press Inc. Orlando, FL, US, vol. 332, No. 2, May 5, 2005, pp. 482-486 XP004902502.
Xu Dazhong et al: "Gene 33 is an endogenous inhibitor of epidermal growth factor (EGF) receptor signaling and mediates dexamethasone-induced suppression of EFG function." The Journal of Biological Chemistry Jan. 28, 2005, vol. 280, No. 4, Jan. 28, 2005, pp. 2924-2933, XP002423444.
Zhang Yu-Wen et al: "Targeted disruption of Mig-6 in the mouse genome leads to early onset degenerative joint disease." Proceedings of the National Academy of Sciences of the United States of America Aug. 16, 2005, vol. 102, No. 33, Aug. 16, 2005, pp. 11740-11745, XP002423442.
Aigner, T. and J. Dudhia, Genomics of osteoarthritis. Curr Opin Rheumatol, 2003. 15(5): p. 634-40.
Allen, J.B., et al., Rapid onset synovial inflammation and hyperplasia induced by transforming growth factor beta. J Exp Med, 1990. 171(1): p. 231-47.
Amatschek, S., et al., Tissue-wide expression profiling using cDNA subtraction and microarrays to identify tumor-specific genes. Cancer Res, 2004. 64(3): p. 844-56.
Anastasi, S., et al., Feedback inhibition by RALT controls signal output by the ErbB network. Oncogene, 2003. 22(27): p. 4221-34.
Anastasi, S., et al., Loss of RALT/MIG-6 expression in ERBB2-amplified breast carcinomas enhances ErbB-2 oncogenic potency and favors resistance to Herceptin. Oncogene, 2005. 24(28): p. 4540-8.

(Continued)

*Primary Examiner* — Doug Schultz
(74) *Attorney, Agent, or Firm* — Honigman Miller Schwartz and Cohn LLP; Douglas H. Siegel

(57) ABSTRACT

Disruption of mitogen inducible gene 6 (Mig-6) in mice by homologous recombination (KO mice) led to early onset osteoarthritis (OA) as revealed by simultaneous enlargement and deformity of multiple joints, degradation of articular cartilage and the development of bony outgrowths or osteophytes within the joint space. Because of the striking similarity to human OA, Mig-6 KO mice are a useful animal model for studying the mechanism of this disease and for testing new drugs or therapies for treating OA. These KO mice also developed epithelial hyperplasia, adenoma, and adenocarcinoma in organs such as lung, gallbladder, and bile duct. Mig-6 is therefore a tumor suppressor gene and is a candidate gene for the frequent 1p36 genetic alterations found in lung cancer. It can be used as a tumor biomarker as well as a target for cancer therapy.

23 Claims, 16 Drawing Sheets

OTHER PUBLICATIONS

Bakker, A.C., et al., Overexpression of active TGF-beta-1 in the murine knee joint: evidence for synovial-layer-dependent chondro-osteophyte formation. Osteoarthritis Cartilage, 2001. 9(2): p. 128-36.

Beck, E., et al., Nucleotide sequence and exact localization of the neomycin phosphotransferase gene from transposon Tn5. Gene, 1982. 19(3): p. 327-36.

Benhar, M., D. Engelberg, and A. Levitzki, ROS, stress-activated kinases and stress signaling in cancer. EMBO Rep, 2002. 3(5): p. 420-5.

Berton, T.R., et al., Characterization of an inducible, epidermal-specific knockout system: differential expression of lacZ in different Cre reporter mouse strains. Genesis, 2000. 26(2): p. 160-1.

Birchmeier, C., et al., Met, metastasis, motility and more. Nat Rev Mol Cell Biol, 2003. 4(12): p. 915-25.

Bradley, A. and E. Robertson, Embryo-derived stem cells: a tool for elucidating the developmental genetics of the mouse. Curr Top Dev Biol, 1986. 20: p. 357-71.

Cancedda, R., F. Descalzi Cancedda, and P. Castagnola, Chondrocyte differentiation. Int Rev Cytol, 1995. 159: p. 265-358.

Carter, D.R., et al., The mechanobiology of articular cartilage development and degeneration. Clin Orthop Relat Res, 2004(427 Suppl): p. S69-77.

Colbere-Garapin, F., et al., A new dominant hybrid selective marker for higher eukaryotic cells. J Mol Biol, 1981. 150(1): p. 1-14.

Corazza, N., et al., Nonlymphocyte-derived tumor necrosis factor is required for induction of colitis in recombination activating gene (RAG)2(-/-) mice upon transfer of CD4(+)CD45RB(hi) T cells. J Exp Med, 1999. 190(10): p. 1479-92.

Davis, R.J., Signal transduction by the JNK group of MAP kinases. Cell, 2000. 103(2): p. 239-52.

Dragatsis, I. and S. Zeitlin, CaMKIIalpha-Cre transgene expression and recombination patterns in the mouse brain. Genesis, 2000. 26(2): p. 133-5.

Dymecki, S.M., Flp recombinase promotes site-specific DNA recombination in embryonic stem cells and transgenic mice. Proc Natl Acad Sci U S A, 1996. 93(12): p. 6191-6.

Enquist, L.W., et al., Construction and characterization of a recombinant plasmid encoding the gene for the thymidine kinase of Herpes simplex type 1 virus. Gene, 1979. 7(3-4): p. 335-42.

Fiorentino, L., et al., Inhibition of ErbB-2 mitogenic and transforming activity by RALT, a mitogen-induced signal transducer which binds to the ErbB-2 kinase domain. Mol Cell Biol, 2000. 20(20): p. 7735-50.

Forrester, E., et al., Effect of conditional knockout of the type II TGF-beta receptor gene in mammary epithelia on mammary gland development and polyomavirus middle T antigen induced tumor formation and metastasis. Cancer Res, 2005. 65(6): p. 2296-302.

Fujii, T., et al., A preliminary transcriptome map of non-small cell lung cancer. Cancer Res, 2002. 62(12): p. 3340-6.

Furuta, Y., et al., Retina- and ventral forebrain-specific Cre recombinase activity in transgenic mice. Genesis, 2000. 26(2): p. 130-2.

Gannon, M., et al., Analysis of the Cre-mediated recombination driven by rat insulin promoter in embryonic and adult mouse pancreas. Genesis, 2000. 26(2): p. 139-42.

Gannon, M., P.L. Herrera, and C.V. Wright, Mosaic Cre-mediated recombination in pancreas using the pdx-1 enhancer/promoter. Genesis, 2000. 26(2): p. 143-4.

Girard, L., et al., Genome-wide allelotyping of lung cancer identifies new regions of allelic loss, differences between small cell lung cancer and non-small cell lung cancer, and loci clustering. Cancer Res, 2000. 60(17): p. 4894-906.

Gu, H., et al., Deletion of a DNA polymerase beta gene segment in T cells using cell type-specific gene targeting. Science, 1994. 265(5168): p. 103-6.

Gu, H., Y.R. Zou, and K. Rajewsky, Independent control of immunoglobulin switch recombination at individual switch regions evidenced through Cre-loxP-mediated gene targeting. Cell, 1993. 73(6): p. 1155-64.

Hamerman, D., The biology of osteoarthritis. N Engl J Med, 1989. 320(20): p. 1322-30.

Hardouin, N. and A. Nagy, Gene-trap-based target site for cre-mediated transgenic insertion. Genesis, 2000. 26 (4): p. 245-52.

Herzog, C.R., Y. Wang, and M. You, Allelic loss of distal chromosome 4 in mouse lung tumors localize a putative tumor suppressor gene to a region homologous with human chromosome 1p36. Oncogene, 1995. 11(9): p. 1811-5.

Hulth, A., et al., Effect of transforming growth factor-beta and platelet-derived growth factor-BB on articular cartilage in rats. J Orthop Res, 1996. 14(4): p. 547-53.

Imai, T., P. Chambon, and D. Metzger, Inducible site-specific somatic mutagenesis in mouse hepatocytes. Genesis, 2000. 26(2): p. 147-8.

Jackson, E.L., et al., Analysis of lung tumor initiation and progression using conditional expression of oncogenic K-ras. Genes Dev, 2001. 15(24): p. 3243-8.

Kellendonk, C., et al., Hepatocyte-specific expression of Cre recombinase. Genesis, 2000. 26(2): p. 151-3.

Kilby, N.J., M.R. Snaith, and J.A. Murray, Site-specific recombinases: tools for genome engineering. Trends Genet, 1993. 9(12): p. 413-21.

Kohno, T. and J. Yokota, How many tumor suppressor genes are involved in human lung carcinogenesis? Carcinogenesis, 1999. 20(8): p. 1403-10.

Koo, H.M., et al., Ras oncogene-induced sensitization to 1-beta-D-arabinofuranosylcytosine. Cancer Res, 1999. 59 (24): p. 6057-62.

Lawrence, R.C., et al., Estimates of the prevalence of selected arthritic and musculoskeletal diseases in the United States. J Rheumatol, 1989. 16(4): p. 427-41.

Lomeli, H., et al., Targeted insertion of Cre recombinase into the TNAP gene: excision in primordial germ cells. Genesis, 2000. 26(2): p. 116-7.

Ma, P.C., et al., c-MET mutational analysis in small cell lung cancer: novel juxtamembrane domain mutations regulating cytoskeletal functions. Cancer Res, 2003. 63(19): p. 6272-81.

Ma, P.C., et al., Functional expression and mutations of c-Met and its therapeutic inhibition with SU11274 and small interfering RNA in non-small cell lung cancer. Cancer Res, 2005. 65(4): p. 1479-88.

Maddison, L.A., et al., Prostate specific expression of Cre recombinase in transgenic mice. Genesis, 2000. 26(2): p. 154-6.

Mai, M., et al., Activation of p73 silent allele in lung cancer. Cancer Res, 1998. 58(11): p. 2347-9.

Makkinje, A., et al., Gene 33/Mig-6, a transcriptionally inducible adapter protein that binds GTP-Cdc42 and activates SAPK/JNK. A potential marker transcript for chronic pathologic conditions, such as diabetic nephropathy. Possible role in the response to persistent stress. J Biol Chem, 2000. 275(23): p. 17838-47.

Mateescu, R.G., et al., Increased MIG-6 mRNA transcripts in osteoarthritic cartilage. Biochem Biophys Res Commun, 2005. 332(2): p. 482-6.

McBurney, M.W., et al., The mouse Pgk-1 gene promoter contains an upstream activator sequence. Nucleic Acids Res, 1991. 19(20): p. 5755-61.

Miettinen, P.J., et al., Epithelial immaturity and multiorgan failure in mice lacking epidermal growth factor receptor. Nature, 1995. 376(6538): p. 337-41.

Miettinen, P.J., et al., Impaired lung branching morphogenesis in the absence of functional EGF receptor. Dev Biol, 1997. 186(2): p. 224-36.

Miwa, T., T. Koyama, and M. Shirai, Muscle specific expression of Cre recombinase under two actin promoters in transgenic mice. Genesis, 2000. 26(2): p. 136-8.

Nagy, A., Cre recombinase: the universal reagent for genome tailoring. Genesis, 2000. 26(2): p. 99-109.

Niwa-Kawakita, M., et al., Targeted expression of Cre recombinase to myelinating cells of the central nervous system in transgenic mice. Genesis, 2000. 26(2): p. 127-9.

Nomoto et al., Cancer 28:342-46 (2000).

Nomoto, S., et al., Search for mutations and examination of allelic expression imbalance of the p73 gene at 1p36.33 in human lung cancers. Cancer Res, 1998. 58(7): p. 1380-3.

Orban, P.C., D. Chui, and J.D. Marth, Tissue- and site-specific DNA recombination in transgenic mice. Proc Natl Acad Sci U S A, 1992. 89(15): p. 6861-5.

Ovchinnikov, D.A., et al., Col2a1-directed expression of Cre recombinase in differentiating chondrocytes in transgenic mice. Genesis, 2000. 26(2): p. 145-6.

Paez, J.G., et al., EGFR mutations in lung cancer: correlation with clinical response to gefitinib therapy. Science, 2004. 304(5676): p. 1497-500.

Pante, G., et al., Mitogen-inducible gene 6 is an endogenous inhibitor of HGF/Met-induced cell migration and neurite growth. J Cell Biol, 2005. 171(2): p. 337-48.

Ragnarsson, G., et al., Loss of heterozygosity at chromosome 1p in different solid human tumours: association with survival. Br J Cancer, 1999. 79(9-10): p. 1468-74.

Robertson, EJ, In:Teratocarcinomas and Embryonic Stem Cells: A Practical Approach, EJ Roberson, ed. IRL Press, Washington, DC (1987).

Rountree, R.B., et al., BMP receptor signaling is required for postnatal maintenance of articular cartilage. PLoS Biol, 2004. 2(11): p. e355.

Rowan, A.D., Cartilage catabolism in arthritis: factors that influence homeostasis. Expert Rev Mol Med, 2001. p. 1-20.

Sandell, L.J. and T. Aigner, Articular cartilage and changes in arthritis. An introduction: cell biology of osteoarthritis. Arthritis Res, 2001. 3(2): p. 107-13.

Sargent, L.M., et al., Specific chromosomal aberrations in mouse lung adenocarcinoma cell lines detected by spectral karyotyping: a comparison with human lung adenocarcinoma. Cancer Res, 2002. 62(4): p. 1152-7.

Sauer, B. and N. Henderson, Cre-stimulated recombination at loxP-containing DNA sequences placed into the mammalian genome. Nucleic Acids Res, 1989. 17(1): p. 147-61.

Sauer, B. and N. Henderson, Site-specific DNA recombination in mammalian cells by the Cre recombinase of bacteriophage P1. Proc Natl Acad Sci U S A, 1988. 85(14): p. 5166-70.

Sauer, B. and N. Henderson, Targeted insertion of exogenous DNA into the eukaryotic genome by the Cre recombinase. New Biol, 1990. 2(5): p. 441-9.

Scharstuhl, A., et al., Inhibition of endogenous TGF-beta during experimental osteoarthritis prevents osteophyte formation and impairs cartilage repair. J Immunol, 2002. 169(1): p. 507-14.

Selby, P.B., A rapid method for preparing high quality alizarin stained skeletons of adult mice. Stain Technol, 1987. 62(3): p. 143-6.

Serra, R., et al., Expression of a truncated, kinase-defective TGF-beta type II receptor in mouse skeletal tissue promotes terminal chondrocyte differentiation and osteoarthritis. J Cell Biol, 1997. 139(2): p. 541-52.

Shinkai, Y., et al., RAG-2-deficient mice lack mature lymphocytes owing to inability to initiate V(D)J rearrangement. Cell, 1992. 68(5): p. 855-67.

Stephens, P., et al., Lung cancer: intragenic ERBB2 kinase mutations in tumours. Nature, 2004. 431(7008): p. 525-6.

Talts, J.F., C. Brakebusch, and R. Fassler, Integrin gene targeting. Methods Mol Biol, 1999. 129: p. 153-87.

Thiagalingam, S., et al., Loss of heterozygosity as a predictor to map tumor suppressor genes in cancer: molecular basis of its occurrence. Curr Opin Oncol, 2002. 14(1): p. 65-72.

Tokuchi, Y., et al., The expression of p73 is increased in lung cancer, independent of p53 gene alteration. Br J Cancer, 1999. 80(10): p. 1623-9.

Tsunoda, T., et al., A novel mechanism of nuclear factor kappaB activation through the binding between inhibitor of nuclear factor-kappaBalpha and the processed NH(2)-terminal region of Mig-6. Cancer Res, 2002. 62(20): p. 5668-71.

Utomo, A.R., A.Y. Nikitin, and W.H. Lee, Temporal, spatial, and cell type-specific control of Cre-mediated DNA recombination in transgenic mice. Nat Biotechnol, 1999. 17(11): p. 1091-6.

Van Beuningen, H.M., et al., Osteoarthritis-like changes in the murine knee joint resulting from intra-articular transforming growth factor-beta injections. Osteoarthritis Cartilage, 2000. 8(1): p. 25-33.

Virmani, A.K., et al., Allelotyping demonstrates common and distinct patterns of chromosomal loss in human lung cancer types. Genes Chromosomes Cancer, 1998. 21(4): p. 308-19.

Wick, M., et al., Identification of a novel mitogen-inducible gene (mig-6): regulation during G1 progression and differentiation. Exp Cell Res, 1995. 219(2): p. 527-35.

Yang, A., et al., p73-deficient mice have neurological, pheromonal and inflammatory defects but lack spontaneous tumours. Nature, 2000. 404(6773): p. 99-103.

Yang, X., et al., TGF-beta/Smad3 signals repress chondrocyte hypertrophic differentiation and are required for maintaining articular cartilage. J Cell Biol, 2001. 153(1): p. 35-46.

Zhang, Y.W., et al., Hepatocyte growth factor/scatter factor mediates angiogenesis through positive VEGF and negative thrombospondin 1 regulation. Proc Natl Acad Sci U S A, 2003. 100(22): p. 12718-23.

Zochbauer-Muller, S., A.F. Gazdar, and J.D. Minna, Molecular pathogenesis of lung cancer. Annu Rev Physiol, 2002. 64: p. 681-708.

* cited by examiner

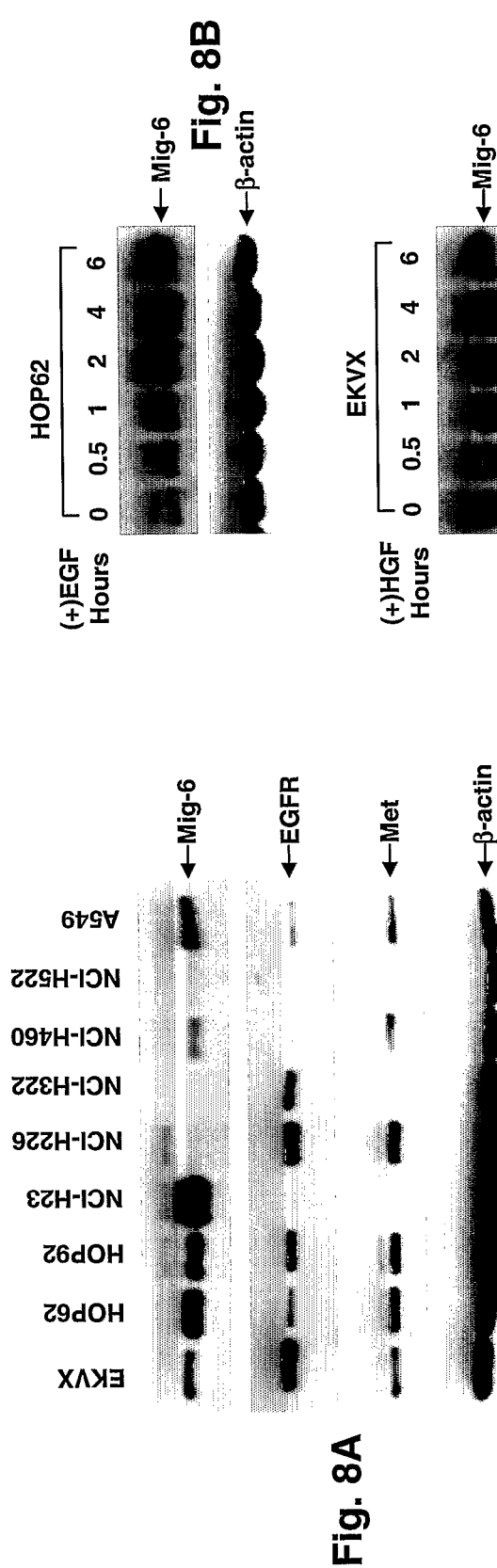
Fig. 8A
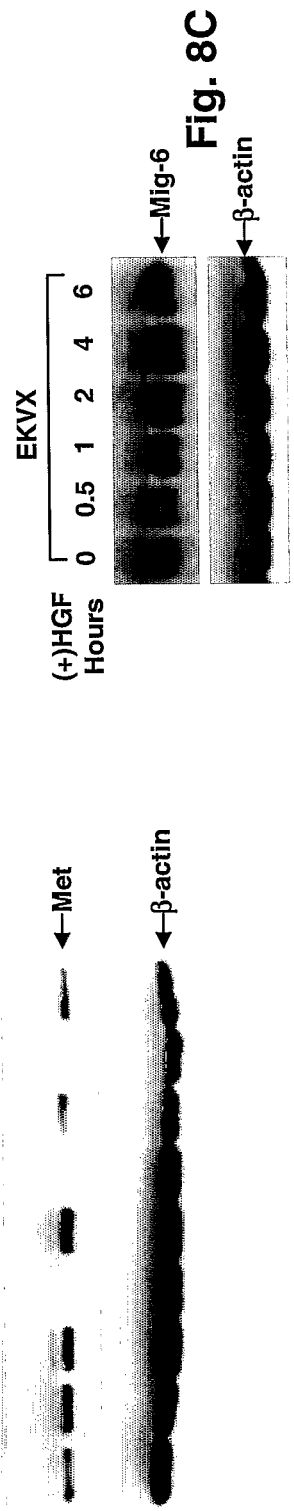
Fig. 8B
Fig. 8C
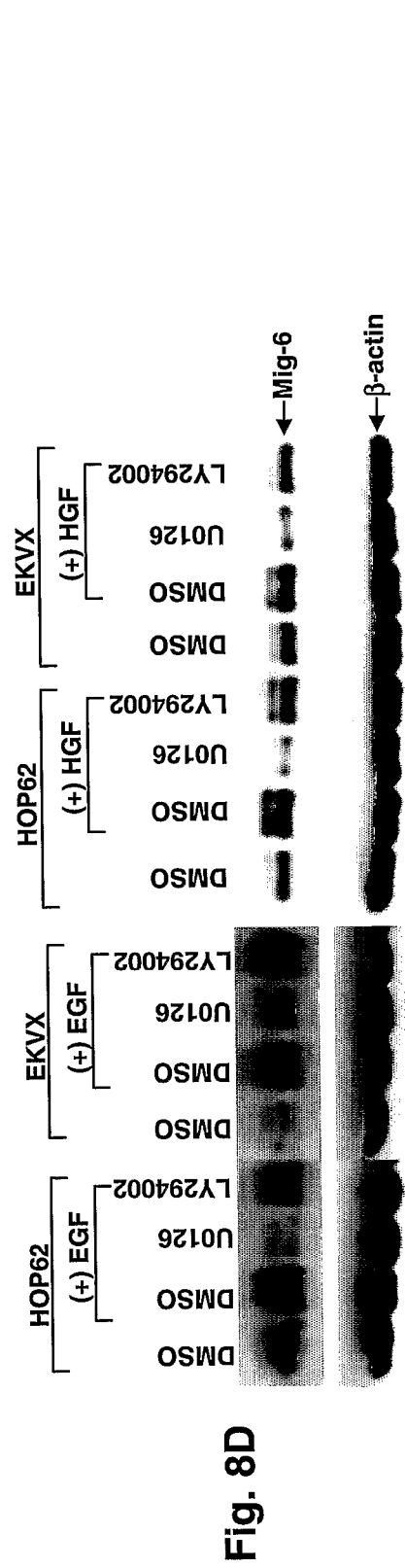
Fig. 8D

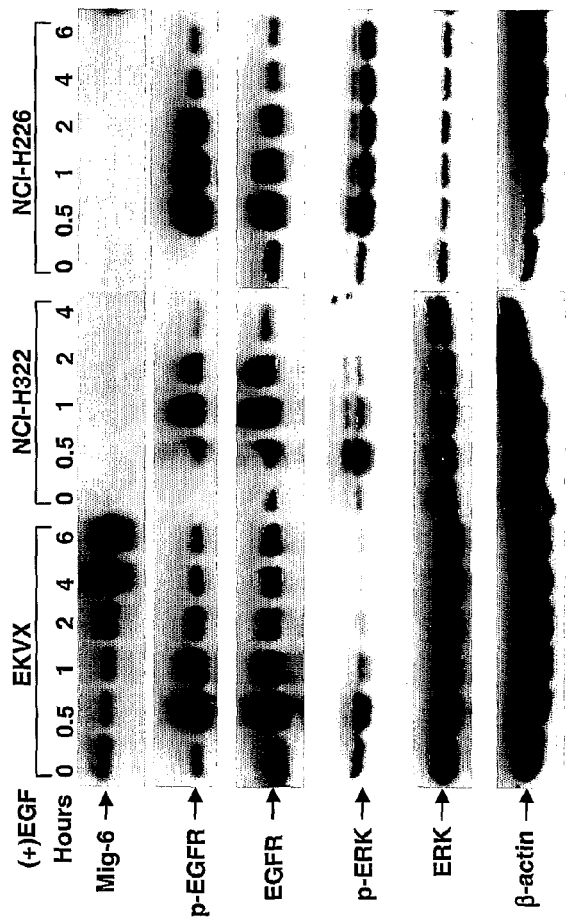
Fig. 9A
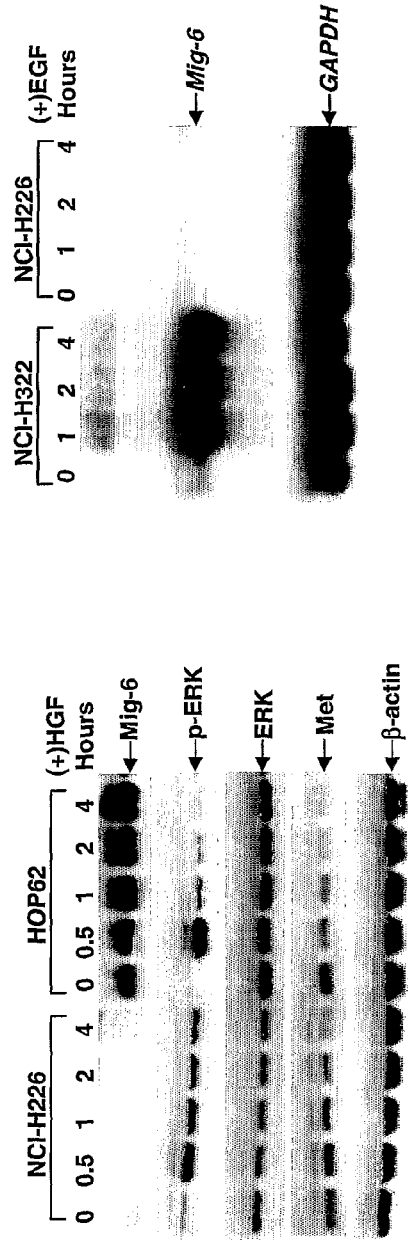
Fig. 9B
Fig. 9C

Wild Type 1041190A
(Cancer tissue)
(GCC→GTC)

1041190B
(Normal tissue)
(GCC→GTC)

Strategy for Generating Conditional Mig-6 Knockout/Rescue Mouse

MIG-6 KNOCKOUT MICE AND ELUCIDATION OF ASSOCIATION OF MIG-6 WITH EARLY ONSET DEGENERATIVE JOINT DISEASE AND ROLE AS A TUMOR SUPPRESSOR

This application is the U.S. National phase filing of PCT Application Serial No. PCT/US2006/023257, filed Jun. 15, 2006, which claims the benefit of provisional Ser. No. 60/690,493 filed Jun. 15, 2005, and provisional Ser. No. 60/789,612 filed Apr. 6, 2006, the entire contents of which are incorporated herein in their entirety.

BACKGROUND OF THE INVENTION

1. Field of the Invention

This invention in the field of molecular biology and medicine is directed to knockout mice in which the mig-6 gene is disrupted resulting in animals which develop early-onset joint abnormalities characteristic of osteoarthritis and are highly susceptible to tumorigenesis of a number of types of cancer, primarily lung cancer. These animals serve as models for testing potential drugs and other therapeutic measures to prevent or treat osteoarthritis, and to delay or attenuate tumor development and growth in humans.

2. Description of the Background Art

Degenerative joint disease, or osteoarthritis affects nearly 12% of the United States population between the ages of 25 and 74 (Lawrence, R C et al. *J. Rheumatol.* 16:427-41, 1989), and greatly interferes with quality of life by causing acute and chronic pain and disability. The characteristic features of this disease are joint pain, stiffness, joint enlargement and malalignment, damage of articular cartilage, and formation of osteophytes or bony outgrowths at the margin of synovial and cartilage junction. Currently, therapy is directed towards controlling symptoms and no disease modifying, or chondroprotective treatment is available. In addition, the costs for pain relief medication are astronomical. Although several genetic and biomechanical factors including heredity, obesity, injury and joint overuse are thought to contribute to the development of osteoarthritis, the molecular mechanism underlying this disease is still elusive. For a comprehensive discussion of osteoarthritis, see, for example, Koopman, W. J., In: *Arthritis and Allied Conditions, A Textbook of Rheumatology*, 13th Edition, Vol. 2 (Williams & Wilkins, Baltimore, Md., 1997; Redneck, D., *Diagnosis of Bone and Joint Disorders*, 4th Ed, Vol. 2 (WB Saunders Company, Philadelphia, Pa., 2002). Prior to the present invention, there was no known association between the Mig-6 gene and osteoarthritis.

Mig-6, also known as gene 33 or RALT (Florentine et al., *Mol. Cell. Biol.* 20:7735-50, 2000; Making et al., *J. Biol. Chem.* 275:17838-47, 2000), has been mapped to human chromosome 1p36. Mig-6 is an immediate early response gene that can be induced by stressful stimuli and growth factors, as well as by the oncoprotein Ras (Florentine et al., supra; Making et al., supra; Tsoumada et al., *Cancer Res.* 62, 5668-71, 2002). Mig-6 protein can directly interact with all four members of the ErbB family, including EGFR and ErbB2-4, and it acts as a negative feedback regulator of the ErbB receptor tyrosine kinase (RTK) pathway (Florentine et al., supra; Anastasia et al., *Oncogene* 22:4221-34, 2003; XII et al., *J. Biol. Chem.* 280:2924-33, 2005). Recently, it has been reported that down-regulated expression of the Mig-6 gene is observed in human breast carcinomas, which correlates with reduced overall survival of breast cancer patients (Matched et al., *Cancer Res.* 64:844-56, 2004; Anastasi et al., 2005). However, no mutations in Mig-6 have been detected in human breast carcinomas (Anastasi et al., *Oncogene* 24:4540-48, 2005). Indeed, no mutations have been reported in Mig-6 to date, and the role of Mig-6 in human lung, gallbladder, and bile duct carcinogenesis has not been assessed.

Allelic loss of chromosome 1p36 is among the most prominent genetic abnormalities observed in human lung cancer (Fujii et al., *Cancer Res.* 62:3340-46, 2002; Girard et al., *Cancer Res.* 60:4894-4906, 2000; Nomoto et al., *Cancer* 28:342-46, 2000), indicating that a critical tumor suppressor gene(s) exists in this locus. Moreover, loss of heterozygosity (LOH) of the distal region of mouse chromosome 4, a region syntenic with human chromosome 1p36, is also frequently observed in mouse lung carcinogenesis (Herzog et al., *Oncogene* 11:1811-15 1995; Herzog et al., *Cancer Res.* 62:6424-29, 2002). The p53 tumor suppressor gene homologue, p73, is located in 1p36, but no mutations have been identified in human lung cancers (Nomoto et al., *Cancer Res.* 58:1380-83, 1998), excluding it as the responsible tumor suppressor gene.

SUMMARY OF THE INVENTION

The present inventors generated Mig-6 deficient mice and demonstrate here that Mig-6 is essential for normal joint maintenance and that loss of Mig-6 leads to early onset degenerative joint disease. The results disclosed herein provide (a) a better understanding the role of Mig-6 during mouse development and homeostasis, (b) a mouse model for studying degenerative joint disease and screening or testing drugs which prevent or ameliorate symptoms of such diseases, and (c) methods and compositions for treating early onset degenerative joint disease and related conditions that are influenced by the Mig-6 gene or its absence.

It is further disclosed herein that Mig-6, a gene located in human chromosome 1p36, one of the most frequent genetic alterations observed in human lung cancer, implicating the existence of a critical tumor suppressor gene(s), is mutated in certain human lung cancer cell lines and primary lung cancer. Disruption of Mig-6 in mice, in addition to the changes noted above, leads to the development of epithelial hyperplasia or cancer in the lung, gallbladder, and bile duct, providing evidence that Mig-6 is a tumor suppressor gene and a candidate gene for the frequent 1p36 genetic alterations found in lung cancer. Thus, Mig-6 is useful as a tumor marker as well, and appropriate manipulation of the expression of this gene and of the Mig-6 protein and the pathways which it influences serve as the basis for novel methods to prevent or treat the development of cancers influenced by this gene.

The present invention provides knockout mouse, the genome of which is manipulated to comprise a disruption of one or both alleles of the mig-6 gene, wherein when both alleles are disrupted, the mouse exhibits joint abnormalities characteristic of osteoarthritis as compared to a wild type mouse in which the mig-6 gene is not disrupted. The knockout mouse may be homozygous or heterozygous for the mig-6 gene disruption. The disruption prevents the expression of a functional Mig-6 protein.

In the above knockout mouse, the disruption of both alleles of the mig-6 gene further results in the mouse exhibiting increased tumorigenesis in the lung, gall bladder and/or bile duct compared to the wild type mouse.

In the above knockout mouse, the disruption preferably results from replacement of part of the mig-6 gene with a neo gene under control of a PGK-1 promoter.

The invention includes a conditional knockout mouse the genome of which is manipulated to comprise at least one mutant mig-6 allele that comprises, from 5' to 3', a first loxP site, a first FLP recombinase target (FRT) sequence, a lacZ DNA coding sequence, PGK-Neo cassette, a second FRT sequence, a human Mig-6 cDNA coding sequence and a second loxP site, such that when
(a) when a FLP recombinase is provided via a genetic cross with a FLP recombinase-expressing mouse, the ends of the first FRT and the second FRT are exchanged such that the LacZ and PGK-Neo sequence are deleted and the human Mig-6 cDNA coding sequence is rescued; and
(b) when a Cre-recombinase is provided via a genetic cross with a Cre-expressing mouse, the Mig-6 coding sequence is deleted resulting in the absence of Mig-6 cDNA.

The Cre recombinase is preferably under the control of a tissue specific promoter, so that the deletion in (b) occurs in a tissue-specific manner, thus making the knockout state a tissue-specific one.

Also provided herein is a cell derived or isolated from the above knockout mouse or conditional knockout mouse. The cell is preferably a multipotent stem cell, a lineage-committed stem cell, a tumor or cancer cell, a chondrocyte, or a chondrocyte precursor.

The invention is also directed to a Mig-6 DNA knockout construct comprising a selectable marker sequence flanked by DNA sequences homologous to mig-6 genomic DNA, wherein when the construct is introduced into a mouse or an ancestor of a mouse at an embryonic stage, the selectable marker sequence disrupts the mig-6 gene in the embryonic cell and mouse that results in the mouse exhibiting (a) joint abnormalities characteristic of osteoarthritis and (b) enhanced tumorigenesis of lung, gall bladder and/or bile ducts.

The Mig-6 DNA knockout construct of claim 12, wherein the construct consists of, 5' to 3', (a) a first mig-6 genomic DNA fragment; (b) a neo cassette comprising a constitutive promoter; (c) a second mig-6 genomic DNA fragment which is 3' from the first mig-6 genomic DNA fragment in murine mig-6 genomic DNA, and (d) optionally, a thymidine kinase cassette.

In a preferred The Mig-6 DNA knockout construct of claim 13, (a) the first mig-6 genomic DNA fragment is an approximately 5 kb polynucleotide most of which is located upstream of exon 2 in genomic DNA but includes at it's 3' end a sequence from exon 2; preferably it is SEQ ID NO:19, (b) the constitutive promoter of the neo cassette is a PGK-1 promoter, and (c) a second mig-6 genomic DNA fragment is an approximately 3 kb polynucleotide located downstream of exon 4; preferably it is SEQ ID NO:20.

Also provided is a vector comprising any Mig-6 DNA knockout construct of the invention.

The invention includes a Mig-6 DNA conditional knockout construct comprising, in the 5' to 3' direction: (a) an approximately 5 kb mig-6 genomic DNA fragment most of which is located upstream of exon 2 in genomic DNA but includes at it's 3' end a sequence from exon 2; (b) a first loxP site; (c) a first FRT sequence; (d) a lacZ DNA coding sequence; (e) a PGK-Neo cassette; (f) a second FRT sequence; (g) a human Mig-6 cDNA coding sequence; (h) a second loxP site; (i) a second mig-6 genomic DNA fragment that is an approximately 3 kb polynucleotide located downstream of exon 4; and (j) optionally an HSV thymidine kinase cassette.

The invention is also directed to a method of producing a heterozygous knockout mouse the genome of which comprises a disruption of the mig-6 gene, the method comprising the steps of: (a) transforming a mouse embryonic stem cell with a knockout construct or vector according to any of claims 12-16, thereby producing a transformed embryonic stem cell; (b) introducing the transformed embryonic stem cell into a mouse blastocyst; (c) implanting blastocyst comprising the transformed embryonic cell into a pseudopregnant female mouse; (d) allowing the blastocyst to undergo fetal development to term; and (e) allowing the developed fetus to be born as the heterozygous knockout mouse, wherein the knockout mouse so produced exhibits, when the disrupted mig-6 is in a homozygous state, (i) joint abnormalities characteristic of osteoarthritis and (ii) enhanced tumorigenesis of lung, gall bladder and/or bile ducts.

The above method may further comprise (f) testing the mouse after step (e) to verify that its genome comprises a disrupted mig-6 gene in at least one allele.

The invention provides a method for producing a homozygous knockout mouse the genome of which comprises a disruption of the mig-6 gene, which mouse exhibits (i) joint abnormalities characteristic of osteoarthritis and (ii) enhanced tumorigenesis of lung, gall bladder and/or bile ducts, the method comprising: (a) interbreeding heterozygous mice produced in accordance with claim 18; and (b) selecting offspring in which the disruption of the mig-6 gene is homozygous.

In another embodiment, the invention is directed to a method for selecting a candidate agent for use in the treatment or prevention of osteoarthritis, comprising: (a) administering a candidate agent to a knockout mouse as above, wherein the disruption of mig-6 results in joint abnormalities characteristic of osteoarthritis; (b) measuring the response of the knockout mouse to the agent; and (c) selecting an agent based on its ability to decrease or prevent symptoms of osteoarthritis in the knockout mouse.

Also included is a method of determining whether a compound or agent prevents or treats symptoms of osteoarthritis, comprising: (a) administering a compound or agent to a knockout mouse whose genome is genetically modified to comprise a disruption of mig-6 gene, wherein the disruption causes the development of joint abnormalities characteristic of osteoarthritis (b) determining whether the compound prevents or treats the symptoms.

Also included is a method of determining whether a compound or agent prevents or treats symptoms of osteoarthritis, comprising: (a) administering a compound or agent to the knockout mouse of any of claims 1-8, and (b) determining whether the compound prevents or treats the symptoms.

The invention provides a method for evaluating the effect of a test agent or treatment for its ability to delaying development of or treat a human tumor or cancer, comprising (a) administering the test agent to, or performing the treatment on, the knockout mouse of any of claims 1-8; (b) evaluating the time of appearance, rate of development, growth, or metastasis of tumors in the mice compared to the knockout mice not given the agent or treatment; (c) comparing results obtained in step (b) to the time of appearance, rate of development, growth, or metastasis of tumors in the knockout mice which have not been given the agent or treatment, wherein a significant delay in appearance, attenuation of development, growth or metastasis of the tumors in (b) compared to (c) indicates that the agent or treatment has the ability to delay development or treat the tumor or cancer.

In the above method, the human tumor or cancer is preferably carcinoma, most preferably lung carcinoma.

In the above method, the tumors being evaluated in the mice are preferably lung tumors, gall bladder tumors or bile duct tumors.

A method for detecting a structurally or functionally abnormal mig-6 gene in a subject, the method comprising detecting in a sample of cells, tissue or nucleic acid from the subject (a) the presence of a mutation in the coding sequence of the mig-6 gene; (b) a decrease or absence of expression of the mig-6 gene; (c) increased expression of the mig-6 gene secondary to downstream blockade in a signalling pathway in which Mig-6 is a participant; (d) the presence of a mutation or decreased activity in a promoter of the mig-6 gene; or (e) abnormal methylation of at least a part of the mig-6 gene thereby detecting a structurally or functionally abnormal mig-6 gene.

In the above method the presence of an abnormal mig-6 gene indicates that the subject has increased susceptibility to the development of any disease or condition associated with decreased or absent mig-6 function, compared to a subject with a structurally or functional normal mig-6 gene, such as increased susceptibility to the development of osteoarthritis and/or increased susceptibility to the development of cancer, such as carcinoma of the lung, gall bladder or bile duct.

When the mutant mig-6 gene is characterized as a point mutation, a deletion or truncation, or a translocation, it is detected by sequencing of at least a portion of the mig-6 gene. Preferably this is done after the nucleic acid of the sample is subjected to RT-PCR. For this PCR, the following primers are preferred:

```
(a) forward prime
5'-TCTTCCACCGTTGCCAATC-3';      [SEQ ID NO: 8]

(b) reverse primer
5'-TTCCACCTCACAGTCTGTGTCAT-3';  [SEQ ID NO: 9]
and (c) TaqMan Probe
5'-CTGAAGCCCTCTCTCT-3'.         [SEQ ID NO: 10]
```

The above method may be used to examine and detect a subject who is heterozygous or homozygous for the mutant mig-6 gene.

To test expression of the mig-6 gene is detected, hybridization to a nucleic acid microarray is a preferred method. Expression of the mig-6 gene may be detected by measuring the presence or quantity of the Mig-6 protein in the sample, for example using an antibody, by method that include ELISA and Western blots or any other conventional immunoassay.

The invention provides a method for detecting a structurally or functionally abnormal mig-6 gene in tumor from subject, the method comprising detecting in a sample of tumor cells, tissue or nucleic acid from the tumor: (a) the presence of a mutation in the coding sequence of the mig-6 gene (b) a decrease or absence of expression of the mig-6 gene; (c) an increase in expression of the mig-6 gene secondary to downstream blockade in a signalling pathway in which Mig-6 is a participant; (d) the presence of a mutation or decreased activity in a promoter of the mig-6 gene; or (e) abnormal methylation of at least a part of the mig-6 gene thereby detecting a structurally or functionally abnormal mig-6 gene in the tumor.

In this method, one or more cells lines may be produced from the tumor prior to the detecting, and the detecting carried out on the cell line or lines.

In the above method for detecting a structurally or functionally abnormal mig-6 gene in a subject, the subject is preferably a human.

BRIEF DESCRIPTION OF THE DRAWINGS

FIG. 8A-8D: Mig-6 expression is regulated by EGF and HGF/SF through the MAP kinase pathway in human lung cancer cells. FIG. 8A shows the expression of Mig-6, EGFR, and Met proteins in human lung cancer cell lines. Whole cell extracts were prepared from lung cancer cell lines and subjected to western blot analyses probed with anti-Mig-6, anti-EGFR, and anti-Met antibodies. The β-actin serves as an internal control for visualizing the amount of protein loaded in each lane. FIG. 8B shows up-regulation of Mig-6 by EGF. The cell lysates derived from HOP62 cells with or without EGF (50 ng/ml) treatment for the indicated times were subjected to western blot analysis using anti-Mig-6 antibody. FIG. 8C shows up-regulation of Mig-6 by HGF/SF. EKVX cells were treated with HGF/SF (200 units/ml) for the indicated times, followed by western blot analysis. FIG. 8D shows that the MAPK pathway mediates EGF- and HGF/SF-induced Mig-6 expression. HOP62 and EKVX cells were treated with U0126 or LY294002 for 1 h, respectively, followed by EGF (50 ng/ml) or HGF/SF (200 units/ml) treatment for additional 4 h, respectively. Cells treated with DMSO were used as controls. Western blotting was performed as described above.

FIG. 9A-9C: The regulation of Mig-6 expression by EGF or HGF/SF is defective in NCI-H226 cells. FIG. 9A shows that EGF failed to induce Mig-6 protein expression in NCI-H226 cells. EKVX, NCI-H322, and NCI-H226 cells were serum-starved and then treated with EGF (50 ng/ml) for the indicated times. At each time point, the cell lysates were prepared and subjected to western blot analyses using the indicated antibodies. FIG. 9B shows that induction of Mig-6 protein by HGF/SF was not detected in NCI-H226 cells. Serum-starved NCI-H226 and HOP62 cells were treated with HGF/SF (200 units/ml) for the indicated times. Western blotting was performed as described above using the indicated antibodies. FIG. 9C shows that EGF failed to induce Mig-6 mRNA transcription. NCI-H322 and NCI-H226 cells were serum-starved overnight and treated with EGF (50 ng/ml) at the indicated times. At each time point, RNA was isolated and subjected to northern blot analysis with a [$^{32}$P]-labeled Mig-6 probe. As a control, GAPDH was also analyzed.

FIG. 10A shows that the Mig-6 gene is mutated in the NCI-H226 and NCI-H322M non-small cell lung cancer cell lines. The upper panels show the wild-type sequences and the lower panels show the mutant sequences in Mig-6. The arrows mark the mutated nucleotides derived from the two cell lines. FIG. 10B shows the identification of a heterozygous germline mutation of Mig-6 in one primary lung cancer. The top panel shows the wild-type sequence, the middle panel shows the mutant sequence in Mig-6 derived from the primary lung cancer tissue, and the lower panel shows the sequence derived from the normal control tissue from the same patient. The arrows indicate the mutated nucleotide. FIG. 10C is a schematic representation of the Mig-6 genomic structure, the protein, and indicates the location of the identified mutations.

FIG. 11A shows the normal lung of a 1-year-old Mig-6$^{+/+}$ mouse.

FIG. 11B shows the normal lung of a 1-year-old Mig-6$^{+/-}$ mouse.

FIG. 11C shows a representative image showing the bronchi and bronchiole epithelial hyperplasia observed in the lung of a 9-month-old Mig-6$^{-/-}$ mouse.

FIG. 11D shows proliferation of round cells in the alveoli of Mig-6$^{-/-}$ lung (1 year old).

FIG. 11E shows development of lung adenomas in a Mig-6$^{-/-}$ mouse (9.5 months old). The adenoma has distinct borders and a monomorphic population of alveolar/bronchiolar cells. Note shows this mouse had two adenomas on two different lobes.

FIG. 11F is a higher magnification of the image in the square shown in FIG. 11E.

FIG. 11G shows development of lung adenocarcinoma in an 8.5-month-old Mig-6$^{-/-}$ mouse. The large early alveolar/bronchiolar carcinoma shows an indistinct border and central necrosis with cholesterol clefts.

FIG. 11H is a higher magnification of the image in the square shown in FIG. 11G.

FIG. 12A shows gallbladder hyperplasia in a Mig-6$^{-/-}$ mouse. H&E sections of gallbladders derived from age-matched (2 months) Mig-6$^{+/-}$ and Mig-6$^{-/-}$ mice are shown. FIG. 12B shows bile duct adenocarcinoma in a Mig-6$^{-/-}$ mouse. Bile duct sections derived from 10-month-old Mig-6$^{+/-}$ and Mig-6$^{-/-}$ mice are shown. FIG. 12C shows hyperproliferation of epithelial cells in Mig-6$^{-/-}$ gallbladder. The sections of gallbladder tissues (as shown in FIG. 12A) were immunohistochemically stained with anti-PCNA antibody. The brown-stained cells are PCNA-positive.

DESCRIPTION OF THE PREFERRED EMBODIMENTS

Figure 1A:
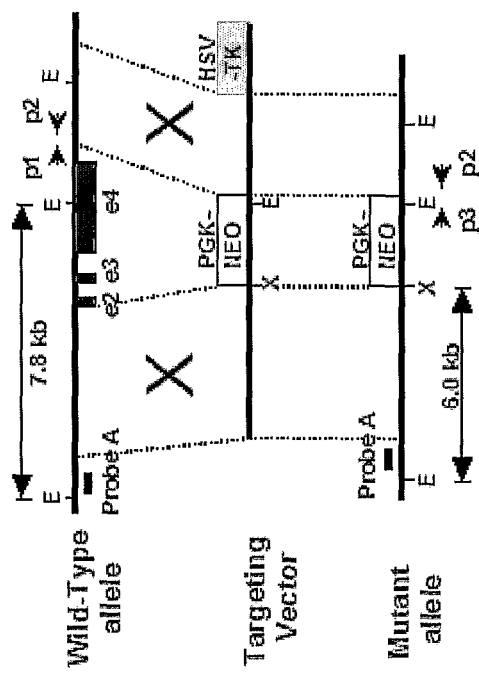
FIG. 1A-1C. Targeted disruption of Mig-6 gene. (A) Diagram of strategy for targeting Mig-6 locus. E, EcoRV; X, XhoI. (B) Southern Blot analysis and PCR-based genotyping. A 7.8 kb fragment for the wild-type allele and 6 kb fragment for the mutant allele was detected from EcoRV and XhoI double digested genomic DNA by hybridization with probe A (left panel). The PCR-based genotyping (right panel) detected a 360-bp DNA fragment from wild type allele (p1 & p2 primer pair) and a 800-bp DNA fragment from the mutant (disrupted) allele (p2 & p3 primer pair). (C) Elimination of Mig-6 expression in Mig-6$^{-/-}$ mouse tissues. Total RNAs isolated from the liver and thymus of Mig-6$^{+/+}$, Mig-6$^{+/-}$ and Mig-6$^{-/-}$ mice were subjected to Northern Blot analysis hybridized with mouse Mig-6 cDNA probe. The β-actin serves as internal control.

According to the present invention, mechanical joint stress constitutively stimulates joint regeneration by inducing certain growth factors such as transforming growth factor β (TGF-β), bone morphogenetic protein (BMP) and other cytokines that stimulate proliferation and differentiation of cells required for joint renewal. Under normal conditions, this regenerative activity in the joint is counter-balanced by a suppressor activity of Mig-6 that fine-tunes the extent of proliferation and renewal. Losing the suppressive function of Mig-6 results in over-proliferation of mesenchymal progenitor cells that leads to an abnormal state of chondrogenic differentiation and bony outgrowth (FIG. 5), which are typical osteoarthritic pathologies.

The profound osteoarthritic phenotype of Mig-6 deficient mice make them a very useful model for (1) determining what factors in the Mig-6 signaling pathway are involved in osteoarthritis; (2) understanding the molecular mechanism underlying this disease process; and (3) testing drugs or therapies which may help to alleviate the symptoms or alter the disease progression of osteoarthritis.

The present inventors have also discovered that the Mig-6 gene is mutated in human non-small cell lung cancer (NSCLC) cell lines such as NCI-H226 and NCI-H322M, as well as in one primary human lung cancer. Loss of Mig-6 function can result from dysregulation of its expression by RTK signaling. To this end, severalanimals in which Mig-6 was disrupted by gene targeting developed epithelial hyperplasia as well as adenoma or adenocarcinoma in the lung, gallbladder, and bile duct. These outcomes indicate that Mig-6 is a candidate tumor suppressor gene. The gene or its encoded protein can serve as a biomarker as well as a target for antitumor therapy.

DEFINITIONS

"Gene targeting" is a type of homologous recombination that occurs when a fragment of genomic DNA is introduced into a mammalian cell and that fragment locates and recombines with endogenous homologous sequences.

A "knockout mouse" (or "KO mouse") is a mouse in the genome of which a specific gene has been inactivated by the method of gene targeting. A knockout mouse can be a heterozygote (i.e., one defective/disrupted allele and one wild-type allele) and a homozygote (i.e., two defective/disrupted alleles). "Knockout" of a target gene means an alteration in the sequence of the gene that results in a decrease or, more commonly, loss of function of the target gene, preferably such that target gene expression is undetectable or insignificant. A knock-out of an Mig-6 gene means that function of the Mig-6 gene has been substantially decreased or lost so that Mig-6 expression is not detectable (or may only be present at insignificant levels. The term "knockout" is intended to include partial or complete reduction of the expression of at least a portion of a polypeptide encoded by the targeted endogenous gene (here mig-6) of a single cell, a population of selected cells, or all the cells of a mammal.

KO mice of the present invention include "conditional knockouts" (described in more detail below) in which, by inclusion of certain sequences in or surrounding the altered target, it is possible to control whether or not the target gene is rendered nonfunctional. This control can be exerted by exposure of the animal to a substance that promotes target gene alteration, introduction of an enzyme that promotes recombination at the target gene site (e.g., Cre in the Cre-lox system), or any other method that directs or controls the target gene alteration postnatally. Conditional knock-outs of Mig-6 gene function are also included within the present invention. Conditional knock-outs are transgenic animals that exhibit a defect in Mig-6 gene function upon exposure of the animal to a substance that promotes target gene alteration, introduction of an enzyme that promotes recombination at the target gene site (e.g., Cre in the Cre-loxP system), or other method for directing the target gene alteration. For example, an animal having a conditional knock-out of Mig-6 gene function can be produced using the Cre-loxP recombination system (see, e.g., Kilby et al. 1993 *Trends Genet* 9:413-421). Cre is an enzyme that excises the DNA between two recognition sequences, termed loxP. This system can be used in a variety of ways to create conditional knock-outs of Mig-6. For example, in addition to a mouse in which the Mig-6 sequence is flanked by loxP sites a second mouse transgenic for Cre is produced. The Cre transgene can be under the control of an inducible or developmentally regulated promoter (Gu et al. 1993 Cell 73:1155-1164; Gu et al. 1994 Science 265:103-106), or under control of a tissue-specific or cell type-specific promoter (e.g., a pancreas-specific promoter or brain tissue-specific promoter; see below). The Mig-6 transgenic is then crossed with the Cre transgenic to produce progeny deficient for the Mig-6 gene only in those cells that expressed Cre during development.

A "marker gene" serves as a selectable marker that facilitates the isolation of rare transfected cells from the majority of treated cells in the population. A non-comprehensive list of such markers includes neomycin phosphotransferase (neo), hygromycin B phosphotransferase, xanthine/guanine phosphoribosyl transferase, herpes simplex thymidine kinase (TK), and diphtheria toxin By "construct" is meant a recombinant nucleic acid molecule, generally DNA, that has been generated for the purpose of the expression of a specific nucleotide sequence(s), or is to be used in the construction of other recombinant nucleotide sequences.

The term "knockout construct" refers to a nucleotide sequence that is designed to undergo homologous recombination with the endogenous targeted gene to disrupt it and thereby decrease or suppress expression of a polypeptide encoded by the targeted gene in one or more cells of a mammal, preferably a mouse. The nucleotide sequence used as the knockout construct is typically comprised of (1) DNA from some portion of the targeted endogenous gene (which may include part or all of one or more exon sequences, intron sequences, and/or promoter sequences) and (2) a selectable marker sequence used to detect the presence of the knockout construct in the cell and which serves as a basis for selecting cells carrying the disrupted recombined sequence. In the present invention, the knockout construct is inserted into a cell that comprises the endogenous mig-6 gene that is to be knocked out. The knockout construct can integrate with one or both alleles of the endogenous mig-6 gene, which results in the transcription of the full-length endogenous mig-6 gene being disrupted or prevented. Integration of the Mig-6 knockout construct of the present invention into the chromosomal DNA preferably takes place via homologous recombination. This requires that regions of the Mig-6 knockout construct are homologous or complementary to endogenous mig-6 genomic DNA sequences so that the construct, after insertion into a cell, can hybridize to the genomic DNA. This permits recombination between the construct and the genomic DNA leading to incorporation of the knockout construct into the corresponding position of the genomic DNA).

Typically, the knockout construct is inserted into an undifferentiated cell termed an embryonic stem cell (ES cell). ES cells are usually derived from an embryo or blastocyst of the same species as the developing embryo into which it can be introduced, as discussed below The terms "disruption of the gene", "gene disruption", "suppressing expression", and "gene suppression", refer to insertion of a Mig-6 nucleotide sequence knockout construct into a homologous region of the coding region(s) of the endogenous mig-6 gene and/or the promoter region of this gene so as to decrease or prevent expression of the full length Mig-6 protein in the cell. Preferably, a knockout construct comprises an antibiotic resistance gene which is inserted into the Mig-6 genomic DNA that is to be disrupted. When this knockout construct is inserted into an ES cell, the construct integrates into the genomic DNA of at least one Mg-6 allele, which is referred to as "transformation" or "transduction.". Progeny cells of the of the transformed cell will no longer express Mig-6, or will express it at a decreased level and/or in a truncated or other mutated form, as the endogenous coding region of Mig-6 is now disrupted by the antibiotic resistance gene. As noted elsewhere, a preferred antibiotic resistance gene is the neo gene under control of a PGK-1 promoter.

The "marker sequence" or "selectable marker" is a nucleotide sequence that is (1) part of a larger knockout construct and is used to disrupt the expression of Mig-6, and (2) used as a means to identify and, more importantly, to positively select those cells that have incorporated the Mig-6 knockout construct into the chromosomal DNA. The marker sequence may be any sequence that serves these purposes, and typically is encodes a protein that confers a detectable/selectable trait on the cell, such as an antibiotic resistance gene or an assayable enzyme not naturally found in the cell. The marker sequence typically includes homologous (same species) or heterologous (different species) promoter that drives expression pf the marker.

The terms "rodent" and "rodents" refer to all members of the phylogenetic order Rodentia including any and all progeny of all future generations derived therefrom. The term "murine" and "mouse" refers to any and all members of the family Muridae, primarily mice.

The term "progeny" refers to any and all future generations of animals derived or descendant from a particular progenitor mammal, preferably a KO mammal, most preferably a KO mouse in which the mig-6 gene has been disrupted (whether heterozygous or homozygous for the disruption). Progeny of any successive generation are included herein such that the progeny, the $F_1$, $F_2$, $F_3$, generations and so on indefinitely comprising the disrupted gene (with the knockout construct) are included in this definition.

By "Mig-6 associated disorder" is meant a physiological state or pathological condition or disease associated with altered Mig-6 function (e.g., due to aberrant, Mig-6 expression, usually underexpression, or a defect in Mig-6 expression or in the Mig-6 protein). Such Mig-6 associated disorders can include, but are not necessarily limited to, disorders associated with reduced or absent Mig-6 protein resulting in a phenotype characterized by joint abnormalities characteristic of human osteoarthritis and/or increased susceptibility to tumorigenesis, particularly of carcinomas, such as lung, gall bladder and bile duct cancer.

As noted above, the invention also provides a method for screening, testing and selecting agents for possible use in the prevention, attenuation or treatment of any disease or disorder associated with abnormalities in the structure or function of the mig-6 gene. Such diseases include, but are not limited to, osteoarthritis and cancer. The potential therapeutic or preventative agents are selected on the basis of whether there is a statistical significance between test response of the knockout mouse of the invention to which the agent is administered compared to a control KO mouse which are not treated, or treated with control agent (such as the vehicle only).

Mig-6 nucleotide and amino acid sequences in mice and humans are described below.

```
Mouse Mig-6 coding sequence
                                                    (SEQ ID, NO: 15)
(including an italicized, underscored stop codon which is not counted
in the nt number)
atg tca aca gca gga gtt gct gct cag gat att cga gtc cca tta aaa    48 act gga ttt ctc cat aat ggt cag gcc ttg ggg aat atg aag tcc tgc    96 tgg ggc agt cac agt gag ttt gaa aat aac ttt tta aat att gat cca   144 ata acc atg gcc tac aat ctg aac tcc cct gct cag gag cac cta aca   192 act gtt gga tgt gct gct cgg tct gct cca ggg agc ggc cac ttc ttt   240 gca gag tgt ggt cca tct cca agg tca agc ttg ccc cct ctt gtt atc   288 tca cca agt gaa agc tcg gga cag cgt gaa gag gat caa gtt atg tgt   336 ggt ttt aag aaa ctc tca gtg aat ggg gtc tgc act tcc aca cct cca   384 ctt aca ccc att aaa agc tgc cct tcc cct ttc ccc tgt gcg gct ctg   432 tgt gat cgg ggt tct cgg ccg ctc ccg cca ctg ccc atc tct gaa gac   480 cta tgt gtg gat gag gcc gac agt gag gta gag ctt cta acc acc agc   528 tca gac aca gac ttg ctt tta gaa gac tct gcg cct tca gat ttc aaa   576 tac gat gct cct ggc agg cgc agc ttc cgt ggg tgc ggc cag atc aac   624 tat gca tat ttt gac agc cca act gtt tct gtg gca gat ctt agc tgt   672 gca tct gac cag aac aga gtt gtt cca gac cca aac cct ccc cca cct   720 caa agc cat cgc aga tta agg agg tct cac tca gga cca gct ggg tca   768 ttt aac aag cca gcc att cgg ata tct agc tgc aca cac aga gct tct   816 cct agc tct gat gaa gac aag cct gag gtc cct ccc agg gtt cct ata   864
```

-continued

```
cct cct agg cca gca aag cca gac tat aga cgg tgg tca gca gaa gtg      912
acc tcc aac acc tac agt gat gaa gat agg cct ccc aaa gtc ccc ccg      960
aga gaa cct ttg tct cgg agt aac tcc cgt acc cca agt cct aaa agc     1008
ctt ccg tct tac ctc aat ggg gtc atg ccc cca aca cag agc ttc gct     1056
cct gac ccc aag tat gtc agc agc aaa gcc ctg cag aga cag agc agc     1104
gaa gga tct gcc aac aag gtt cct tgc atc ctg ccc att att gaa aat     1152
ggg aag aag gtt agc tca acg cat tat tac tta cta cct gag agg cca     1200
ccg tac ctg gac aaa tat gaa aag tat ttt aag gaa gca gaa gaa aca     1248
aac cca agc acc caa att cag cca tta cct gct gcc tgt ggt atg gcc     1296
tct gcc aca gaa aag ctg gcc tcc aga atg aaa ata gat atg ggt agc     1344
cac ggg aag cgc aaa cac tta tcc tac gtg gtt tct cca taa             1383
```

Mouse Mig-6 Amino Acid Sequence
(SEQ ID NO: 16)

```
MSTAGVAAQD IRVPLKTGFL HNGQALGNMK SCWGSHSEFE NNFLNIDPIT MAYNLNSPAQ   60
EHLTTVGCAA RSAPGSGHFF AECGPSPRSS LPPLVISPSE SSGQREEDQV MCGFKKLSVN  120
GVCTSTPPLT PIKSCPSPFP CAALCDRGSR PLPPLPISED LCVDEADSEV ELLTTSSDTD  180
LLLEDSAPSD FKYDAPGRRS FRGCGQINYA YFDSPTVSVA DLSCASDQNR VVPDPNPPPP  240
QSHRRLRRSH SGPAGSFNKP AIRISSCTHR ASPSSDEDKP EVPPRVPIPP RPAKPDYRRW  300
SAEVTSNTYS DEDRPPKVPP REPLSRSNSR TPSPKSLPSY LNGVMPPTQS FAPDPKYVSS  360
KALQRQSSEG SANKVPCILP IIENGKKVSS THYYLLPERP PYLDKYEKYF KEAEETNPST  420
QIQPLPAACG MASATEKLAS RMKIDMGSHG KRKHLSYVVS P                      461
```

The above two murine sequences were obtained from the Gene Bank database, Accession #BC005546

Human Mig-6 DNA coding sequence
(SEQ ID NO: 17)
(including an italicized, underscored stop codon which is not counted in the nt number)

```
atg tca ata gca gga gtt gct gct cag gag atc aga gtc cca tta aaa     48
act gga ttt cta cat aat ggc cga gcc atg ggg aat atg agg aag acc     96
tac tgg agc agt cgc agt gag ttt aaa aac aac ttt tta aat att gac    144
ccg ata acc atg gcc tac agt ctg aac tct tct gct cag gag cgc cta    192
ata cca ctt ggg cat gct tcc aaa tct gct ccg atg aat ggc cac tgc    240
ttt gca gaa aat ggt cca tct caa aag tcc agc ttg ccc cct ctt ctt    288
att ccc cca agt gaa aac ttg gga cca cat gaa gag gat caa gtt gta    336
tgt ggt ttt aag aaa ctc aca gtg aat ggg gtt tgt gct tcc acc cct    384
cca ctg aca ccc ata aaa aac tcc cct tcc ctt ttc ccc tgt gcc cct    432
ctt tgt gaa cgg ggt tct agg cct ctt cca ccg ttg cca atc tct gaa    480
gcc ctc tct ctg gat gac aca gac tgt gag gtg gaa ttc cta act agc    528
tca gat aca gac ttc ctt tta gaa gac tct aca ctt tct gat ttc aaa    576
tat gat gtt cct ggc agg cga agc ttc cgt ggg tgt gga caa atc aac    624
tat gca tat ttt gat acc cca gct gtt tct gca gca gat ctc agc tat    672
gtg tct gac caa aat gga ggt gtc cca gat cca aat cct cct cca cct    720
```

-continued

```
cag acc cac cga aga tta aga agg tct cat tcg gga cca gct ggc tcc    768 ttt aac aag cca gcc ata agg ata tcc aac tgt tgt ata cac aga gct    816 tct cct aac tcc gat gaa gac aaa cct gag gtt ccc ccc aga gtt ccc    864 ata cct cct aga cca gta aag cca gat tat aga aga tgg tca gca gaa    912 gtt act tcg agc acc tat agt gat gaa gac agg cct ccc aaa gta ccg    960 cca aga gaa cct ttg tca ccg agt aac tcg cgc aca ccg agt ccc aaa   1008 agc ctt ccg tct tac ctc aat ggg gtc atg ccc ccg aca cag agc ttt   1056 gcc cct gat ccc aag tat gtc agc agc aaa gca ctg caa aga cag aac   1104 agc gaa gga tct gcc agt aag gtt cct tgc att ctg ccc att att gaa   1152 aat ggg aag aag gtt agt tca aca cat tat tac cta cta cct gaa cga   1200 cca cca tac ctg gac aaa tat gaa aaa ttt ttt agg gaa gca gaa gaa   1248 aca aat gga ggc gcc caa atc cag cca tta cct gct gac tgc ggt ata   1296 tct tca gcc aca gaa aag cca gac tca aaa aca aaa atg gat ctg ggt   1344 ggc cac gtg aag cgt aaa cat tta tcc tat gtg gtt tct cct tag       1386
```

Human Mig-6 Amino Acid Sequence (SEQ ID NO: 18)

```
MSIAGVAAQE IRVPLKTGFL HNGRAMGNMR KTYWSSRSEF KNNFLNIDPI TMAYSLNSSA   60

QERLIPLGHA SKSAPMNGHC FAENGPSQKS SLPPLLIPPS ENLGPHEEDQ WCGFKKLTV   120

NGVCASTPPL TPIKNSPSLF PCAPLCERGS RPLPPLPISE ALSLDDTDCE VEFLTSSDTD  180

FLLEDSTLSD FKYDVPGRRS FRGCGQINYA YFDTPAVSAA DLSYVSDQNG GVPDPNPPPP  240

QTHRRLRRSH SGPAGSFNKP AIRISNCCIH RASPNSDEDK PEVPPRVPIP PRPVKPDYRR  300

WSAEVTSSTY SDEDRPPKVP PREPLSPSNS RTPSPKSLPS YLNGVMPPTQ SFAPDPKYVS  360

SKALQRQNSE GSASKVPCIL PIIENGKKVS STHYYLLPER PPYLDKYEKF FREAEETNGG  420

AQIQPLPADC GISSATEKPD SKTKMDLGGH VKRKHLSYVV SP                    462
```

The above two human sequences were obtained from the Gene Bank database, Accession #NM_018948

PGK-Neo is a hybrid gene consisting of the phosphoglycerate kinase I promoter driving the neomycin phosphotransferase gene (resulting in neomycin resistance). This is a widely used cassette employed as a selectable marker for homologous recombination in embryonic stem ES cells.

For embryonic stem (ES) cells, an ES cell line may be employed. ES cells are typically selected due to their ability to integrate into and become part of the germ line of a developing embryo so as to create germ line transmission of the knockout construct. Thus, any ES cell line that is believed to have this capability is suitable for use herein. Thus, examples of suitable ES cell lines to be used according to the invention are the murine ES cell lines GS1-1 (previously BWE4) (Incyte Genomics, Inc. Palo Alto, Calif. USA) and R1 (Lunenfeld Research Institute, Mt. Sinai Hospital, Toronto, Ontario, Canada. Other murine ES cell lines known to the skilled man in the art may also be used. As an alternative to ES cells, embryonic cells may be obtained freshly from a host, e.g. mouse, rat, guinea pig, etc.

ES or embryonic cells are typically grown on an appropriate fibroblast-feeder layer or in the presence of appropriate growth factors, such as leukemia inhibiting factor (LIF). When ES cells have been transformed, they are used to produce transgenic animals. After transformation, the cells are plated onto a feeder layer in an appropriate medium. Cells comprising the construct may be detected by employing a selective medium, in the present case, medium with neomycin (or G418). After sufficient time has passed for colonies to grow, colonies are picked and analyzed for the occurrence of homologous recombination/integration of the knockout construct. Those colonies that are positive may then be used for embryo manipulation and blastocyst injection.

Methods used for cell culture and preparation for DNA insertion are well-known in the art, for example, as set forth in any of the following references: Robertson, E J, In: *Teratocarcinomas and Embryonic Stein Cells: A Practical Approach*, E J Robertson, ed. IRL Press, Washington, D.C. (1987); Bradley et al., *Current Topics in Devel. Biol.* 20:357-371 (1986); Hogan et al., *Manipulating the Mouse Embryo: A Laboratory Manual*, Cold Spring Harbor Laboratory Press, Cold Spring Harbor, N.Y. (1986); and Talts, J F et al., *Meth. Mol. Biol.* 129:153-187 (1999).

Each knockout construct DNA to be inserted into the cell must first be linearized if the knockout construct has been inserted into a vector. Linearization is accomplished by digesting the DNA with a suitable restriction endonuclease selected to cut only within the vector sequence and not within the knockout construct sequence. Insertion of the knockout construct into ES cells is accomplished using a variety of well-known methods including for example, electroporation, microinjection, and calcium phosphate treatment In a preferred embodiment, the method of insertion is electroporation. See references cited above. If the cells are to be electroporated, the ES cells and knockout construct DNA are exposed to an electric pulse using an electroporation machine and following the manufacturer's guidelines for use. After electroporation, the cells are allowed to recover under suitable incubation conditions. The cells are then screened for the presence of the knockout construct.

Screening for the presence of the knockout construct can be done using a variety of methods. Where the selection marker gene is an antibiotic resistance gene, the cells are cultured in the presence of an otherwise lethal concentration of antibiotic. Those cells that survive have presumably integrated the knockout construct. If the selection marker gene is other than an antibiotic resistance gene, a Southern blot of the ES cell genomic DNA can be probed with a sequence of DNA designed to hybridize only to the marker sequence. Finally, if a marker gene is a gene that encodes an enzyme whose activity can be detected, such as β-galactosidase, the enzyme substrate can be added to the cells under suitable conditions, and the enzymatic activity analyzed.

To properly identify and confirm those cells with proper integration of the knockout construct, the DNA can be extracted from the cells using standard methods such as those described in Sambrook, J. et al., *Molecular Cloning: A Laboratory Manual*, 3$^{rd}$ Edition, Cold Spring Harbor Press, Cold Spring Harbor, N.Y., 2001. Brent, R et al., *Current Protocols in Molecular Biology*, John Wiley & Sons, Inc., 2003; Ausubel, F M et al., *Short Protocols in Molecular Biology*, 5$^{th}$ edition, Current Protocols, 2002). The DNA may then be probed on a Southern blot with a probe or probes designed to hybridize in a specific pattern to genomic DNA from, in this case, the ES cells digested with (a) particular restriction enzyme(s). Alternatively, or additionally, the genomic DNA can be amplified by PCR with probes specifically designed to amplify DNA fragments of a particular size and sequence(see Examples), where only those cells containing the knockout construct in the proper position will generate DNA fragments of the proper size.

Injection/Implantation of Embryos

After suitable ES cells containing the knockout construct in the proper location have been identified, the cells are inserted into an embryo. Insertion may be accomplished in a variety of ways, however a preferred method is by microinjection. For microinjection, about 10-30 cells are collected into a micropipette and injected into embryos that are at the proper stage of development to integrate the ES cell into the developing embryo. Blastocysts are typically obtained from 4 to 6 week old superovulated females.

The suitable developmental stage for the embryo is species-dependent, about 3.5 day old embryos (blastocysts) in mice. These embryos are obtained by perfusing the uterus of pregnant females using conventional methods. While any embryo of the right age/stage of development may be used, it may be preferable to use male embryos from strains of mice whose coat color is different from the coat color of the ES cell donor (or strain of origin. This facilitates screening for the presence of the knockout construct in mice with mosaic coat color (indicative of incorporation of the ES cell into the developing embryo).

The selected ES cells are trypsinized, and injected into the blastocoel of the blastocyst. After injection, the blastocysts are returned to the uterine horns of pseudopregnant females. While any foster mother may be used, those preferred are selected for their past breeding ability and tendency to care well for their young. Preferred foster mothers are used when about 2-3 days pseudo-pregnant. Pregnancies are allowed to proceed to term and birth of pups. The resulting litters are screened for mutant cells comprising the construct.

Screening for Presence of Knockout Genes in the Non-Human Mammal

If a coat color selection strategy has been employed, offspring born to the foster mother may be screened initially for mosaic coat color. In addition, or as an alternative, DNA taken from e.g., tail tissue of the offspring may be screened for the presence of the knockout construct using Southern blots and/or PCR as described herein. Another suitable way of screening for the presence of knockout genes is immunoprecipitation Offspring that are shown to carry the knockout construct in their germ line are then intercrossed to generate homozygous knockout animals. If it is unclear whether the offspring has the KO gene in its germ line, they can be crossed with a parental or other strain and the offspring screened for heterozygosity. The heterozygotes are identified by Southern blots and/or PCR amplification of the DNA, as set forth above. The heterozygotes can then be intercrossed to generate homozygous knockout offspring. Probes to screen the Southern blots can be designed as set forth in herein.

Other means of identifying and characterizing the knockout offspring are available. For example, Northern blots can be used to probe the mRNA from the mouse for the presence or absence of transcripts encoding either the gene knocked out, the selectable marker gene, or both. Western blots can be used to assess the level of expression of the knocked out gene in various tissues of these offspring by probing the employing antibody against the Mig-6 protein In situ analysis, such as fixing tissue or blood cells from the knockout mouse, and labelling with antibody and/or flow cytometric analysis of various cells from the offspring may be conducted. This method works well with suitable anti-Mig-6 antibodies.

Uses of Knockout Non-Human Mammals

The knockout mice of this invention and cells obtained therefrom have a variety of uses described above. A preferred use of the KO mouse and its progeny is as a model for development of osteoarthritis. Another use of the present KO mouse and its progeny is as a model that exhibits enhanced tumorigenesis.

The present KO mouse/mice may used to screen an agent for activity in preventing, inhibiting, alleviating or reversing symptoms associated with osteoarthritis or in preventing, delaying tumorigenesis or treating tumors that develop. Such an agent may be a chemical compound, a drug, a macromolecule such as a nucleic acid (DNA, RNA, PNA), a polypeptide or fragments thereof; an antibody or fragments thereof; a peptide, such as an oligopeptide; or a mixture of any of the above. Also, the agent may be a mixture of agents obtained from natural sources, such as microorganisms, plants or animals.

Screening a series of agents for its activity as a potentially useful drug involves administering the agent over a range of doses to the Mig-6 KO mice, and evaluating the status of the mice with respect to the development of joint abnormalities characteristic of osteoarthritis or development or progression of tumors Conditional Mig-6 Knockout/Rescue Mice As noted herein, early deaths of the Mig-6 null mice (presumably due primarily to severe joint disease) makes it difficult to investigate the role of this gene in other tissues or organs such as lung, liver or kidney (that express moderate to high levels of Mig-6 protein). Since neoplasia of lung and other tissues were observed in conventional Mig-6 knockout mice (see Examples IV-VIII), the production of conditional knockout mice will allow detailed investigation of the role of Mig-6 in particular tissues and organs.

The present invention provides an approach to conditionally delete Mig-6 in a specific organ or tissue like lung or kidney by crossing Mig-6 conditional knockout mice with mice that carry a tissue-specific Cre transgene. This approach avoids the problems of early death, enabling analysis of the role of Mig-6 in those organs over a prolonged period (which period is critical for tumor development in the absence of a tumor suppressor gene).

Creation of conditional KO mice is well-known in the art. See, for example, the following published U.S. patent applications: 2004/0045043, 2004/0241851, 2006/0064769, and references cited therein. For applications of this approach to tumor-related studies, see, for example, Jackson, E L et al., *Genes Devel.* 15:3243-48 (2001); Forrester, E et al., *Cancer Res.* 65:2296-2302 (2005)).

The approach of the present invention described below is novel because it uses human Mig-6 to rescue mouse Mig-6 under the supposition that human Mig-6 functions in a manner similar enough to murine Mig-6 for such rescue to occur.

Figure 13:
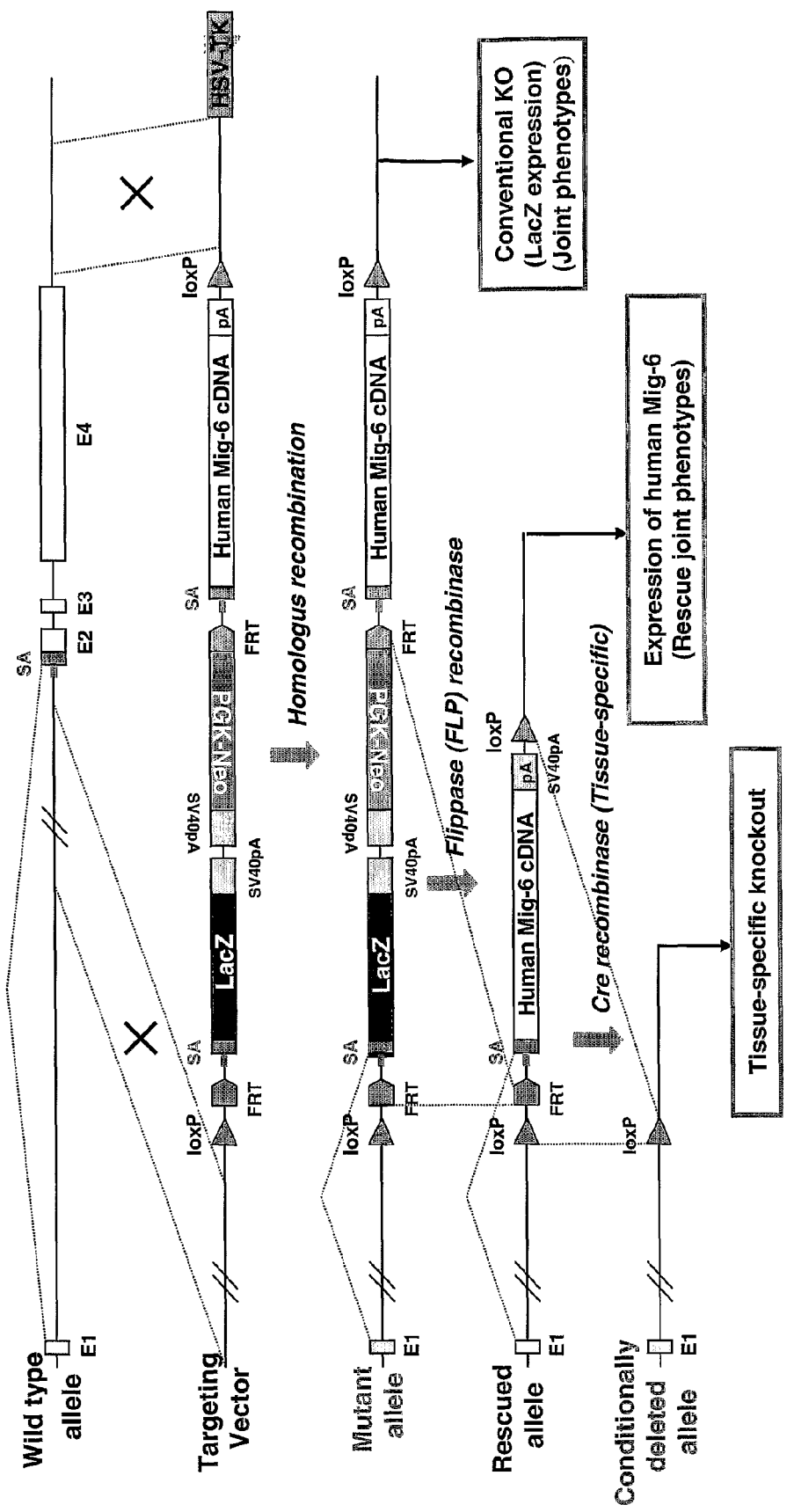
FIG. 13 shows a strategy for generating animals of a conditional Mig-6 knockout/rescue mouse strain carrying LacZ reporter and for obtaining mice with a Mig-6 gene that can be conditionally deleted by crossing with animals carrying a tissue-specific Cre recombinase. The following abbreviations are used in this Figure: E1-E4—exons 1-4 in the genomic structure of Mig-6; FRT-FLP recombinase target sequence; SA-splice acceptor; SV40pA-SV40 polyA region; pA-polyA region linked to of Mig-6 cDNA.

The present approach to conditional Mig-6 KO technology is illustrated in FIG. 13. The "Wild type" allele at the top depicts the normal gene structure of Mig-6 (genomic DNA) which comprises four exons (E1-E4). E2 through E4 include the entire coding region of Mig-6. Other abbreviations are found in the description of FIG. 13.

The best-known site-specific DNA recombinase is the Cre recombinase, a product of λ or P1 phages in *E. coli* and which is used in combination with the loxP recognition site. Cre recombinase of the P1 bacteriophage belongs to an integrase family of site-specific recombinases that is expressed in mammalian and other eukaryotic cell types (Saur et al. (1988) *Proc. Natl. Acad. Sci. USA* 85:5166-5170, (1989) *Nuc. Acid. Res.* 17:147-161, (1990) *New Biol.* 2:441-449). Cre recombinase is a 34 kDa protein that catalyzes recombination between two of its recognition sites called loxP. The loxP site is a 34 base pair consensus sequence consisting of a core spacer sequence of 8 base pairs and two flanking 13 base pair palindromic sequences. One of the key advantages to this system is that there is no need for additional co-factors or sequence elements for efficient recombination regardless of cellular environment. Recombination occurs within the spacer area of the loxP sites. The post-recombination loxP sites are formed from the two complementary halves of the pre-recombination sites. The result of the Cre recombinase-mediated recombination depends on the location and orientation of the loxP sites. When an intervening sequence is flanked by similarly oriented loxP sites, as in the present invention, Cre recombinase activity results in excision. Cre/loxP recombination can be used at a high efficiency to excise a transgene in vivo (Orban et al. (1992) *Proc. Natl. Acad. Sci. USA* 89: 6861-6865). See also, Nagy A., 2000, *Cre recombinase: the universal reagent for genome tailoring, Genesis* 26:99-109; Lomeli H et al., 2000, *Genesis* 26:116-7; Hardouin N and Nagy A 2000, *Genesis* 26:245-52). This system has also been used for tissue-specific expression/excision: prostate (Maddison L A et al., 2000, *Genesis* 26:154-6); hepatocytes (Imai T et al., 2000, *Genesis* 26:147-8; Kellendonk C et al., 2000, *Genesis* 26:151-3); differentiating chondrocytes (Ovchinnikov D A et al., 2000, *Genesis* 26:145-6); pancreas (Gannon M, et al., 2000, *Genesis* 26:139-42 and 143-4); muscle (Miwa T et al., 2000, *Genesis* 26:136-8); epidermis (Berton T R et al. 2000, *Genesis* 26:160-1); brain, nervous system and retina (Dragatsis I et al., 2000, *Genesis* 26:133-5; Furuta Y et al., 2000, *Genesis* 26:130-2; Niwa-Kawakita M et al., 2000, *Genesis* 26:127-9).

More recently, the FLP-FRT system (see, for example, Dymecki, S, 1996, *Proc. Nat'l. Acad. Sci.* 93:6191-6) has become more commonly used, primarily in work with mice. It is similar to the Cre-Lox system in many ways, involving the use of "flippase" (FLP) recombinase, derived from the yeast *Saccharomyces cerevisiae* and native to the 2 micron plasmid resident in these yeast cells (Utomo A R et al., 1999. *Nat Biotechnol* 17:1091-96.). In lieu of loxP sites, FLP recognizes a pair of FLP recombinase target ("FRT") sequences flanking the genomic region of interest. As with loxP sites, orientation of the FRT sequences dictates inversion or deletion events in the presence of FLP recombinase.

Both Cre and FLP alter the arrangement of DNA sequences in very specific ways. The FLP recombinase is active at a particular 34 base pair DNA sequence, termed the FRT (FLP recombinase target) sequence. When two FRT sites are present, the FLP enzyme creates double-stranded DNA breaks, exchanges the ends of the first FRT with those of the second target sequence, and then re-attaches the exchanged strands. This process leads to inversion or deletion of the DNA which lies between the two sites. Whether an inversion or deletion occurs depends on the orientation of the FRT sites: if the sites are in the same orientation, the intervening DNA is deleted, but if the sites are opposite in orientation, the DNA is inverted. The FLP recombinase is used as a negative selectable marker for experiments to replace genes by homologous recombination.

As described in FIG. 13, to construct the indicated targeting vectors, a 5 kb genomic DNA fragment upstream of E2 and a 3 kb genomic fragment downstream of E4 are inserted into pPNT vector. A cassette which carries lacZ reporter gene, PGK-Neo and human Mig-6 cDNA flanked by loxP and FRT sequences is inserted between the two genomic fragments. The SA ("splice acceptor") site contains fragments of intron 1 and exon 2 and serve as a splicing acceptor after homologous recombination.

ES clones are established by electroporation of linearized targeting vector and selection in neomycin. HSV-TK is used for negative selection. The "mutant allele" shows the genomic structure after homologous recombination. Mice homozygous at this step display the same phenotypes as conventional Mig-6 knockout mice, except that the lacZ reporter replaces Mig-6 expression and can be visualized by routine methods such as staining with 5-bromo-4-chloro-2-indolyl-β-D galactoside ("Xgal").

The derived knockout mouse is crossed with a transgenic mouse carrying Flippase (FLP) recombinase which recognizes FRT sequences. At this stage ("rescued allele"), the lacZ reporter and PGK-Neo are deleted, and the human Mig-6 is transcribed. The human Mig-6 rescues the phenotypes present in the conventional Mig-6 knockout mice. The mouse produced in this step is further crossed with a transgenic mouse carrying Cre recombinase that is expressed in a tissue-specific manner and recognizes loxP sequences. This allows investigation of any tissue-specific effects of Mig-6.

Screening of Candidate Agents In Vivo

Agents can be screened for their ability to mitigate an undesirable phenotype (e.g., a symptom) associated with absent or reduced Mig-6 expression or function. In a preferred embodiment, screening of candidate agents is performed in vivo in KO animal of this invention. A KO animal suitable for use in screening assays includes any animal having an alteration in Mig-6 expression as a result of homozygous or heterozygous knockout of the Mig-6 gene.

The candidate agent is administered to the non-human, Mig-6 KO animal and the effects of the candidate agent determined. The candidate agent can be administered in any manner desired and/or appropriate for delivery of the agent in order to effect a desired result. For example, the candidate agent can be administered by injection or infusion, e.g., intravenously, intramuscularly, subcutaneously, or directly into the tissue in which the desired affect is to be achieved, orally, or by any other desired route. Normally, the in vivo screen will involve a number of animals receiving varying amounts and concentrations of the candidate agent (ranging from negative controls to an amount of agent that approaches an upper limit of tolerable doses), and may include delivery of the agent in any of a number of different formulations. The agents can be administered singly or can be in combinations of two or more agents, especially where administration of a combination of agents may result in a synergistic effect. The effect of the test agent upon the KO animal can be monitored by assessing a biological function as appropriate or by assessing a phenotype associated with the loss of Mig-6 function. For example, the effect of the candidate agent can be assessed by determining levels of bony outgrowth and articular cartilage degradation produced in the KO mouse relative to the levels produced in the untreated Mig-6 KOK mouse and/or treat or untreated wildtype mice. Methods for assaying bony outgrowth and articular cartilage degradation are well known in the art. Where the candidate agent affects a Mig-6-associated phenotype, in a desired manner, the candidate agent is identified as an agent suitable for use in therapy of an Mig-6-associated disorder.

The test agents identified by the present methods to have the desired pharmacological activity may be administered in a physiologically acceptable carrier to a host for treatment of a condition attributable to a defect in Mig-6 function (e.g., osteoarthritis and various types of cancer).

Other Functions of Mia-6

The Mig-6 gene expression is significantly up-regulated by SRC-1 and progesterone receptor in the murine uterus. Realtime RT-PCR and in situ hybridization studies of Mig-6 regulation by SRC-1 and progesterone receptor showed that progesterone induces mig-6 synthesis in uterine stromal cells of ovariectomized wild type mice, but not in progesterone receptor KO mice or SRC-1$^{-/-}$ null mice. Treatment (40 hrs) of ovariectomized mice with estrogen and progesterone strongly induces Mig-6 expression in the stroma cells 40 hr. Mig-6 is also expressed at relatively high levels in the decidual regions early in pregnancy. The ability the uterus to undergo a hormonally induced decidual reaction is significantly enhanced in the Mig-6 KO mice of the present invention, Mig-6 thus appears to exert anti-proliferative effects in the decidualization reaction in mice.

Mig-6 has been found to play a role in the molecular pathophysiology of ischemic injury. Cardiac ischemia (or hypoxia of cardiomyocytes in vitro) deprives these cells of oxygen, triggering cell death (=myocardial infarction) mediated by a stress response program induced by ischemia or hypoxia. Expression of the Mig-6 protein, a 50-kDa cytosolic adapter protein which suppresses signaling from receptor Tyr kinases of the EGF receptor/ErbB family, rapidly stimulates cardiomyocyte death coincident with reduced Akt and ERK signaling. Indeed, Mig-6 levels increase in myocardial ischemic injury and infarction. Hypoxia/reoxygenation of cultured cardiomyocytes induces Mig-6 mRNA and protein. Endogenous Mig-6 reduces Akt and ERK signaling and is required for maximal hypoxia-induced cardiomyocyte death.

Having now generally described the invention, the same will be more readily understood through reference to the following examples which are provided by way of illustration, and are not intended to be limiting of the present invention, unless specified.

EXAMPLE I

Mig-6 Knockout Mice: Materials and Methods

Mice and Genotyping.

To generate Mig-6 knockout mice, the present inventors constructed a Mig-6 targeting vector or knockout vector (FIG. 1A) by inserting a 5 kb genomic fragment upstream of exon 2 (designated e2) and a 3 kb genomic fragment downstream of exon 4 (designated e4) into the pPNT vector (Tybulewicz, V et al., (1991) Cell 65:1153-63), respectively 5' to and 3' to the PGK-NEO cassette.

As shown in FIG. 1A, this knockout vector or "targeting vector" includes the following components (in the 5'-3' direction):

(1) The 5'-homologous recombination sequence derived from mouse Mig-6 genomic DNA; this is a ~5-kb genomic fragment mostly upstream of exon 2 (though it includes a short sequence from exon 2). This fragment has the following sequence [SEQ ID NO:19]. The bold/ underscored 3' sequence corresponds to nt's from exon 2.

```
AGGTCATCTA GTGGAGGCAA GAACACACAA ACCATCCTTT CTTTGCATCC TTTTGGACAG

CATTTATGAA ATATTTGCTG AAGCTATCAC ATCTTACTTG ATTCCATGCA TGAGCACTGT

AGTTGTGTTT TATTTTAGAA GTCATTCATG CAGCTAATAT AAAGGCGAGT TCTGCTTTTC

TATGGTAAAC TTATAACAAA GAAGTTTCCT TAGCCTGGCT CCCTTCTTTC CTTAACCCCA

AATCATAGCT TTTAAAATTA AATCTGAAAA ACTTTGAATT CAGGCCTTTG CTCTTGAAAT

ATCTGTGCAA ACGCCCTTTT GCTTTCAGTA AATAAGTGTA GATTATATCA CCTGCTTGAT

TCAAAGACAC AGAAGAGTCT TTGCTGCGTT TAACAGTTTG TTACCTTAAC TTCCACAAAC

CAGGAAGACA CATGCTCGCT ATTTACAGCC AAAATGTGTA AGACATTGAC TAGAAGTATG

ATGGATCCCA TGATTTTTAG ATCCTCCTGT GTAACAGGAT AATGCTGAGT GCAGGTAGAT

GCTAAGTCAT TTTTCTCCGT TATTAATTTA AGTCCACAAC ACAGCAAATA AAACTGATTT

CCATTTCCTC TCATTTTCTC GGCGAGCATA GGAAGTAGTA TATTTGAGGA AGATCCAAAG

TAATGAAAGG TGGCAACGTT TCTAATCGGT GTCTTCCGAT AAACTTGGCT CTATAGTGAA

GTTGTCTTCC CTGATTATGG AAGTAGCTAG GTAGGCAATT GTTAAACGCA GCTGGAAAGA
```

-continued

```
CCATTTATCA CTCTGAATAA ACAGAAATCA GGTTCTAGAA CCAGATTGAA AGAAGGAAAT

TACATCACAC TCTTAAATAA GGAAGCACTG GGCAGAACTG GATGAGTTGT AAGACAAAAA

TGTGCCCCTC CTCCTCTCAT GGACTGCTCC TGAGATGTAT TAATAAGATC TTGTGGCAAG

GTAAGCATAT CTAGGTTACT GCCTTAAGGT AGCCTAGCTT TGTGTGTTAA AGCAGTTTCA

AAGTAAGTAT TTTCAAGATA AAGACATGTG AGTTCACCTT AGAAAGTGTG CAGTGTGCTA

TTGGTATATT GTGACTTTTT TATTTTTAAA GTGTCAATAA AACAAAGATA GATAGATTAC

AAGCCCAAAG GAACAGTATG TAAGAAAAGG TGAAAAGTCT GTAGTAAGAA GCCATTGAGA

AAGCCACGCC AGCAGCCATT GATGCTGACC TTTTACTCAG CCACACACTG TCACTGAGGA

CCCAGAAGGT GAACTCGGGA TATTCTAAAT GTGTTAGGTT ATTACAGGCC TAACTTACAT

ACAGTACATT CAGAGTTGAT CCCTGAACAA ATCTGTGCTT TTCCCTTAGC TTTCCTCTTC

AGCCTGGGGA GAATCTTACA TAATTACATT TTAAAACATG AGATGGCTAT TTTCTCAGTT

CACTTAATAT GATCTACAGG GGGGAGGAAA TGTCAGGCAC CAGTCCTAGA TTTGGAGGGT

AGGAGGGGAA CCTGGCGTAG CACAGAATAG CTAGACTGGC CCTGGATTTT AATAACAGGA

GGGGCTTGTT GAAGGAGCAC AGTGTGAGAA CAAGCCTTAA AGCTCAAAGC AGCTAGAGCT

GAACAGGGCA GGTTAGGGAA AGGCCATTGT GAGGTCTTTT GTGCCAGCTG AGGCGCTTTT

AGAGGCTTTT ACAGGTTCTT TTGGGGGTGG CAATTAAGGA ATATTGATTT GATCCTGTTG

GCTGTAGTAT GGTTTAAATA TCTTCAGACT AAAAATTGGA ACCAATAGGA GAAGGAAGAG

AGTTTTGAGA AGAAGTTTAA AAACTTTGTA TGGATGTTGG CAGTTGAATG TATATTGGCC

TTAACTCAGG CTCACAGTGG TAGGTACCTC AGGAAGTATG ATCCTCTTGG ATCAAGAAAG

GGTGGGAGGT AAGTTAAGAG ACCCAAAGAA TCGGGTTTGG AACTTGTGAG ATACCAGAGG

CCCATCCAAG TGGAAAGATA ATCACCAGAC AGACAATAAG AAATGCACAG TGGAAGTGGA

AGTCAGACTG CACGTACCTC CTTAGGAACT GTCTGTGGAT TTGAAGCCAT AGAAATGAAT

TAAAAGATTT TAAGAGCAAA ATCTTAAAGT TAAAATATAG TGCAATTAGC AGAAATGAGG

TACTGGTATT TAACTACATT TTGGTCACTT CACATTAAAA TTGTTTTATG ATTATGTAAA

TTGTTATACT GAAGGTTATT TGGGTCCTGG TTTACACAGT GAACCTGTAT CGACATTCAT

TTTGATCTTG GCTTTCATAA TAGAATACCA TATTGTACTT TTAAATATTG ACACTCATAC

ATAAATGTAT CTTTGCAGTT AGTTTCTTTA TGAATTGAAA AGTAGAGCTA GTTTTACAGT

TATGAGGACT TGGATACAAT TGTAAACACT GCAGCATTAG TTGAATTTTA CTTGAGCAAA

CTGTGTTGTT TTATTGGCTA GAGTGATTTC TCTGCCTCCA CCAGGATTAT ACAACCTGAA

TGCTGGCTTG GCTTTTTTG TCTTGTGAGG TAGGAGACTT CCAAACAGTT TTCTAACATA

ACCTTAGTTT AACATCAGGA GGGATGAGAG AGTGTATGTG TATCTAAGCC TTAAACCTGG

GGCATGTTGC TCTTTTGAGT TTTACAGCCT GAAGTTATTT TCCAAACGAT GAGAGCACAG

CAGTTATATT GCCCTCTTTG CTTCTGCCAT GCAAGCAAGT AGGAAGTTCA GATAGTTTCA

TAACATGGCC CATTCACAAT TCCCCATTGA AATTTAGAGG CAGGTCACCT TCTATGAATA

CACAAAGACA ACTATTGTGG TCAGAAGTGA GCTGGCTTAG TGAACACAAT TCTTTTTATA

CTAAAAAAAA AAAATTTCCT TAAGAAAGCT AACAAGTAGG TGATGGAACA ATGAATAAAA

AATAACTTTT TCTAAAACAT ATAAATAATT TTAAGTGACC ACTGAAGTGT AAGTTTAGGA

TTCCAAGGCA ACTTGAGCAG AGGCGATAGT TACACAATCA CTCTGTTGAA AGCTAAGATG

TAGATGGCAC TGGGAGGCTG ACACAGTAAT TACTAGTAGT ATTTGTTGGC TGGCCTACAG

GTGGGGGCTG GGCCTCCCTC GTCCCCCGCA GCATTGTCCT GTAATCGGGA TGAACCATCT

TCCAACGTGT GCTTTCAAAC CACTTAACCA CCACAGTCGT CCTCCCATCT CGCCTGCCTT
```

```
TCATTTTCAT ATTACACAGA TCCTTTCCCT GTAGTCTCTC AGTGTTTGTG ACTATTTAGA

AAGGGCTTGA TACACCCTGG CTAAGTATAC ACTGGGAGAG GCTAGCCTCT TTAAAAATGT

GTTTTTTAAA TTACTCAATG GTAAATAACA CATCCGTTTT ATTTCAGTAA TCTAAAAAAC

CAAGACTCAA AGACCTAATA CTAAGGTTCC TTAAGTGACG GAGAGACTGG TTTTTCAAAA

CAAGGTTTGA CTCTTTGAAA TAAAATAACT GCCTTGTGTA TTAAAACAGC TGCTTTTGTA

AACATCTATG GGGTATTTTT TTAGATTAGC TTAAAAATGT AAGAACCCCT ATGCCTTCCA

CATAGTTTAC CTTTGGCAGA CTTACTGAGC CAGGTCCCTG TGGTTAAAAG GTACTTAGGA

CCCTCAGCCA CTTGTTCTGA AGCCATAGTT CACTGGGCCC AGATTTGTAA GTAGTACATG

TTTAGTTGCT GATCATTTTA ATAAGAAGGT CCATCTGCGT AGCTCCTTCA GCACAGGGGT

CCTAGTCCCG CACTAGCACT TGGTAGGTCT GCAAGTATTT AATGGCAGAG TTGTGTAGAC

AATGTGTGTG GAGAACTCAA AGGGGTCTGT GTTCTGGGCA GCCAGCAGAT AACATCCTGC

TGTCTAAAGG CGAAAAGGCC CAGCTTCCTA AATGCTCGTG CCTATCTGAA GCCAGCAGAG

TTGGTGGGTT TTAGCATCTG CAGAGTACTG AATCAAAAC AGAAAATTAG AATGCGCCTG

TGAGAACTCC AGGCCGGTAA CATCTGATAC AAGGGGATTT CTAAAATTAA GGAACTACTA

GTTTAAGAAA AATATATTTT GCTTTTGTAG TCCATGCCTT ATAGGGAGGA GGACATGAAT

TACTGCGTAT TTCACAAAGG AGAACACAAA CAATGTCCCT TAAGTTTGTC TTTGAAAGGA

AGGAAGCTAG CCAAAGCTGA CACTGAAGCC AGTAATCTTG CAGAACTTGA TTTTTACAAG

ATGATAGAAA TTTGTATCCG CATATGTGAC TGTATATTTC TTGAGCAAGT AATAGCTGGA

GAATATGTCT TCTGTGACCA ACCCCGAAAT ACAGAGTCCA AATGAATGTT AGGCTGTGGG

GAGGTGGGTT TCAGTGCTGG AGACTCTCCT GAGTGGGCTC TAGTGAATGA CAGCTCAGCC

TGTGTGGAGC ACGGTACTTT CTAAAATTAC TTAGGTTTGT TTGTTGTTTT CAGGGTGGGG

GATCAGTGAG GGTAAGACAG GACTTGTTAT GTAGTCCAAG CAGGCCTTGA ACCCTACCTG

CCTCAGCCTC GAAAGAGCTG GGATTACCAT GCCTAGCTTG AAATTCCTTT TTAAGCCTGG

GAAAAATGGG TAGTATCCAC TGCGCTTCCT TCCTGGTAGA GCCATGCCAT AGAAAGTCAG

TTTAGTGGGC TGAAGGGGGT TTGTGTGCTT TGGAAAGCAG TTGTGATTTG TTGAGCAACT

GGTAAGCTCT GCAGCAAGGG TTGGCTTTCC TGGCAATTGA TTCTTTCTCA TTCTGTGAAA

AACCTTTCAA GTGTCAAGTT AGTATTTATA AAAACAAAAA TTGTTTTTTG CTGGCCACAT

TTTAAGTATC CTTATAAGAA TTAGAAGAAC GTCTATAACC AAATTTTCCC ATCTCCCTCC

ACCTCTGATT ATTTATGCTA CAATATATAC TATCCGACTT CTGAATTATG TTGTTTATTC

TCTCATTTGT TCTTGATTTC CCCAGGGAAT GAAAGCTACT GGTTGACTTA AAAACACCTG

GGCTTTACAA ATTTGAAGGC A
```

(2) The PGK-neo cassette which comprises the PGK-Neo hybrid gene consisting of the phosphoglycerate kinase I promoter driving the gene (resulting in neomycin resistance). This is a widely used cassette employed as a selectable marker for homologous recombination in embryonic stem ES cells. See, for example, Tybulewicz, V et al., supra). This cassette is flanked by a 5' XhoI restrictions site and a 3' EcoRV restriction site (respectively labeled X and E in FIG. 1A). The sequence of PGK-neo in known in the art (see any cell or molecular biology textbook such as Strachan, T et al., *Human Molecular Genetics*, 3rd ed., Garland Science, 2003) and is publicly available. A cloning vector pPGKneo-I is provided at Gene Bank Accession #AF335419, which includes the sequences of the PGK-1 promoter, the nucleotide (and amino sequence) of neo coding sequence (and its protein product) as well as the lox-P site (which is discussed above). See, also, for example, for the PGK-1 promoter, McBurney M W et al., 1991, *Nucleic Acids Res.* 19:5755-61, and for the neo gene, Colbere-Garapin F et al., *J Mol Biol.* 150:1-14 and Beck E et al., 1982, *Gene* 19:327-36.

(3) The 3'-homologous recombination sequence derived from mouse Mig-6 genomic DNA; this is a ~3-kb genomic fragment downstream of exon 4). This fragment has the following sequence [SEQ ID NO:20].

```
TAGGATCACA TAACCTGGGC ATGGTAGTAC ATGCCCATAA GCCCAGCACT TGGGAGGCAG

AGGCTGGAGA ATCAGGAGTT CAAGGTCATC TTTGGTTACA CATGCATTCG GGGTTTTAGG

CCACATGAAT CCCTGTGAAA GAAAGAGGGG GGGTGGGGGA AGGAAAGGAA AGGAAAGGAA

AGGAAAGGAA GAAAGGAGAG AAATTTTGTG GTAAAATCAA GCCTTTTGTT CTTACCTGCA

ACAACTAAGT AACCTTGGTC CCGTGCTTCT GTGGAAACCT TGAGGGTCAG GGCTGTGCAG

TCCGTAGAAA GGAGCATTCA CTGTACAGAT TTCTTGGGCT TCAGGATTAC TCTGGGCCCT

TTGTGGCCTT TGCTGCTGTT TGTCTGGGAC CTTACTCTCC ACTGCCAGGC ATCACAGAGG

GCCCTGCACA CTGCTGTCTG CTGGGCTGCT GTATCAGAGC TGGTGGCCCT GTGTGTCGGG

TGTTAGATTT GGGAAGAAGA GAGTTTGTGG CGATGTGATT TGGAAGTGTT TAAAAGGTAC

TCGGTAGGCA ACTGAAGGGC ATCTGACCCC TGGAAATGAT GGTCAGAGTT GGAGATAGCG

ATTTGGAAGG TGTGATAGCA GACGAAGGCA AGCCTGTGAG GCCAGGAAGC AGGAAGCAGC

TGGGCACGTT CCAGAAGCTG AAGGCCACGG GCGAGTAGGC TGAGCAGTGG AAAAGGGCAG

TGGGTGCAAC TCAAAAGATC CTAAGTGGGA GAGGAACACG ATGTGATTTG TTTTAGGAAA

GATGACAGTA GCTGCTGTGT GGGGAACATT TCAGAGAAGT GAAATTAGCA GAAACACTAA

AAGCTACAGG CCAGGGCCCA AAACTGGCAC CAGAGTGAAG GGGGGGCGGG GGAGGGGATG

GAGAGACACA TGGCTTTCAG AGTTGTTAGG ATGACAGGCT CCAGCCTGAA AGCAGTCTGC

ACCGCCCTTC TTCCAGAACG GCGGTGGCTC TTGCGAGCTG GAACCGCCTG TGTCCTTGTA

CTAGCACTGA GCATTGCCTG GTACAGGAAG CCATGGTACT TACATTAGTT CCAGCTTCAT

TTCCTTACCT GTTTCTGTGT TTTCCCTTGA ACTTTTGCGA TATACTTTTC ATGGTTTTTT

CTGGTCAAAG AACTGTCCTT GGCGCCCATG CTAATGGCAC ACTGCTAAAA CACCCAGGAG

CCACTTGCCC ACCTATACCT CCCCAGCCGG CACACCAAGC AAGTTGAATT TTTTTTTTCC

AACTTATATG TCTGGGAGTT TTGCCTGTGT ATGTCTGTGC ATTGCATGCA TGCAGTACCT

GGTGCCCACA GGCCCAAAGA TGGCGTGGGA TCATGGTTTC TGACAGCCAT GAGCTGCTAC

ATGGATGCTG GGAACTGAAC TCTGGTTCTC AGGCAGAGCA GCCAGTATTC TTAACGACTA

AGCCATCTTT ACAGCCCTGT GTGATATCTT AGGTAATTAT CAAAATGGGA AGTTGGTATC

TGCACGATCC TTGTATAATG TTTTGTTTAG CTGCAAACTG ATACTTGGTC ATAAAAACTA

GAAACTGATT TGGCCATTCT GTCAGGCATT TTGTAAAAAG CTAGTGGAAC TTTTAAAAAG

CTGTCGTGCA AAGCCATGCA GTGCTCATGG CACTTGATGA GATGGTCCTG ATGCTGGCTG

GCTCCAGAGT AGTCTCCGCT CTTGGCATAG CTGGAGGCTT GAGGTTCCAT ACCTGAAATG

AGAAAAGCC CAAAGACAAG AATGTACATT TTGAATTGAG CTCTAAAGCT CTGAGGTATT

CTTGCCCTAA TATAAGATTT CTTCAAACTA GAAATGGCTT GAGGACTTGT TTTCTTTGTA

GTGTAGGTCA TTTGACAGAA TGTTCTGGCG CCTTTGCGCC CTTCGGTGTG AGTCATGCCA

TTCTTTTGAG GCTCTGAGGG GTGAAGGGGA AGAGAACAGA ATTTGTCTAC ACTGTTGGCC

TCACCTCTTG CTCCCTGTAA CTACACAAAC ATGGTTCAGG CGTGCCTAGC GCTGCTTACT

GTGAGGGTGT GAGCTTGCTC GCCTTCGTCT CACCTGTATG GATTCAACTT CAGGATACTT

GTATCCGAGC CACGGGGAGT CTGCGGCTCC CGCACGTTTA AACAAGCTCC CCTTAGCTTT

CAAGATGTCT ACTTGGAATC TGAAGCAGCA AACATACTTG TGTATGTTTT TCTGTACCTG

AGCTTACATC AGAGCAACCT TGTGACTCAG AAGTCACCGC CCCATGGCAG TAGTGGGGTT

TTGGTAAGGA GTGGGGGGCT GGGGACAGAT GGGAAGGAAT GTACTTCAAG TACTAGTTGG

CACCTGTCTT GGAGCTGCTG TCAGGCTAGA GGCTTAGCCA GCGTGCCTCT TGAATGCTGT

CATCTCTCAC CCTGTAAGTT CAGACACCCG GAACCCCAAG CACAAAAGCC TGTAGCAATT
```

```
ACCCACAGGG ATCCGCGTAT CTGCCCCCCC TCCCCCAAAA TGGAGCTGCT TAGGAATGTG

CACTGCATTC TCTTCACAGA TCCAGGCAGC ACCTTCATTC CTTAGTAAAC ATCTAAACCC

AGGCCTCCCA TGGGTTTCTT CACAGTCATG AGGGTTAGCC AGTGCCTTCC CTAGGGACAG

CATGACTTGT CCGCTCCCCT CTTGTGAAAG GCAGAATGAG TCGTGTCATT CTGGCCTGCA

CCAAGCCTTC CTCTGGCCTA GCCATGGCAC CGCCTCAGGC ACAGCACACA GGAAGCTGTA

CTTTGTTATT CTGAATTCCT GGCTAGCCTC ATGTTCTTGG ATGAACCAG
```

(4) The herpes simplex virus thymidine kinase gene (HSV-TK) which serves as a selectable marker. When the knockout construct is integrated into the chromosome at the site of the normal Mig-6 gene, the HSV TK gene is eliminated by the cellular "recombinase" enzymes, and the cells are not sensitive to the nucleoside analogue ganciclovir. Thus, ES cells improperly transformed, in which homologous recombination has not taken place, will be killed by exposure to ganciclovir, selecting for the desired ES cells. This selectable marker system and the sequence of HSV-TK are well known in the art (and are described in any textbook of molecular or cell biology such as Strachan et al., supra; also, see, for example, Enquist L W, Vande Woude G F et al., 1979, *Gene*. 7:335-42.

While this is an exemplary knockout construct, other constructs that employ different flanking genomic Mig-6 sequences, a different positive selectable marker instead of neo, a different promoter driving neo or another selectable marker, etc. can be use to disrupt the murine Mig-6 gene and achieve the same effects. The negative selectable marker, here HSV-TK, is optional; other well-know negative selectable markers can be used in its place for the same purpose. The present inventors were the first produce a knockout construct/targeting vector to disrupt this gene, and the this invention contemplates any and all analogous or homologous constructs that achieve the same result—a murine Mig-6 KO mouse.

ES clones were established by electroporation of linearized plasmid and selection in neomycin. Positive Mig-6$^{+/-}$ ES clones were screened by PCR and Southern Blot analyses. Two independent clones were used to generate Mig-6 knockout mice. The following primers were used for PCR genotyping:

Forward primer p1: 5'-GACAATTTGAGCAACTTGACTTGG-3' [SEQ ID NO:1] is specific for the wild-type locus;

Reverse primer p2: 5'-GGTTACTTAGTTGTTGCAGGTAAG-3' [SEQ ID NO:2] is shared by both wild type and mutant locus;

Primer p3: 5'-CCTTCTATCGCCTTCTTGACG-3' [SEQ ID NO:3] is derived from PGK-neo cassette and is specific for the mutant locus.

Rag2 null mice (Shinkai, Y et al., (1992) *Cell* 68:855-67 were obtained from Mouse Models of Human Cancer Consortium Repository at the National Cancer Institute. The primers used for genotyping Rag2 mice are those reported in Corazza, N et al., (1999) *J. Exp. Med.* 190:1479-91.

Northern Blot Analysis.

Total RNAs were isolated from mouse tissues by homogenization in TRIzol Reagent (Invitrogen). 20 μg of each RNA sample was used for Northern Blot analyses with mouse Mig-6 cDNA probe and β-actin probe.

RT-PCR Analysis.

First strand cDNA was prepared from 1 μg of each RNA sample using Advantage RT-for-PCR kit (Clontech) and used for PCR amplification. The primers for Mig-6 amplification were:

```
5'-CAGAAGTTACATGGGATGAATGG-3'   [SEQ ID NO: 4]
and

5'-TGAACACAAACTGCGTGTCTCAC-3'.  [SEQ ID NO: 5]
```

The primers for GAPDH amplification were:

```
5'-TCCAGTATGACTCCACTCACG-3'     [SEQ ID NO: 6]
and

5'-ACAACCTGGTCCTCAGTGTAG-3'.    [SEQ ID NO: 7]
```

Primers for Real-time PCR analysis of human MIG-6 are as follows:

```
(1) Forward Primer:
    5'-TCTTCCACCGTTGCCAATC-3'    [SEQ ID NO: 8]
```

This primer is complementary to the human Mig-6 coding sequence from nt 668 to nt 686. Human Mig-6 cDNA nucleotide sequence and encoded amino acid sequence are found in GeneBank accession ID: NM_018948. The human Mig-6 coding sequence is SEQ ID NO:17]

```
(2) Reverse Primer:
5'-TTCCACCTCACAGTCTGTGTCAT-3'   [SEQ ID NO: 9]
```

This primer is complementary to human Mig-6 coding sequence from nt 728 to nt 706 of SEQ ID NO:17.

```
(3) TaqMan Probe:
    5'-CTGAAGCCCTCTCTCT-3'.      [SEQ ID NO: 10]
```

This primer is complementary to human Mig-6 coding sequence from nt 688 to nt 703 of SEQ ID NO:17.

Preparation of Adult Skeleton.

The method for preparing the adult skeleton for analysis is described elsewhere (Selby, P B (1987) *Stain Technology* 62:143-6). Briefly, 4 month old animals were sacrificed, eviscerated and immersed in 2% KOH overnight. The carcasses were rinsed and stained in 1.9% KOH containing 0.04 g/L of Alizarin Red S (Sigma) for two days, and cleared in cleaning solution (400 ml/L of white glycerin, 200 ml/L of benzyl alcohol and 400 ml/L of 70% ethanol).

Histology and Immunohistochemistry (IHC).

Mouse bone tissues were fixed in formalin or 4% paraformaldehyde, followed by decalcification in formic acid bone decalcifier, and then embedded in paraffin. Sections of 5 μm thickness were prepared and stained either with hematoxylin and eosin (H&E), with Mason's trichrome to detect collagens, or with Safranin O to detect proteoglycans. Proliferating cell nuclear antigen (PCNA) or type II collagen was immunohistochemically detected using a mouse monoclonal antibody (mAb) against PCNA (Santa Cruz Biotechnology) or mouse mAb directed against type II collagen (Chemicon International), respectively, using a M.O.M. Kit (for detecting mouse primary antibodies on mouse tissue) and peroxidase detection system (Vector Laboratories). For type II collagen IHC staining, sections were pretreated in Tris-HCl (pH 2.0) containing 1 mg/ml of pepsin for 15 minutes at room temperature. For Von Kossa's staining to detect calcium deposition, sections were prepared from non-decalcified bone tissues.

EXAMPLE II

Early Onset Osteoarthritis in Mig-6 Knockout Mice

Figure 1B:
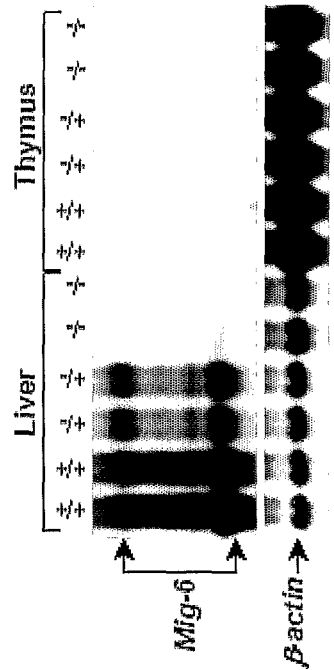

Mig-6 deficient mice were generated by conventional gene targeting technology by replacing the entire coding region of Mig-6 with PGK-Neo cassette/construct (FIG. 1A). The loss of wild type alleles of Mig-6 was determined by Southern Blot analysis using "Probe A" and by PCR-based genotyping (FIG. 1B).

Probe A has the following nucleotide sequence [SEQ ID NO:21]:

```
[SEQ ID NO: 21]
Probe A has the following nucleotide sequence:
TACCTGCCTT ATTCAGAGGA GTCAAGTGTG TATCTTAAGT CATTTTGTTC CAGTAATTTG

AAGAGCCTAA GACTTTAAAA GAGAGGCTGT GGTATGGTCG AGAGCATAAA CTTTGAGGCC

AAGCTTCCTG AAGTAAGCCG TGGCATTACT GTGGCTCACC GGAGCCGAGT CAGATCTAGT

TGCAGAAGCT CCTCGTCTGT CATTGAGAGT AGTGTCCCAC CTACCTTAGG GCTGCTACAA

GGATAAAACT GAAAACCTTC CTGACAGACA GTATCCTATG AATGTCATTA TCATCACCTA

TGTATTAATT TTAACTCTCC TGAGTTGTCC ATTGGGTTAT TTAAATGCTT GTTAAATAAA

CTTGAAGTTT TAAAGACTCA TTTCCCATCA TTAGCCCATT GTGGTCATTG TCATTAAGAT

TACAACAGAA TCCACACATC GTTCACAGGT ACAGTGCATT GCATATGTCG GAAAGAAATG

CTCTTCCATG CCGTGTGTGC TTGCCTGTGT CTGTGGATGG TACTGTTGAT TGTTGTGCTC

TGTAGGAAAA ATACCAATGA CAAAACAATA CAGTGCTGTT GCCCTGCTTG TAATTGTATC

TCCCTAAAAT CCTGAGGGAC AAACTGAATC ACAAGGCTAT TGAGACAGGA GT
```

This sequence is from murine genomic Mig-6 DNA and is located upstream of the 5'-homologous recombination sequence described above and used in the knockout construct.

Figure 1C:
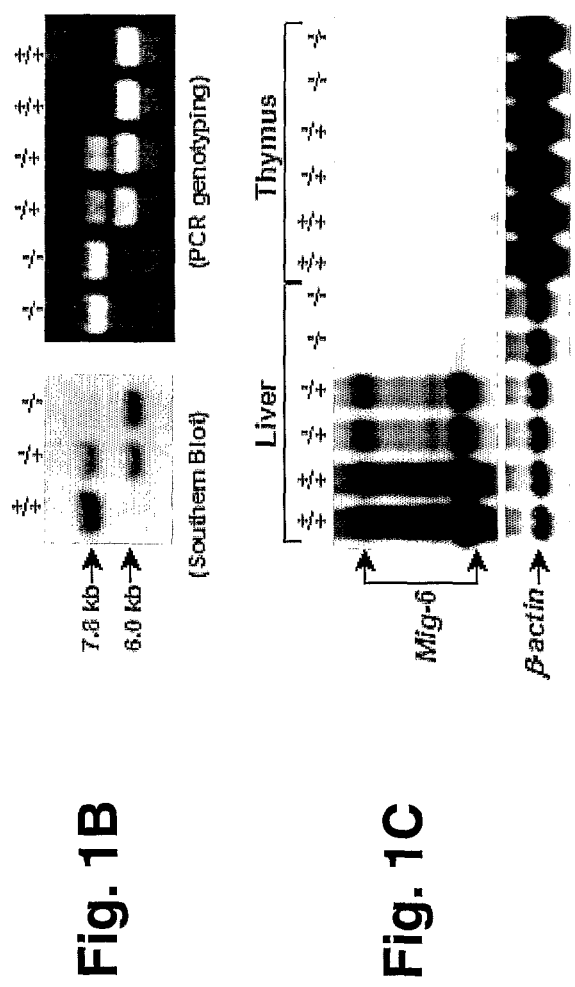

The lack of Mig-6 expression was confirmed in liver and thymus derived from homozygous mice by Northern Blot analysis (FIG. 1C). Homozygous Mig-6$^{-/-}$ KO mice are viable, but a reduction in litter size to one half that of heterozygous litters was observed, indicating some embryonic lethality is associated with the loss of both Mig-6 alleles.

While Mig-6 was expressed at high levels in mouse liver and kidney, no obvious pathological changes or defects in these tissues were observed.

Figures 2A, 2P:
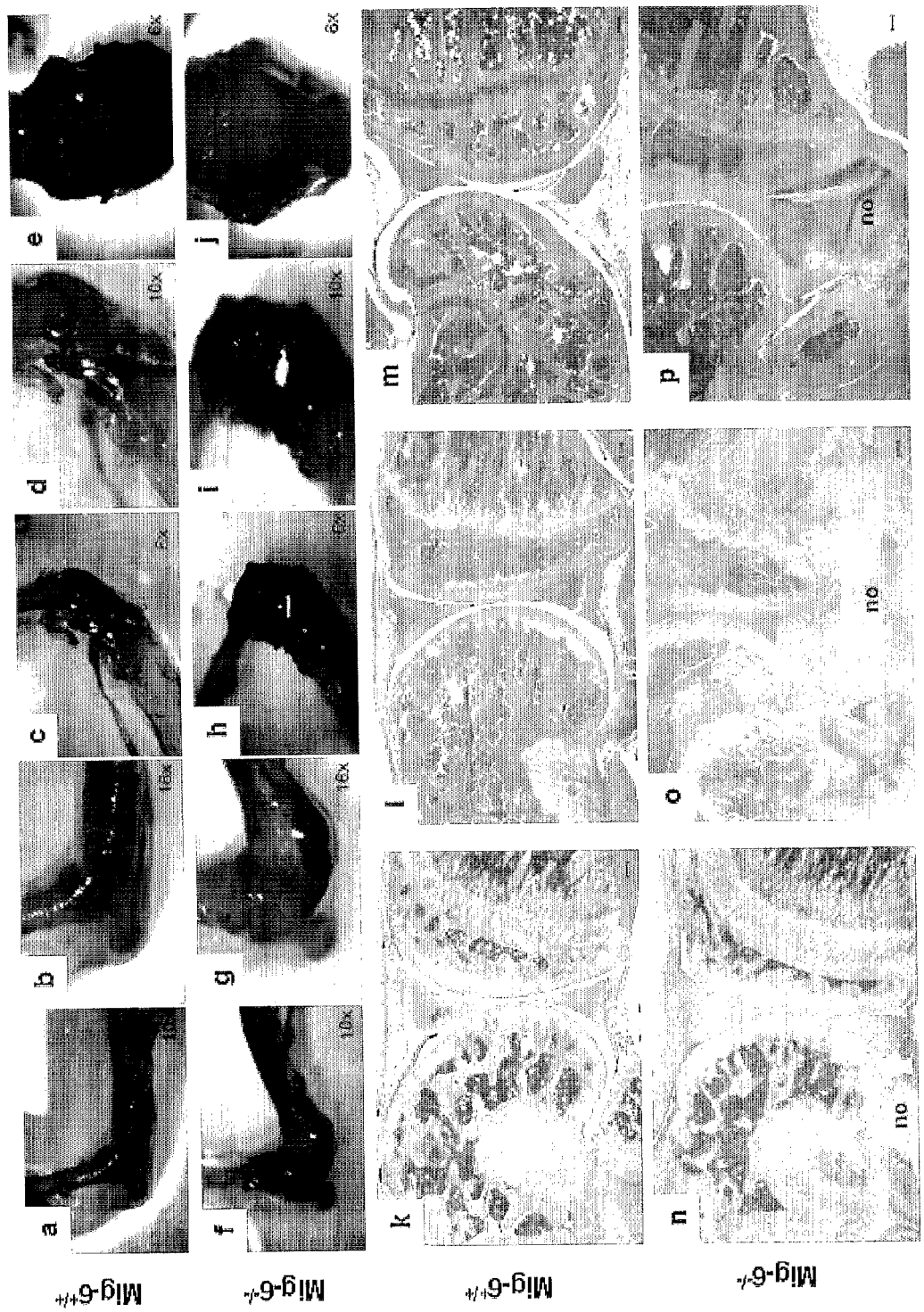
FIG. 2A-2P. Disruption of Mig-6 results in multiple joint deformities and fibrocartilagenous hyperplasia. Adult skeletons of 4 months old mice were stained with alizarin red and photographed under microscope. Representative images of ankle (A and D), knee (B and E) and temporal-mandibular joints (C and F) derived from Mig-6$^{+/+}$ (A-C) and Mig-6$^{-/-}$ (D-F) mice are shown. H&E staining was performed on knee joint sections prepared from 1.5 months (0 and J), 3 months (H and K) and 6 months (I and L) Mig-6$^{+/+}$ (G-I) and Mig-6$^{-/-}$ (J-L) mice. The abnormal nodules outgrowing within Mig-6$^{-/-}$ knee joints (J-L) are indicated as "nod". Scale bar: 100 μm. Identical results were observed in Mig-6$^{-/-}$ mice derived from another independent ES clone (not shown).

Surprisingly, the present inventors found that most of the Mig-6$^{-/-}$ mice showed an abnormal gait as early as one-month of age. With time, progressive enlargement and deformity of multiple joints were found in the Mig-6$^{-/-}$ mice, especially the knees, ankles and temporal-mandibular joints (TMJ) (FIG. 2D-F). Such deformities were not observed in wild type or heterozygous Mig-6 mice (FIG. 2A-C). All Mig-6$^{-/-}$ animals developed joint deformities, leading to joint stiffness and a majority of animals died within 6 months, most likely due to TMJ ankylosis (FIG. 2F) resulting in an inability to eat and/or drink Late stage mutant mice were thin and appeared exhausted compared to their wild type and heterozygous littermates.

Figures 3A, 3B, 3C, 3D, 3E:
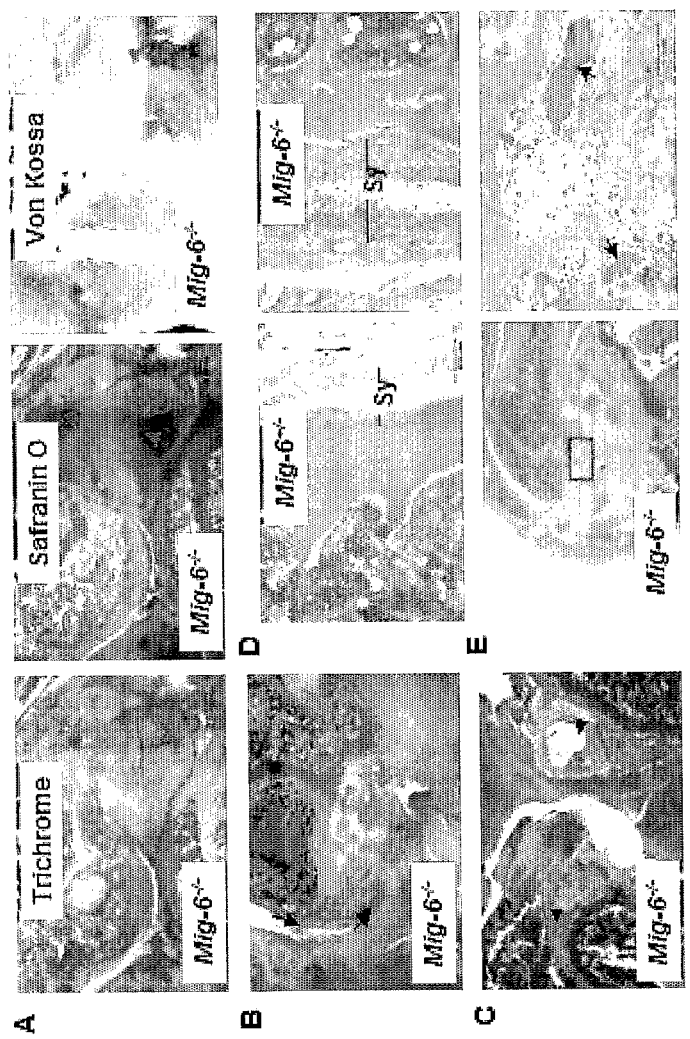
FIG. 3A-3E. Mig-6$^{-/-}$ mutant joints display multiple characteristic pathological features of osteoarthritis. (A) Bony outgrowth or osteophyte formation. Mason's Trichrome staining for collagens (blue color) or Safranin O staining for proteoglycans (red color) was performed on knee joint sections prepared from a 3 months old Mig-6$^{-/-}$ mouse. Arrows indicate the abnormal outgrowing nodules that have abundant collagen and proteoglycan. Von Kossa staining of calcium deposition was performed on non-decalcified knee joint section prepared from a 5.5 months old Mig-6$^{-/-}$ mouse. Arrowheads indicate matrical calcium in the inner zone of the nodules. (B) Degradation of articular cartilage. Arrows indicate rough joint surface and degraded articular cartilage in a 4 months old Mig-6$^{-/-}$ knee joint stained with Safranin O. (C) Subchondral cyst formation. Two large cysts filled with or without fibroblast like cells are observed beneath degraded articular cartilage in a 3 months old Mig-6$^{-/-}$ knee joint as indicated by the arrowheads. (D) Synovial hyperplasia. H&E knee joint sections were prepared from 2 months old age-matching Mig-6$^{+/-}$ and Mig-6$^{-/-}$ mice. Compared to a thin layer of synovial lining in Mig-6$^{+/-}$ joint (normal), multi-layers of synovial lining cells (Sy) are observed in Mig-6$^{-/-}$ joint. (E) Vascularization in avascular joint region. Various sizes of blood vessels indicated by arrows are observed in 4 months old Mig-6$^{-/-}$ knee joint, accompanied by newly repaired tissues.

The joint deformities of Mig-6$^{-/-}$ mice were examined by first preparing H&E sections from joints taken at different ages and compared to similar preparations from Mig-5$^{+/+}$ and Mig-6$^{+/-}$ mice. In the knee joint of Mig-6$^{-/-}$ mice at ages from 1.5-6 months, outgrowths of abnormal bony nodules were observed within the joint space adjacent to the margin of the synovial and cartilage junctions, accompanied by narrowing of joint space over time (FIG. 2J-L). Similar pathological changes were observed in ankle joints of these mice as well as in the TMJ, neck, and other joints. Joint sections derived from younger Mig-6$^{-/-}$ mice at ages of 12 and 20 days were also examined and showed no signs of these structural abnormalities, suggesting that the bony nodules and the degenerative joint changes developed at later stages. The abnormal nodules surrounded by spindle-shaped mesenchymal like cells contained hyperplastic fibrocartilage with variable chondrocyte shapes, representing different stages of cartilage matrix development (FIG. 3A). The nodules were abundant in the cartilage matrix as determined by Mason's Trichrome Staining for collagen and Safranin O staining for proteoglycan (FIG. 3A). Compared to the outer zones of the nodules, the inner zones had a higher density of proteoglycans, which were produced by mature chondrocytes (FIG. 3A). The deeper zones of the nodules were undergoing endochondral ossification. Von Kossa staining revealed calcium deposition of osteoid matrix (FIG. 3A). This bony outgrowth had the components mimicking osteophyte formation, a characteristic feature of human osteoarthritis (Koopman et al., supra; Resnick et al., supra).

In addition to bony outgrowths, the present inventors also observed other arthritic changes in Mig-6$^{-/-}$ mutant joints, including degradation of articular cartilage, formation of subchondral cysts, synovial hyperplasia and abnormally robust vascularization (FIG. 3B-E). In Mig-6$^{-/-}$ mutant joints, the surfaces of the articular cartilage become rough and disorganized. Degradation of articular cartilage is observed at multiple regions across the joint, accompanied by signs of tissue regeneration (FIG. 3B). Subchondral cyst formation is another characteristic pathological feature in human osteoarthritis. This was also observed in the Mig-6$^{-/-}$ arthritic joints: Various sized subchondral cysts filled with fibroblast-like cells were present, separated from the bony structures that formed beneath the degraded articular cartilage (FIG. 3C). By comparison, the joints of age-matched Mig-6$^{+/+}$ and Mig-6$^{+/-}$ mice did not show any evidence of these pathological changes. Along with the articular cartilage degradation, synovial cells lining the joint of mutant mice were hyperplastic, with multiple cell layers, compared with the thin layer of synovial cells found in normal joints (FIG. 3D). Accompanying the destructive and reconstructive remodeling activities in the mutant joints, the present inventors observed vascularization in regions that are normally avascular (FIG. 3E) (Koopman et al., supra; Resnick et al., supra).

Figures 4A, 4B, 4C, 4D, 4E, 4F:
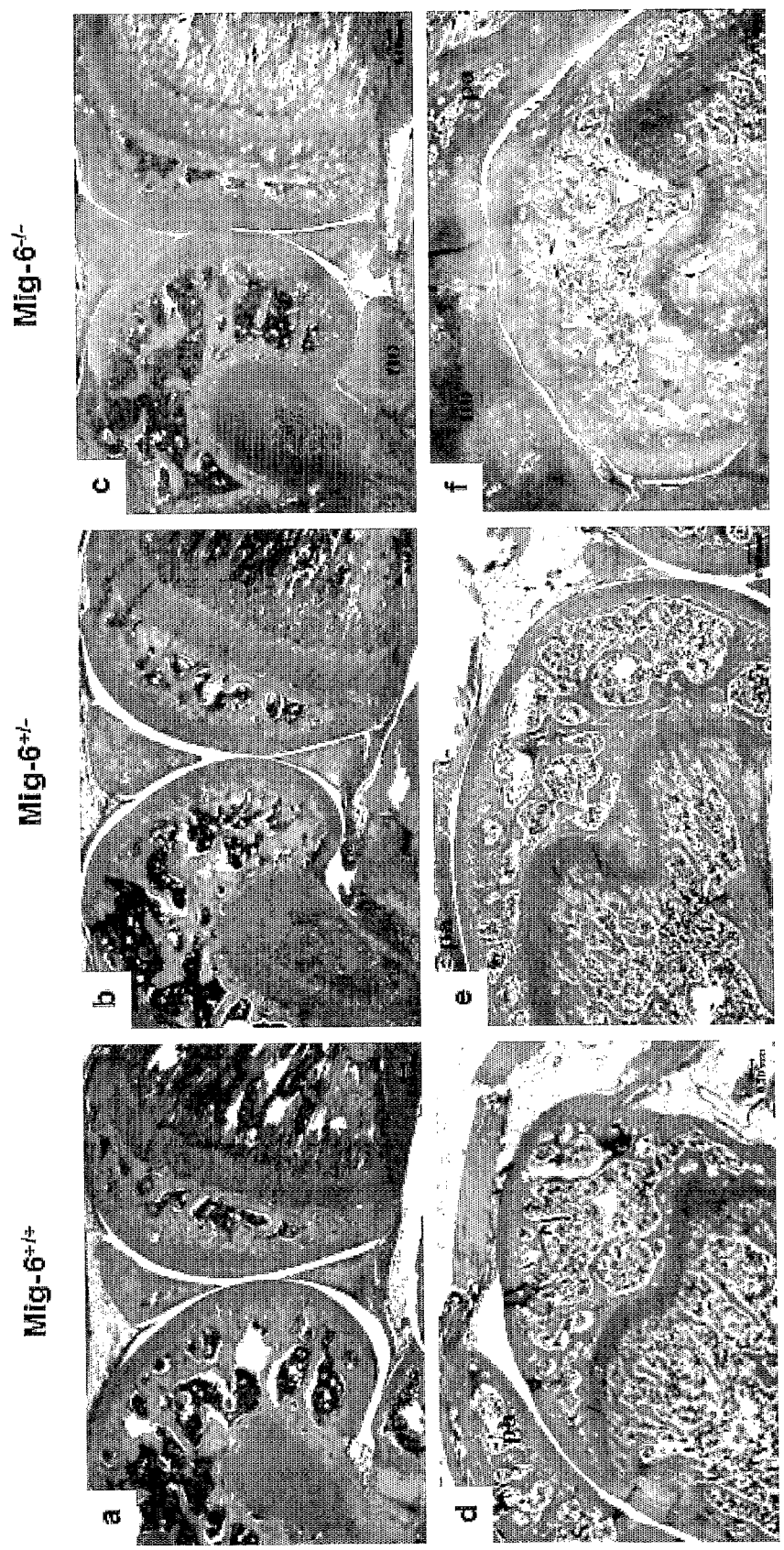
FIG. 4A-4F. Changes of proteoglycan distribution are observed in articular cartilage of late-stage Mig-6$^{-/-}$ mutant joint. Safranin O staining was performed on knee joint sections prepared from litters of 1.5 months (A-C) and 3 months (D-F) old Mig-6$^{+/+}$ (A, D), Mig-6$^{+/+}$ (B, E) and Mig-6$^{-/-}$ (C, F) mice. A lack of proteoglycan staining in the articular cartilage surfaces of patella and femur was observed in 3 months old Mig-6$^{-/-}$ mutant joint (F). Instead, the proteoglycan positive zones are shifted to deeper regions (F). No obvious difference of proteoglycan staining was observed in 1.5 months old joints. nod: nodule; pa: patella.

Articular cartilage not only provides a low-friction surface for joint movement but also flexibility for withstanding concussive forces applied to the joint during a subject's normal activity. The cartilage matrices of which proteoglycan and collagen are the two major components, are responsible for both these tasks (Hamerman, D. (1989) *N. Engl. J. Med.* 320:1322-30). In osteoarthritis, the density of proteoglycan is reduced within the articular cartilage due to disruption of a balance between degradation and production (Sandell, L J et al., (2001) *Arthritis Res.* 3:107-13; Rowan, A. D. (2001) *Expert Rev. Mol. Med.* 2001:1-20). The hyaline cartilages of Mig-6$^{+/+}$ and Mig-6$^{+/-}$ mice displayed intense proteoglycan staining throughout articulating surface, such as in the femur and patella (FIGS. 4D and E). However, the present inventors observed a lack of proteoglycan staining within some areas of these articular surfaces, especially in late stages of the Mig-6$^{-/-}$ mutant joint destruction (FIG. 4F). Interestingly, beneath the cartilage, there is proteoglycan staining in the damaged joint (FIG. 4F). Proteoglycan staining in the joints of mutant mice in early stages of joint disease is similar to that in wild type and heterozygous mice (FIG. 4A-C).

Figure 5:
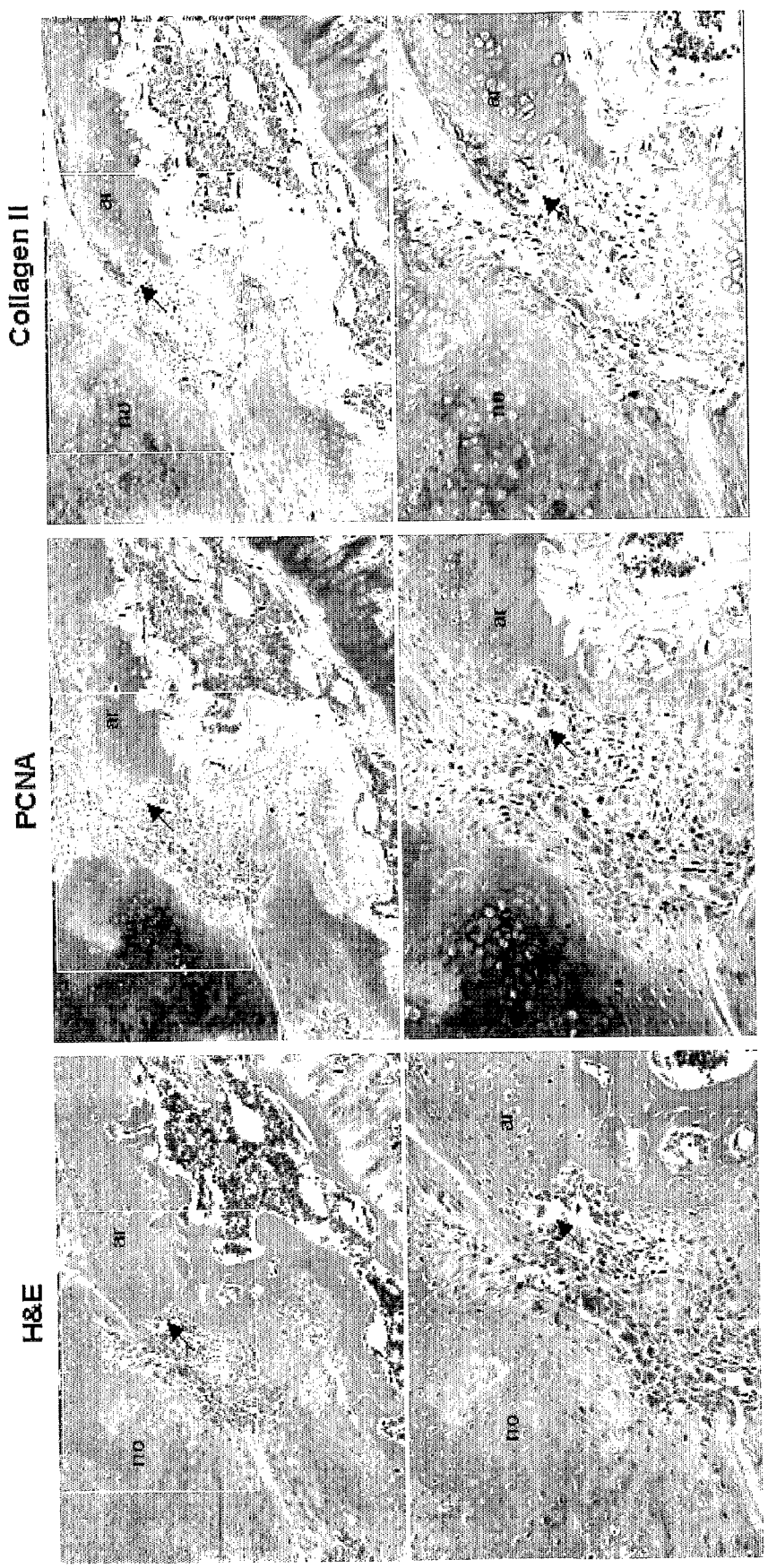
FIG. 5. Bony outgrowths are derived from proliferation of mesenchymal like progenitor cells. Knee joint sections were prepared from a 3 months old Mig-6$^{-/-}$ mouse, and immunohistochemically stained by anti-PCNA or anti-collagen type II antibodies. The spindle-shaped mesenchymal like cells at the edge of the bony nodule display PCNA-positive staining (brown color), while no PCNA-positive cells were observed in the inner zone of the bony nodule. Different from PCNA staining pattern, only a narrow zone of chondrocytes between the PCNA-positive cells and the well differentiated chondrocytes in the deeper zone display collagen type II staining (brown color). PCNA positive cells are also observed in areas where articular cartilage has been degraded and replaced by newly formed tissues (arrow). The photos in the bottom panel are higher magnification images taken from the fields indicated in the top panel. nod: nodule; ar: articular cartilage.

To determine which cells are responsible for the regeneration and formation of osteophyte in the Mig-6$^{-/-}$ mouse joints, immunohistochemical staining was performed to identify proliferating cells in G1 and S using a mAb against PCNA. Interestingly, the present inventors found that the mesenchymal-like spindle-shaped cells at the outer zone of the osteophyte and in the region of cartilage repair were strongly positive for PCNA staining (FIG. 5). No PCNA+ cells were observed in the inner zone of the osteophytes, suggesting that the spindle shaped cells are proliferating and likely responsible for osteophyte formation. The mesenchymal progenitor cells have the capability to proliferate and differentiate into chondrocytes (Cancedda, R et al., (1995) *Int. Rev. Cytol.* 159:265-358). Sections were stained with antibody against mouse type II collagen, a matrix protein that is synthesized by the mature chondrocytes but not by progenitor cells nor by terminally differentiated hypertrophic chondrocytes. Only the layer of chondrocytes lying between the mesenchymal progenitor cells and the chondrocytes in the deeper zones stained positive for type II collagen (FIG. 5), indicating that the bony outgrowths in the Mig-6$^{-/-}$ mutant joints are derived from proliferating mesenchymal progenitor cells that differentiate into chondrocytes.

Figure 6A:
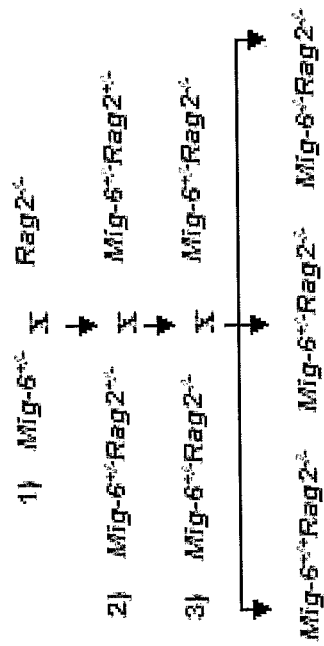
FIG. 6A-B. Absence of Rag2 does not rescue the joint phenotype of Mig-6$^{-/-}$ mice. (A) Crossing scheme for generating double knockout ("KO") mice. The litters derived from intercrossing Mig-6$^{+/-}$Rag2$^{-/-}$ mice were used for analyzing the joint phenotype. (B) Representative images of knee joints were photographed from H&E sections prepared from 4.5-month old Mig$^{+/+}$Rag2$^{-/-}$ and Mig-6$^{-/-}$Rag2$^{-/-}$ mice, respectively. The age-matched Mig-6$^{+/-}$Rag2$^{-/-}$ joint appeared normal (data not shown). nod: nodule.
Figure 6B:
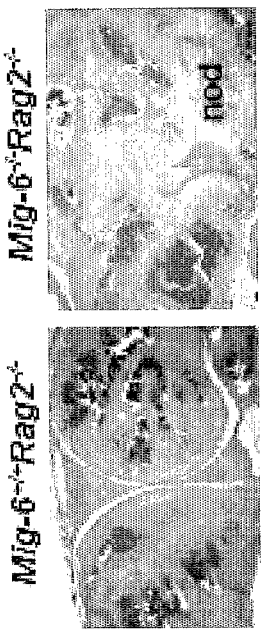

In contrast to inflammatory arthritides such as rheumatoid and infectious arthritis, osteoarthritis usually shows relative few inflammatory cells infiltrating affected joints. Although no significant inflammatory cells were observed in Mig-6$^{-/-}$ mutant joints, the present inventors frequently observed that the thymuses of these mice were enlarged compared to normal. To determine whether the immune system played a role in the development of the Mig-6$^{-/-}$ joint phenotype, the present inventors crossed these animals with Rag2 deficient mice (Shinkai, Y et al., supra) to generate progeny deficient for both Mig-6 and Rag2. These mice displayed severe immune deficiency, due to a failure of development of both mature B and T cells. This phenotype, however, did not alter either the frequency or extent of the Mig-6$^{-/-}$ joint phenotype (FIG. 6). Thus, the "adaptive" or "acquired" immune system does not appear to play a role in this joint disorder.

Many growth factors and cytokines influence the pathogenesis of OA (Rowan, A D (2001) *Expert Rev. Mol. Med.* 2001:1-20), including TGF-β (Hulth, A et al., (1996) *J. Orthop. Res.* 14:547-53; van Beuningen, H. M. et al. (2000) *Osteoarthritis Cartilage* 8:25-33; Allen, J. B. et al. (1990) *J. Exp. Med.* 171:231-47; Bakker, A. C. et al., (2001) *Osteoarthritis Cartilage et al.,* 9:128-36; Scharstuhl, A. et al., (2002) *J. Immunol.* 169:507-14; Serra, R. et al. (1997) *J. Cell Biol.* 139:541-552; Yang, X., et al. (2001) *J. Cell Biol.* 153:35-46) and BMPs (Rountree, R. B. et al., (2004) *PLoS Biol.* 2:1815-27). In addition, genetic predisposition to osteoarthritis has been linked to mutations in genes like COL2A1 (Aigner, T et al., (2003) *Curr. Opin. Rheumatol.* 15:634-40).

Figure 7:
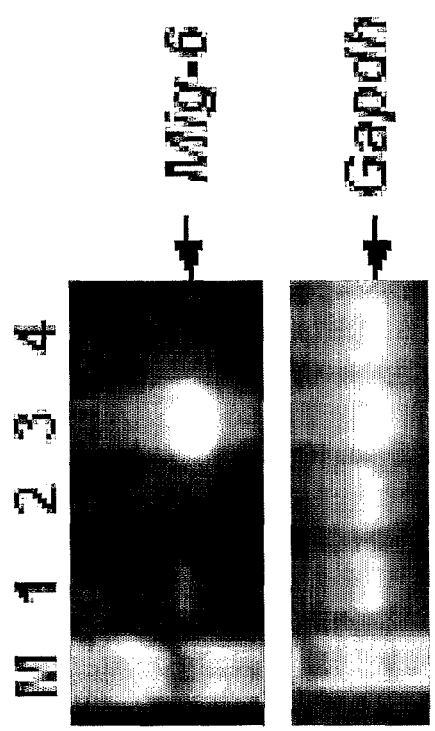
FIG. 7. Detection of Mig-6 Expression in mouse joint. RT-PCR was performed using total RNA prepared from whole knee joint (lanes 1 and 2) or liver (lanes 3 and 4) derived from Mig-6$^{+/+}$ (lanes 1 and 3) or Mig-6$^{-/-}$ (lanes 2 and 4) mice. Arrows indicate the amplification of Mig-6 and GAPDH, respectively. GAPDH serves as internal control. M: DNA ladder.

Here, it is disclosed for the first time that Mig-6-deficient mice display multiple joint defects. The phenotypes include joint deformities, degradation of articular cartilage, subchondral cyst formation and bony outgrowths or osteophyte formation (FIGS. 2 and 3). The pathological features are strikingly similar to human osteoarthritis. The most affected joints are knee and ankle joints, and TMJ, with less frequent occurrence in other joints (FIG. 2). The affected joints bear relatively high amounts of stress that could be a major factor in developing this disorder. Wild type Mig-6 is expressed in knee joint as determined by RT-PCR (FIG. 7). It has recently been shown that Mig-6 expression is increased in response to mechanical load as well as in osteoarthritic cartilage of canine joints (Mateescu, R G et al., (2005) *Biochem. Biophys. Res. Commun.* 332:482-6). Mechanical factors are thought to play an important role in development and degeneration of articular cartilage by influencing expressions of many genes that are crucial for the processes of cell growth, vascularization and ossification (Carter, D R et al., (2004) *Clin. Orthop. Relat. Res.* 427 Suppl:S69-77)

Mechanical joint stress constitutively stimulates joint regeneration by inducing certain growth factors like TGF-β, BMP, EGF or HGF/SF and other cytokines that stimulate proliferation and differentiation of cells required for joint renewal. According to the present invention, under normal conditions, this regenerative activity is counter-balanced by suppressor activity of Mig-6 that fine-tunes the extent of proliferation and renewal. Losing the suppressing function of Mig-6 causes over-proliferation of mesenchymal progenitor cells that leads to an abnormal state of chondrogenic differentiation and bony outgrowths (FIG. 5).

The profound osteoarthritic phenotype of Mig-6 deficient mice make them a very useful model for (1) determining what factors in the Mig-6 signaling pathway are involved in osteoarthritis; (2) for understanding the molecular mechanism underlying this disease process; and (3) for testing drugs or therapies which may help to alleviate the symptoms or alter the disease progression of osteoarthritis.

EXAMPLE III

Mig-6 and Tumor Suppressor Gene Activity:
Experimental Procedures

Human Lung Cancer Cell Lines and Cell Culture

The nine non-small cell lung cancer (NSCLC) cell lines EKVX, HOP62, HOP92, NCI-H23, NCI-H226, NCI-H322M, NCI-H446, NCI-H522, and A549 were derived from the NCI 60 cell lines. The cells were cultured in RPMI 1640 medium supplemented with 10% fetal bovine serum.

Mutational Analysis of Mig-6

Human lung cancer and normal control tissue was obtained through the Cooperative Human Tissue Network (CHTN). Genomic DNA was isolated from human cell lines and tissues. Polymerase chain reaction (PCR) was performed to amplify the entire coding regions of Mig-6 (exons 2, 3, and partial exon 4) using three primer pairs. Primers used for screening genomic DNA mutations in the coding region of human Mig-6 are as follows. The same set of primers is also used for sequencing PCR products for determining if there is a mutation or not in the coding region of human Mig-6.

(1) Pair-I for amplification of exon 2 & 3: Hmig-I1s & Hmig-I3As

```
Hmig-I1s (sense sequence derived from intron 1 of
human Mig-6 genomic DNA)
5'-TTCTCTCATCTCTTCTACCTCC-3'      [SEQ ID NO: 11]

Hmig-I3As (antisense sequence derived from intron
3 of human Mig-6 genomic DNA)
5'-TAATGCTGGAGGACAAGCTAAC-3'      [SEQ ID NO: 12]
```

(2) Pair-II for amplification of partial exon 4: Hmig-I3s & Hmig-I4As

```
Hmig-I3s (sense sequence derived from intron 3)
5'-TTCACTCAGGAAGAAAGCTGTG-3'      [SEQ ID NO: 13]

Hmig-I4As (antisense sequence derived from exon 4)
5'-CTCTGCACTTCAATCAAACTGG-3'      [SEQ ID NO: 14]
```

The PCR products were purified by QIAquick PCR Purification Kit (QIAGEN) and sequenced using an ABI7000 sequencer.

Western Blot Analysis

Western blotting was performed as described previously (Zhang et al., Proc. Natl. Acad. Sci. USA 100:12718-23, 2003). Briefly, the total cell lysates were extracted from lung cancer cells and resolved by Tris-glycine gel (from Invitrogen). The proteins were then transferred to a PVDF membrane (Invitrogen) and detected by immunoblotting with the indicated antibody. The anti-EGFR, anti-p-EGFR, and anti-Met antibodies were purchased from Santa Cruz Biotechnology; the anti-β-actin was from Sigma; the anti-p-ERK and anti-ERK were from Cell Signaling Technology; and the anti-Mig-6 was produced by immunizing rabbits with the synthetic peptides derived from the C-terminal 14 amino acids of Mig-6, SHGKRKHLSYVVSP (SEQ ID NO:22)

Northern Blot Analysis

Total RNA (20 μg per sample) was subjected to Northern blot analysis as described (Zhang et al., supra). The DNA fragment used for probing Mig-6 was amplified from the region between nucleotides 213 and 1601 of human Mig-6 (Accession no. NM_018948) by reverse transcriptase PCR (RT-PCR). The probe for human GAPDH has been described by Zhang et al., supra.

Mouse Histology and Immunohistochemistry (IHC)

The generation and genotyping of Mig-6 knock-out mice was described above in Examples I and II. The mice analyzed in this study are on a B6/129 strain genetic background. Mouse tissues were fixed in formalin and embedded in paraffin. Sections (5 μm) were stained with hematoxylin and eosin (H&E) for examination. IHC staining of PCNA was performed as described above.

EXAMPLE IV

EGFR and Met Signaling Regulate Mig-6 Expression in Lung Cancer Cells

Inappropriate activation of EGFR and Met receptor tyrosine kinase signaling by overexpression or mutation is involved in lung carcinogenesis (Zochbauer-Muller et al., Annu. Rev. Physiol. 64:681-708, 2002). Mig-6 has been shown to be a negative feedback inhibitor of EGFR signaling in other cell types (supra). In addition, the present inventors observed that Mig-6 expression is strongly induced by HGF/SF in a sarcoma cell line. Here it is shown that that EGF or HGF/SF can also regulate Mig-6 expression in lung cancer cells.

Both EGFR and Met were highly expressed in several of 9 lung cancer cell lines tested (including EKVX and HOP62) by Western blot analysis (FIG. 8A). In lung cancer cells, as in other cell types, the level of the Mig-6 protein increased with EGF treatment of HOP62 cells (FIG. 8B) and with HGF/SF treatment of EKVX cells (FIG. 8C). Notably, no Mig-6 protein was detected in NCI-H322M and NCI-H226 cells (FIG. 8A).

EXAMPLE V

Regulation of Mig-6 by EGFR and Met is Mediated Through the MAP Kinase Pathway

To determine the downstream pathway involved in EGFR-mediated and Met-mediated Mig-6 regulation in lung cancer cells, HOP62 and EKVX cells were treated with various pathway inhibitors for 1 h prior to a 4 hr period of induction by EGF or HGF/SF. Both HOP62 and EKVX cells expressed significant levels of EGFR and Met (FIG. 8A). Both EGF and HGF/SF induced Mig-6 expression in these two cell lines (FIG. 8B-8D).

Pre-treatment with the MAP kinase pathway inhibitor (a MEK inhibitor) U0126, but not with the PI3 kinase inhibitor LY294002, diminished EGF- and HGF/SF-induced Mig-6 expression (FIG. 8D).

Thus, regulation of Mig-6 expression by EGFR or Met signaling is mediated at least partially through the MAP kinase pathway. The level of Mig-6 protein is very high in NCI-H23 cells, which carry an activating mutant Ras allele (Koo et al., Cancer Res 59:6057-62, 1999) but have barely detectable EGFR or Met (FIG. 8A). Ras, a downstream molecule of the RTK, EGFR, and Met, is required for the activation of the MAPK/ERK pathway. The high level expression of Mig-6 in NCI-H23 cells may be due to constitutive activation of the Ras pathway.

EXAMPLE VI

Mig-6 Feedback Regulation by EGFR and Met is Lost in NCI-H226 Cells

In EKVX cells, the amount of Mig-6 protein rapidly increased in response to EGF treatment (FIG. 9A). Yet even after 4-6 hrs, no Mig-6 was detected in NCI-H322M or NCI-H226 cells using an antibody directed against the Mig-6 C-terminal 14 amino acids (FIG. 9A).

EGF induced EGFR tyrosine phosphorylation and downstream ERK activation in EKVX, NCI-H322M, and NCI-H226 cells (FIG. 9A).

HGF/SF induced Mig-6 expression in EKVX and HOP62 cells (FIGS. 8A-8D and 9B), but like EGF, HGF/SF did not induce Mig-6 in NCI-H226 cells that express high levels of Met and respond to HGF/SF (FIGS. 8A-8D and 9B). Interestingly, the duration of ERK phosphorylation by EGFR and Met was more sustained in Mig-6-deficient NCI-H226 and NCI-H322M cells than in EKVX and HOP62 cells expressing a Mig-6 product (FIGS. 9A and 9B).

Expression of Mig-6 at the transcriptional level was evaluated in NCI-H322M and NCI-H226 cells by Northern blot analysis using total RNAs prepared from NCI-H322M and NCI-H226 cells (with or without EGF treatment). Mig-6 mRNA level is dramatically increased in NCI-H322M cells within 1 h (FIG. 9C). However, almost no Mig-6 mRNA expression was detected in NCI-H226 cells even after 1-4 h of EGF treatment (FIG. 9C).

Thus, feedback up-regulation of Mig-6 by EGFR or Met was defective in NCI-H226 lung cancer cells, even though the MAPK/ERK pathway that mediates the RTK-induced up-regulation of Mig-6 was intact (FIGS. 9A and 9B). This implies that the promoter regulatory regions of Mig-6 in NCI-H226 are either genetically or epigenetically altered.

Mig-6 protein was not detectable in NCI-H322M cells (FIG. 9A), despite the fact that EGF could induce Mig-6 mRNA expression (FIG. 9C). This suggests a potential alteration in the properties of Mig-6 protein in these cells.

EXAMPLE VII

The Mig-6 Gene is Mutated in Human Lung Cancer Cell Lines and Primary Lung Cancer The above results prompted the inventors to examine whether Mig-6 was genetically altered in human lung cancer. From nine NSCLC cell lines derived from NCI 60 cell lines, two point mutations were identified in the coding region of Mig-6. Even when RTK-induced Mig-6 transcription was silenced (FIGS. 9B and 9C), the gene in NCI-H226 cells bore a homozygous missense mutation leading to the replacement of Asp with Asn at codon 109.

Figure 10A:
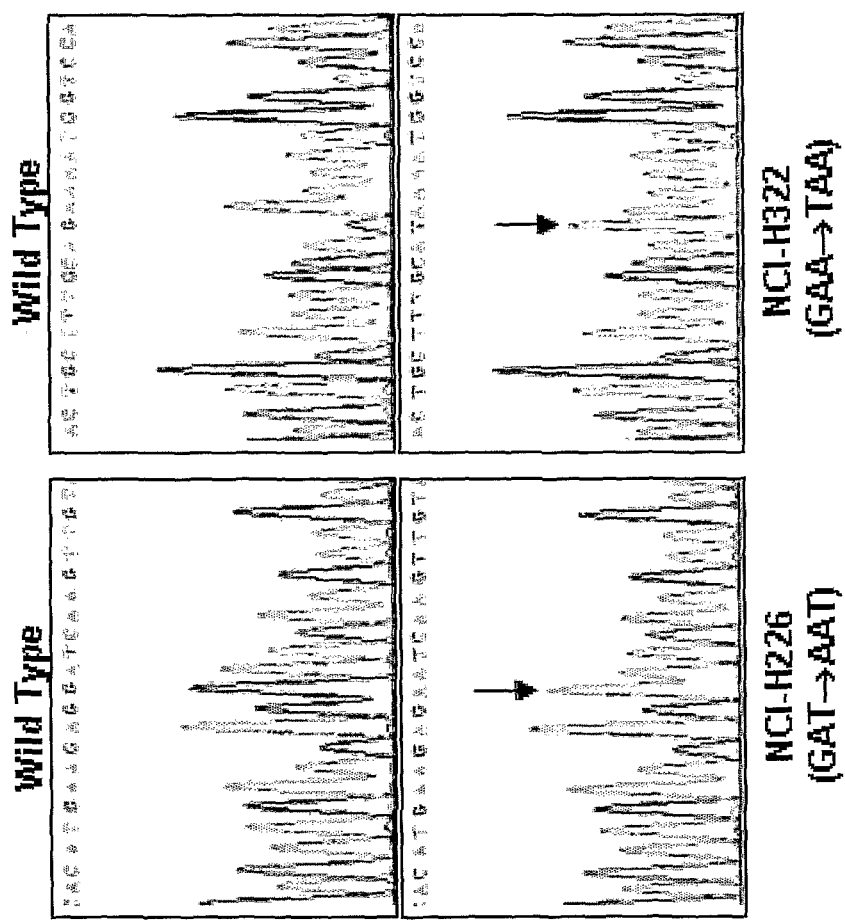
FIG. 10A-10C: Identification of Mig-6 mutations in human lung cancer cell lines and primary lung cancer.
Figure 10B:
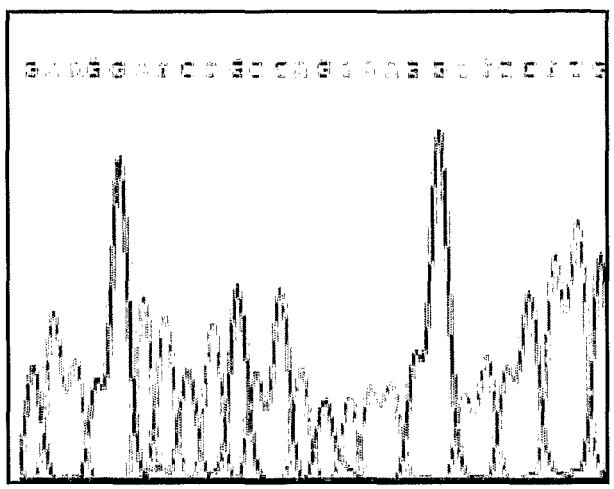
Figure 10B:
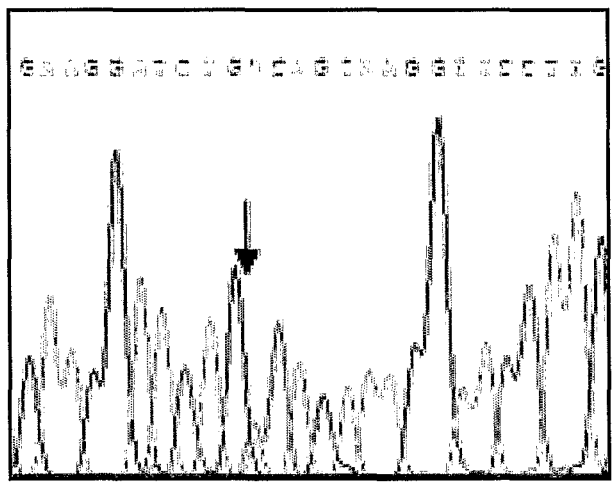
Figure 10B:
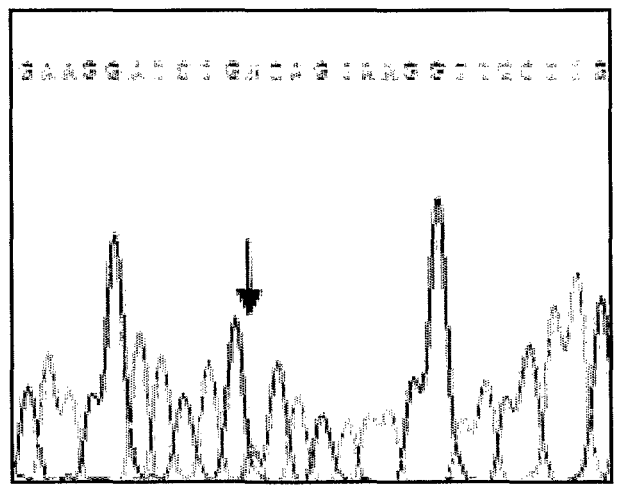
Figure 10C:
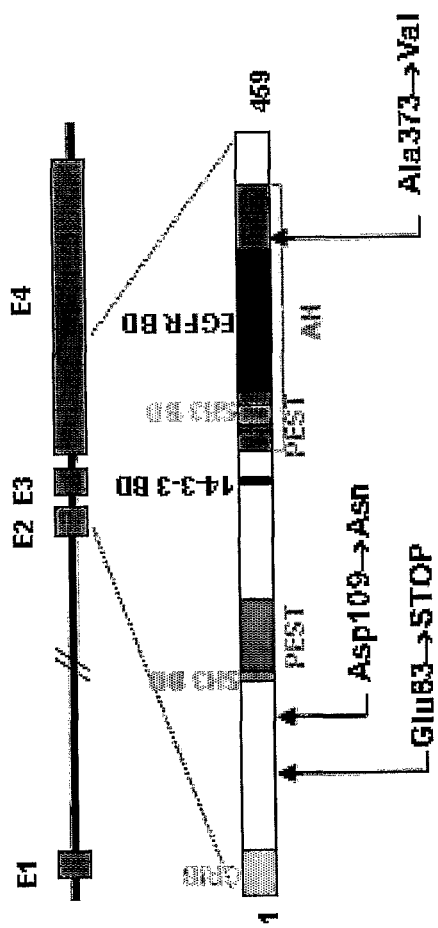
Figures 11A, 11B, 11C, 11D, 11E, 11F, 11G, 11H:
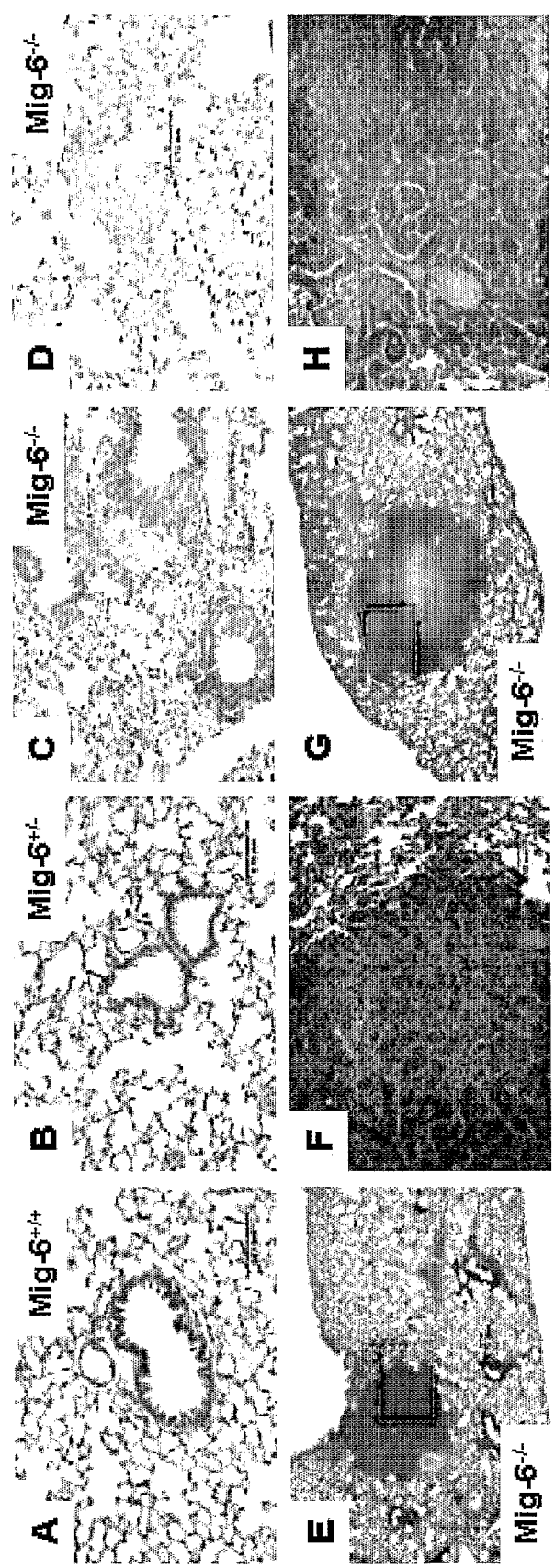
FIG. 11A-11H: Mig-6 deficiency in mice causes lung carcinogenesis.

Furthermore, the Mig-6 protein product in NCI-H322M carried a homozygous nonsense mutation, resulting in a truncation after codon 83 (FIGS. 10A-10C and Table 1). This alteration prevented the protein from being detected by the antibody specific for the C terminus of Mig-6 (FIGS. 8A-8D and 9A).

Forty one cases of primary human lung cancers were also examined. A germline mutation was identified in one patient, an alteration of Ala to Val at codon 373 (FIGS. 10A-10C and Table 1). Polymorphisms in Mig-6 were also observed in lung cancer cell lines and primary lung cancers (Table 1).

EXAMPLE VIII

Disruption of Mig-6 in Mice Causes Lung, Gallbladder, and Bile Duct Carcinogenesis Evidence supporting the tumor suppressor function of Mig-6 was also obtained using the Mig-6-deficient mice described herein. As discussed extensively above, disruption of the Mig-6 gene in mice by gene targeting technology resulted in early-onset degenerative joint disease (supra). Although Mig-6 was shown to be expressed in mouse lung tissue, developmental lung defects were not observed at early stages of development in Mig-6-deficient mice. (FIG. 11A-11H and Table 2). A majority of Mig-6 mutant mice die within 6 months due to the joint abnormality and its sequelae (supra). Of a total of 29 Mig-6$^{-/-}$ mice of ages between 5 and 13 months, four cases of lung cancer were observed. One animal had an adenocarcinoma, a second animal had two adenomas in two different lobes, and two mice were observed with a single adenoma each. In addition, in the 29 homozygous animals, 11 cases of bronchi or bronchiole epithelial hyperplasia were observed (Table 2).

Statistical analysis (Fisher's exact test) revealed that the lungs from Mig-6-deficient mice had significant pathological changes, including hyperplasia and neoplasia, relative to those from the control wild-type (p=0.001398) and heterozygous (p=0.000017) mice.

TABLE 1

Summary of Mig-6 mutations identified in human lung cancer cell lines and primary lung cancer

|  | Diagnosis | Nucleotide | Exon | Protein | Mutation Type | Genotype |
|---|---|---|---|---|---|---|
| Cell lines |  |  |  |  |  |  |
| NCI-H23 | Adenocarcinoma | 942 C→A | 4 | R244R (CGA→AGA) | Polymorphism | Homozygous |
| NCI-H226 | Squamous Cell Carcinoma | 537 G→A | 4 | D109N (GAT→AAT) | Missense | Homozygous |
| NCI-H322M | Adenocarcinoma | 459 G→T | 4 | E83Stop (GAA→TAA) | Nonsense | Homozygous |
| Human Lung Tissues |  |  |  |  |  |  |
| 1041190A | Squamous Cell Carcinoma | 1118 C→T | 4 | A373V (GCC→GTC) | Missense | Heterozygous |
| 1041190B | Normal lung tissue | 1118 C→T | 4 | A373V (GCC→GTC) | Missense | Heterozygous |
| 4030373A | Adenocarcinoma | 60 A→G | 2 | L20L (CTA→CTG); | Polymorphism | Heterozygous |
|  |  | 730 C→A | 4 | R244R (CGA→AGA) |  |  |
| 4030373B | Normal lung tissue | 60 A→G; | 2 | L20L (CTA→CTG); | Polymorphism | Heterozygous |
|  |  | 730 C→A | 4 | R244R (CGA→AGA) |  |  |
| 4030422A | Squamous Cell Carcinoma | 730 C→A | 4 | R244R (CGA→AGA) | Polymorphism | Heterozygous |
| 4030422B | Normal lung tissue | 730 C→A | 4 | R244R (CGA→AGA) | Polymorphism | Heterozygous |

TABLE 2

Lung pathologies in Mig-6 deficient and control
mice between 5 and 13 months of age

|  | Mig-6$^{+/+}$ (n = 17) | Mig-6$^{+/-}$ (n = 31) | Mig-6$^{-/-}$ (n = 29) |
|---|---|---|---|
| Lung adenoma or adenocarcinoma | 0 | 1 | 4 |
| Bronchi and bronchiole epithelial hyperplasia | 1 | 0 | 11 |

Figures 12A, 12B:
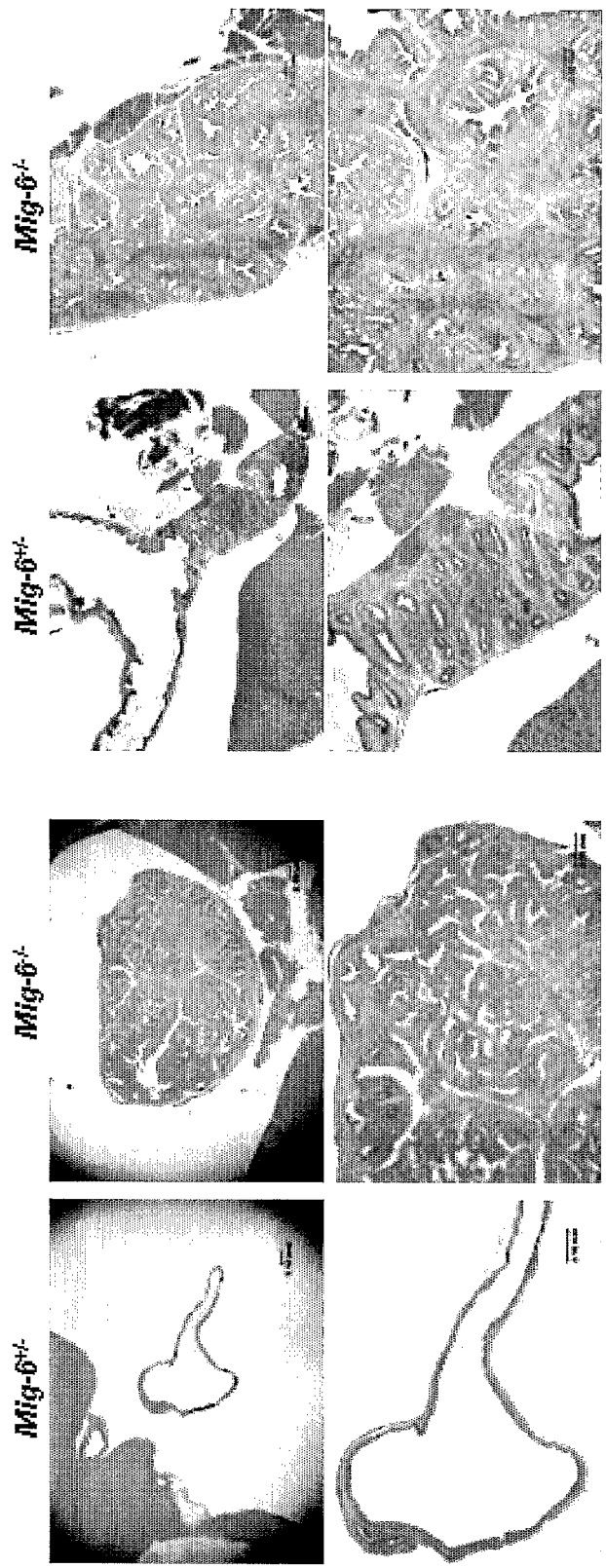
FIG. 12A-12C: Gallbladder and bile duct cancers in Mig-6-deficient mice.
Figure 12C:
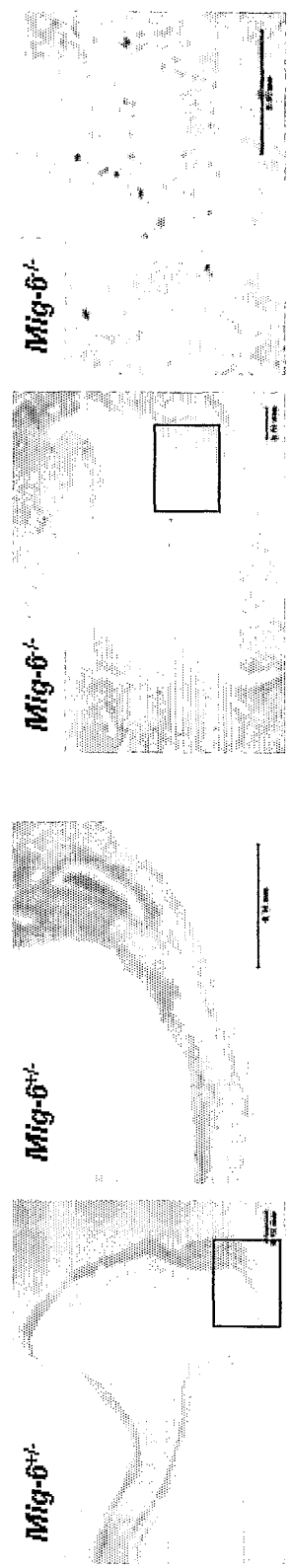

In addition to lung cancer, gallbladder and/or bile duct neoplasms were also observed, which ranged from epithelial hyperplasia to carcinoma in several other Mig-6$^{-/-}$ animals (FIG. 12A, 12B and Table 3). Immunohistochemical staining of the tissues for the presence of PCNA revealed increased numbers of proliferating cells within the mutant gallbladder (FIG. 12C). These results implicate a loss of Mig-6 function in lung, gallbladder, and bile duct carcinogenesis and are consistent with the evidence that Mig-6 is a tumor suppressor gene.

TABLE 3

Cases of gallbladder and bile duct carcinogenesis in Mig-6$^{-/-}$ mice

| Genotype | Age (months) | Pathology |
|---|---|---|
| Mig-6$^{-/-}$ | 2 | Adenocarcinoma of bile ducts (low grade) |
|  | 12 | One adenocarcinoma and one adenoma |
|  | 6.5 | Adenocarcinoma of bile ducts (low grade) |
| Mig-6$^{+/-}$ | 12 | Dilatation of gallbladder |
|  | 12 | Cystic hyperplasia |
|  | 6.5 | Mild dilatation and hyperplasia of gallbladder |
| Mig-6$^{+/+}$ | 12 | Gallbladder a bit dilated and a little hyperplasia |
|  | 12 | Normal |
|  | 6.5 | Normal |

Discussion of Examples IV-VIII

Mig-6 localizes in human chromosome 1p36, a locus that is known to harbor putative tumor suppressor genes. Allelic imbalance of chromosome 1p36 is one of the most frequent genetic alterations observed in a range of human cancers (Ragnarsson et al., Br. J. Cancer 79:1468-74, 1999; Thiagalingam et al., Curr. Opin. Oncol. 14:65-72., 2002). Linkage analyses using microsatellite markers revealed deletions of 1p36 in nearly 50% of primary human lung cancers (Nomoto et al., 2000, supra). Similar results were also reported in human lung cancer cell lines, including both NSCLC and SCLC (Girard et al., Cancer Res. 60:4894-4906, 2000; Fujii et al., supra; Virmani et al., Genes Chromosomes Canc 21:308-19, 1998). The evidence indicating the presence of a tumor suppressor gene in 1p36 also comes from studies of mouse lung cancer. Loss of heterozygosity in the region of mouse chromosome 4, which is syntenic to human chromosome 1p36, has been observed frequently in spontaneous and carcinogen-induced mouse lung adenocarcinomas (Herzog et al., 1995, 2002, supra; Sargent et al., Cancer Res. 62:1152-57, 2002). The search for the responsible gene in 1p36 has not been successful. The p53 homologue, p73, is found in this locus, and has been rigorously tested. However, no mutations in the p73 gene have been identified thus far, although frequent allelic imbalances have been observed at this locus (Nomoto et al., 1998, supra). In addition, p73 expression has been found to increase rather than decrease in lung cancer (Mai et al., Cancer Res. 58:2347-49, 1998; Tokuchi et al., Br. J. Cancer 80:1623-29, 1999), and no spontaneous tumors have been observed in p73-deficient mice (Yang et al., Nature 404:99-103 2000). The foregoing all point to the presence of other unidentified tumor suppressor genes in 1p36.

For many reasons, it is plausible to consider Mig-6 as a 1p36 lung cancer tumor suppressor gene. First, it resides at 1p36.12-36.33, in the locus that is considered a hot spot of allelic imbalance for lung cancer (Fujii et al., supra; Girard et al., supra; Nomoto et al., 2000, supra). Further, as shown here, disruption of the mouse Mig-6 gene, which localizes to the 1p36 syntenic region in mouse chromosome 4, results in lung carcinogenesis (FIG. 11A-11H). Importantly, loss-of-function mutations in the Mig-6 gene in human lung cancer cell lines are disclosed herein.

Mig-6 is normally expressed in lung and plays a role in mechanical stress pulmonary ventilation (Makkinje et al., supra). Mig-6 is also a negative regulator of RTK signaling from growth factors like EGF (Fiorentino et al., supra) and HGF/SF (FIGS. 8A-8D and 9A-9C; Pante et al., J. Cell Biol. 171:337-48, 2005), the receptors for which are known to play important roles in lung malignancy (Birchmeier et al., Nat. Rev. Mol. Cell Biol. 4:915-25, 2003; Ma et al., Cancer Res. 63:6272-81, 2003; Ma et al., Cancer Res. 65:1479-88, 2005; Paez et al., Science 304:1497-1500.2004; Stephens et al., Nature 431:525-26 2004; Zochbauer-Muller et al., supra). All this evidence supports the present conclusion that Mig-6 is a tumor suppressor gene.

Likewise, according to this invention, Mig-6 also functions as a tumor suppressor in other organs, since animals with Mig-6 deficiency also develop gallbladder and bile duct cancers (FIG. 12A-12C and Table 3). Moreover, it has recently been reported that Mig-6 expression is lost in ErbB2-amplified breast carcinomas (Anastasi et al., 2005, supra).

Like other tumor suppressor genes involved in lung carcinogenesis (Kohno et al., Carcinogenesis 20, 1403-10, 1999; Zochbauer-Muller et al., supra), the inactivation of Mig-6 may result from genetic or epigenetic changes. LOH seems to be the case for the NCI-H322M human lung adenocarcinoma cell line, which is characterized by a single nonsense point mutation in one allele of the Mig-6 gene, and deletion of the other allele (See World Wide Web URL ncbi.nlm.nih.gov/sky/skyweb.cgi).

Inactivation of Mig-6 appears to involve another mechanism in NCI-H226 human lung squamous cell carcinoma cells. In addition to the missense mutation identified in the Mig-6 coding region, regulation of Mig-6 gene expression by either EGFR or Met was defective. Thus, there are at least two bases for this dysregulation of Mig-6 by receptor signaling: (1) either a deletion or other mutation occurs in the promoter regulatory region or (2) the promoter silencing is epigenetic. A similar mechanism could explain the loss of Mig-6 expression in ErbB2-amplified breast carcinomas (Anastasi et al., 2005, supra).

The present inventors considered the question of what might be the role of Mig-6 in normal lung function and during lung carcinogenesis. Mig-6 is a scaffolding protein involved in receptor signal transduction. The expression of Mig-6 is induced by EGF, whose signaling plays an important role in normal lung development (Miettinen et al., Nature 376:337-41, 1995; Miettinen et al., Dev. Biol. 186:224-36, 1997). Like many other tyrosine kinase receptors, EGF receptor signaling needs to be attenuated after activation. Constitutive activation is deleterious to normal lung epithelial cells and can lead to carcinogenesis (Paez et al., supra; Stephens et al., supra; Zochbauer-Muller et al., supra). Mig-6 interacts with the ErbB receptor family and negatively regulates EGF signaling (Fiorentino et al., supra; Anastasi et al., 2003, supra; Xu et al., supra), thereby providing, through negative feedback, a mechanism for fine-tuning EGF signaling shortly after its activation. Mig-6 deficiency caused by a mutation or failure of feedback regulation would then lead to inappropriate activation of EGF signaling and other signaling as well (such as HGF/SF-Met signaling). As described above, prolonged receptor tyrosine kinase-mediated MAPK activation occurred in Mig-6-deficient cells (FIGS. 9A and 9B).

Overexpression of Mig-6 inhibits ErbB2-mediated transformation of NIH 3T3 cells (Fiorentino et al., supra). Mig-6 would provide a checkpoint for normal cell proliferation in certain tissues, because disruption of Mig-6 led to uncontrolled proliferation of cells (as revealed by PCNA staining in gallbladder epithelium; FIG. 12A-12C) and in joint tissues (Examples I and II).

A role for Mig-6 in cell cycle regulation has also been implied, as its expression is regulated during the normal cell cycle progression (Wick et al., *Exp. Cell Res.* 219:527-35, 1995). Moreover, many stress stimuli also induce the expression of Mig-6, which activates SAPK/JNK (Makkinje et al., supra). SAPK/JNK activity is usually suppressed in order for transformed cells to escape SAPK/JNK-dependent apoptosis and become tumorigenic (Benhar et al., *EMBO Rep.* 3:420-5, 2002; Davis, *Cell* 103:239-52, 2000). Inactivation of Mig-6 may result in an inability to induce SAPK/JNK-dependent apoptosis which would lead to immortalization of cells.

In addition, Mig-6 comprises several well-known protein-protein interaction motifs, including a Cdc42/Rac interactive binding (CRIB) domain, a Src homology 3 (SH3) domain binding motif, and a 14-3-3 interacting motif (Makkinje et al., supra). Although it is still not clear how Mig-6 interacts with its partner proteins and exerts its function during various cellular processes, based on the present results, abnormal regulation of Mig-6 reveals its activity as a tumor suppressor gene, and loss of its activity contributes to the initiation of lung carcinogenesis as well as other cancers.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A knockout mouse the genome of which is manipulated to comprise a disruption of one or both alleles of the mig-6 gene, wherein when both alleles are disrupted, the mouse exhibits joint abnormalities characteristic of osteoarthritis as compared to a wild type mouse in which the mig-6 gene is not disrupted.

2. The knockout mouse of claim 1 which is homozygous for the mig-6 gene disruption.

3. The knockout mouse of claim 1 wherein the said disruption of both alleles of the mig-6 gene further results in said mouse exhibiting increased tumorigenesis in the lung, gall bladder and/or bile duct compared to said wild type mouse.

4. A conditional knockout mouse the genome of which is manipulated to comprise at least one mutant mig-6 allele that comprises, from 5' to 3', a first loxP site, a first FLP recombinase target (FRT) sequence, a lacZ DNA coding sequence, PGK-Neo cassette, a second FRT sequence, a human Mig-6 cDNA coding sequence and a second loxP site, such that (a) when a FLP recombinase is provided via a genetic cross with a FLP recombinase-expressing mouse, the ends of the first FRT and the second FRT are exchanged such that the LacZ and PGK-Neo sequence are deleted and the human Mig-6 cDNA coding sequence is rescued; and (b) when a Cre-recombinase is provided via a genetic cross with a Cre-expressing mouse, the Mig-6 coding sequence is deleted resulting in the absence of Mig-6 cDNA, and the mouse exhibits abnormalities characteristic of osteoarthritis as compared to wild type mouse in which the Mig-6 coding sequence is not deleted.

5. The conditional knockout mouse of claim 4, wherein the Cre recombinase is under the control of a tissue specific promoter, so that the deletion in (b) occurs in a tissue-specific manner.

6. A cell derived or isolated from the knockout mouse of claim 1.

7. A cell derived or isolated from the conditional knockout mouse of claim 4.

8. The cell of claim 6 selected from the group consisting of multipotent stem cells, lineage-committed stem cells, tumor cells, chondrocytes, and chondrocyte precursors.

9. A Mig-6 DNA knockout mouse comprising a selectable marker sequence flanked by DNA sequences homologous to mig-6 genomic DNA, wherein when the selectable marker sequence flanked by DNA sequences is introduced into said mouse or an ancestor of said mouse at an embryonic stage, the selectable marker sequence disrupts the mig-6 gene in said embryonic cell and mouse that results in said mouse exhibiting (a) joint abnormalities characteristic of osteoarthritis and (b) enhanced tumorigenesis of lung, gall bladder and/or bile ducts.

10. The Mig-6 DNA knockout mouse of claim 9, further comprising, 5' to 3',
   (a) a first mig-6 genomic DNA fragment;
   (b) a neo cassette comprising a constitutive promoter; (c) a second mig-6 genomic DNA fragment which is 3' from said first mig-6 genomic DNA fragment in murine mig-6 genomic DNA, and (d) optionally, a thymidine kinase cassette.

11. A Mig-6 DNA knockout construct, comprising, 5' to 3',
   (a) a first mig-6 genomic DNA fragment that is an approximately 5 kb polynucleotide most of which is located upstream of exon 2 in genomic DNA but includes at it's 3' end a sequence from exon 2,
   (b) a PGK-I promoter, and
   (c) a second mig-6 genomic DNA fragment that is an approximately 3 kb polynucleotide located downstream of exon 4.

12. The mig-6 DNA knockout construct of claim 11, wherein the first mig-6 genomic DNA fragment has the sequence SEQ ID NO: 19 and the second Mig 6 genomic DNA fragment has the sequence SEQ ID NO.20.

13. A vector comprising the Mig-6 DNA knockout construct of claim 11.

14. A Mig-6 DNA conditional knockout construct comprising, in the 5' to 3' direction: (a) an approximately 5 kb mig-6 genomic DNA fragment most of which is located upstream of exon 2 in genomic DNA but includes at it's 3' end a sequence from exon 2;
   (b) a first loxP site;
   (c) a first FRT sequence;
   (d) a lacZ DNA coding sequence; (e) a PGK-Neo cassette;
   (f) a second FRT sequence;
   (g) a second human Mig-6 cDNA coding sequence;
   (h) a second loxP site;

(i) a third mig-6 genomic DNA fragment that is an approximately 3 kb polynucleotide located downstream of exon 4; and (j) optionally an HSV thymidine kinase cassette.

15. A method of producing the knockout mouse of claim 1 which is heterozygous, the method comprising the steps of:
    (a) transforming a mouse embryonic stem cell with a knockout construct comprising a selectable marker sequence flanked by DNA sequences homologous to mig-6, genomic DNA, thereby producing a transformed embryonic stem cell;
    (b) introducing the transformed embryonic stem cell into a mouse blastocyst; (c) implanting blastocyst comprising the transformed embryonic cell into a pseudopregnant female mouse;
    (d) allowing the blastocyst to undergo fetal development to term; and
    (e) allowing the developed fetus to be born as said heterozygous knockout mouse, wherein the knockout mouse so produced exhibits, when said disrupted mig-6 is in a homozygous state, (i) joint abnormalities characteristic of osteoarthritis and (ii) enhanced tumorigenesis of lung, gall bladder and/or bile ducts.

16. The method of claim 15 further comprising;
    (f) testing the mouse after step
    (e) to verify that its genome comprises a disrupted mig-6 gene in at least one allele.

17. A method for producing a knockout mouse the genome of which is homozygous for a disruption of the mig-6 gene, the method comprising:
    (a) interbreeding heterozygous mice produced in accordance with claim 15; and
    (b) selecting offspring in which the disruption of the mig-6 gene is homozygous.

18. A method for selecting a candidate agent for use in the treatment or prevention of osteoarthritis, comprising:
    (a) administering a candidate agent to a knockout mouse of claim 1, wherein said disruption of mig-6 results in joint abnormalities characteristic of osteoarthritis;
    (b) measuring the response of said knockout mouse to said agent; and
    (c) selecting an agent based on its ability to decrease or prevent symptoms of osteoarthritis in said knockout mouse.

19. A method of determining whether a compound or agent prevents or treats symptoms of osteoarthritis, comprising:
    (a) administering a compound or agent to the knockout mouse of claim 1 and
    (b) determining whether the compound prevents or treats said symptoms.

20. A method for evaluating the effect of a test agent or treatment for its ability to delaying development of or treat a human tumor or cancer, comprising
    (a) administering the test agent to, or performing the treatment on, the knockout mouse of claim 1; (b) evaluating the time of appearance, rate of development, growth, or metastasis of tumors in said mice compared to said knockout mice not given said agent or treatment;
    (c) comparing results obtained in step (b) to the time of appearance, rate of development, growth, or metastasis of tumors in said knockout mice which have not been given said agent or treatment, wherein a significant delay in appearance, attenuation of development, growth or metastasis of said tumors in (b) compared to (c) indicates that the agent or treatment has the ability to delay development or treat said tumor or cancer.

21. The method of claim 20 wherein the human tumor or cancer is carcinoma.

22. The method of claim 21 wherein the carcinoma is lung carcinoma.

23. The method of claim 20 wherein the tumors being evaluated in said mice are lung tumors, gall bladder tumors or bile duct tumors.

* * * * *

SEQUENCE LISTING

```
<160> NUMBER OF SEQ ID NOS: 22

<210> SEQ ID NO 1
<211> LENGTH: 24
<212> TYPE: DNA
<213> ORGANISM: Artificial Sequence
<220> FEATURE:
<223> OTHER INFORMATION: primer

<400> SEQUENCE: 1
gacaatttga gcaacttgac ttgg                                         24

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
ggttacttag ttgttgcagg taag                                         24

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
ccttctatcg cctttcttgac g                                           21

<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4
cagaagttac atgggatgaa tgg                                          23
```

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
tgaacacaaa ctgcgtgtct cac                                    23

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
tccagtatga ctccactcac g                                      21

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
acaacctggt cctcagtgta g                                      21

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
tcttccaccg ttgccaatc                                         19

<210> SEQ ID NO 9
<211> LENGTH: 23
<212> TYPE: DNA
<213> ORGANISM: Artificial Sequence
<220> FEATURE:
<223> OTHER INFORMATION: primer

<400> SEQUENCE: 9
ttccacctca cagtctgtgt cat                                    23

<210> SEQ ID NO 10
<211> LENGTH: 16
<212> TYPE: DNA
<213> ORGANISM: Artificial Sequence
<220> FEATURE:
<223> OTHER INFORMATION: primer

<400> SEQUENCE: 10
ctgaagccct ctctct                                            16

<210> SEQ ID NO 11
<211> LENGTH: 22
<212> TYPE: DNA
<213> ORGANISM: Artificial Sequence
<220> FEATURE:
<223> OTHER INFORMATION: primer

```
<400> SEQUENCE: 11
ttctctcatc tcttctacct cc                                              22

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
taatgctgga ggacaagcta ac                                              22

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
ttcactcagg aagaaagctg tg                                              22

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
ctctgcactt caatcaaact gg                                              22

<210> SEQ ID NO 15
<211> LENGTH: 1386
<212> TYPE: DNA
<213> ORGANISM: Mus musculus Mig-6

<400> SEQUENCE: 15
atgtcaacag caggagttgc tgctcaggat attcgagtcc cattaaaaac tggatttctc      60
cataatggtc aggccttggg gaatatgaag tcctgctggg gcagtcacag tgagtttgaa     120
aataactttt taaatattga tccaataacc atggcctaca atctgaactc ccctgctcag     180
gagcacctaa caactgttgg atgtgctgct cggtctgctc cagggagcgg ccacttcttt     240
gcagagtgtg gtccatctcc aaggtcaagc ttgcccccte ttgttatctc accaagtgaa     300
agctcgggac agcgtgaaga ggatcaagtt atgtgtggtt ttaagaaact ctcagtgaat     360
ggggtctgca cttccacacc tccacttaca cccattaaaa gctgcccttc cccttttccc     420
tgtgcggctc tgtgtgatcg gggttctcgg ccgctcccgc cactgcccat ctctgaagac     480
ctatgtgtgg atgaggccga cagtgaggta gagcttctaa ccaccagctc agacacagac     540
ttgcttttag aagactctgc gccttcagat ttcaaatacg atgctcctgg caggcgcagc     600
ttccgtgggt gcggccagat caactatgca tattttgaca gcccaactgt ttctgtggca     660
gatcttagct gtgcatctga ccagaacaga gttgttccag acccaaaccc tccccacct     720 caaagccatc gcagattaag gaggtctcac tcaggaccag ctgggtcatt taacaagcca     780
gccattcgga tatctagctg cacacacaga gcttctccta gctctgatga agacaagcct     840
gaggtccctc ccagggttcc tatacctcct aggccagcaa agccagacta tagacggtgg     900
tcagcagaag tgacctccaa cacctacagt gatgaagata ggcctccaa agtcccccg     960
```

-continued

```
agagaacctt tgtctcggag taactcccgt accccaagtc ctaaaagcct tccgtcttac   1020
ctcaatgggg tcatgccccc aacacagagc ttcgctcctg accccaagta tgtcagcagc   1080
aaagccctgc agagacagag cagcgaagga tctgccaaca aggttccttg catcctgccc   1140
attattgaaa atgggaagaa ggttagctca acgcattatt acttactacc tgagaggcca   1200
ccgtacctgg acaaatatga aaagtatttt aaggaagcag aagaaacaaa cccaagcacc   1260
caaattcagc cattacctgc tgcctgtggt atggcctctg ccacagaaaa gctggcctcc   1320
agaatgaaaa tagatatggg tagccacggg aagcgcaaac acttatccta cgtggtttct   1380
ccataa                                                               1386
```

<210> SEQ ID NO 16
<211> LENGTH: 461
<212> TYPE: PRT
<213> ORGANISM: Mus musculus Mig-6

<400> SEQUENCE: 16

```
Met Ser Thr Ala Gly Val Ala Ala Gln Asp Ile Arg Val Pro Leu Lys
1               5                   10                  15

Thr Gly Phe Leu His Asn Gly Gln Ala Leu Gly Asn Met Lys Ser Cys
            20                  25                  30

Trp Gly Ser His Ser Glu Phe Glu Asn Asn Phe Leu Asn Ile Asp Pro
        35                  40                  45

Ile Thr Met Ala Tyr Asn Leu Asn Ser Pro Ala Gln Glu His Leu Thr
    50                  55                  60

Thr Val Gly Cys Ala Ala Arg Ser Ala Pro Gly Ser Gly His Phe Phe
65                  70                  75                  80

Ala Glu Cys Gly Pro Ser Pro Arg Ser Ser Leu Pro Pro Leu Val Ile
                85                  90                  95

Ser Pro Ser Glu Ser Ser Gly Gln Arg Glu Glu Asp Gln Val Met Cys
            100                 105                 110

Gly Phe Lys Lys Leu Ser Val Asn Gly Val Cys Thr Ser Thr Pro Pro
        115                 120                 125

Leu Thr Pro Ile Lys Ser Cys Pro Ser Pro Phe Pro Cys Ala Ala Leu
    130                 135                 140

Cys Asp Arg Gly Ser Arg Pro Leu Pro Pro Leu Pro Ile Ser Glu Asp
145                 150                 155                 160

Leu Cys Val Asp Glu Ala Asp Ser Glu Val Glu Leu Leu Thr Thr Ser
                165                 170                 175

Ser Asp Thr Asp Leu Leu Leu Glu Asp Ser Ala Pro Ser Asp Phe Lys
            180                 185                 190

Tyr Asp Ala Pro Gly Arg Arg Ser Phe Arg Gly Cys Gly Gln Ile Asn
        195                 200                 205

Tyr Ala Tyr Phe Asp Ser Pro Thr Val Ser Val Ala Asp Leu Ser Cys
    210                 215                 220

Ala Ser Asp Gln Asn Arg Val Val Pro Asp Asn Pro Pro Pro Pro
225                 230                 235                 240

Gln Ser His Arg Arg Leu Arg Arg Ser His Ser Gly Pro Ala Gly Ser
                245                 250                 255

Phe Asn Lys Pro Ala Ile Arg Ile Ser Ser Cys Thr His Arg Ala Ser
            260                 265                 270

Pro Ser Ser Asp Glu Asp Lys Pro Glu Val Pro Pro Arg Val Pro Ile
        275                 280                 285

Pro Pro Arg Pro Ala Lys Pro Asp Tyr Arg Arg Trp Ser Ala Glu Val
    290                 295                 300
```

```
Thr Ser Asn Thr Tyr Ser Asp Glu Asp Arg Pro Pro Lys Val Pro Pro
305                 310                 315                 320

Arg Glu Pro Leu Ser Arg Ser Asn Ser Arg Thr Pro Ser Pro Lys Ser
            325                 330                 335

Leu Pro Ser Tyr Leu Asn Gly Val Met Pro Pro Thr Gln Ser Phe Ala
            340                 345                 350

Pro Asp Pro Lys Tyr Val Ser Ser Lys Ala Leu Gln Arg Gln Ser Ser
            355                 360                 365

Glu Gly Ser Ala Asn Lys Val Pro Cys Ile Leu Pro Ile Ile Glu Asn
370                 375                 380

Gly Lys Lys Val Ser Ser Thr His Tyr Tyr Leu Leu Pro Glu Arg Pro
385                 390                 395                 400

Pro Tyr Leu Asp Lys Tyr Glu Lys Tyr Phe Lys Glu Ala Glu Glu Thr
                405                 410                 415

Asn Pro Ser Thr Gln Ile Gln Pro Leu Pro Ala Ala Cys Gly Met Ala
            420                 425                 430

Ser Ala Thr Glu Lys Leu Ala Ser Arg Met Lys Ile Asp Met Gly Ser
            435                 440                 445

His Gly Lys Arg Lys His Leu Ser Tyr Val Val Ser Pro
450                 455                 460
```

<210> SEQ ID NO 17
<211> LENGTH: 1389
<212> TYPE: DNA
<213> ORGANISM: Homo sapiens Mig-6

<400> SEQUENCE: 17

```
atgtcaatag caggagttgc tgctcaggag atcagagtcc cattaaaaac tggatttcta      60
cataatggcc gagccatggg gaatatgagg aagacctact ggagcagtcg cagtgagttt     120
aaaaacaact ttttaaatat tgacccgata accatggcct acagtctgaa ctcttctgct     180
caggagcgcc taataccact tgggcatgct tccaaatctg ctccgatgaa tggccactgc     240
tttgcagaaa atggtccatc tcaaaagtcc agcttgcccc tcttcttat tccccccaagt     300
gaaaacttgg gaccacatga agaggatcaa gttgtatgtg gttttaagaa actcacagtg     360
aatggggttt gtgcttccac ccctccactg acacccataa aaaactcccc ttcccttttc     420
ccctgtgccc ctctttgtga acggggttct aggcctcttc accgttgcc aatctctgaa     480
gccctctctc tggatgacac agactgtgag gtggaattcc taactagctc agatacagac     540
ttccttttag aagactctac actttctgat ttcaaatatg atgttcctgg caggcgaagc     600
ttccgtgggt gtggacaaat caactatgca tattttgata ccccagctgt ttctgcagca     660
gatctcagct atgtgtctga ccaaaatgga ggtgtcccag atccaaatcc tcctccacct     720
cagacccacc gaagattaag aaggtctcat tcgggaccag ctggctcctt taacaagcca     780
gccataagga tatccaactg ttgtatacac agagcttctc ctaactccga tgaagacaaa     840
cctgaggttc cccccagagt tcccataccc cctagaccag taaagccaga ttatagaaga     900
tggtcagcag aagttacttc gagcacctat agtgatgaag acaggcctcc caaagtaccg     960
ccaagagaac ctttgtcacc gagtaactcg cgcacaccga gtcccaaaag ccttccgtct    1020
tacctcaatg gggtcatgcc cccgacacag agctttgccc ctgatcccaa gtatgtcagc    1080
agcaaagcac tgcaaagaca gaacagcgaa ggatctgcca gtaaggttcc ttgcattctg    1140
cccattattg aaaatgggaa gaaggttagt tcaacacatt attacctact acctgaacga    1200
ccaccatacc tggacaaata tgaaaaattt tttagggaag cagaagaaac aaatggaggc    1260
```

-continued

```
gcccaaatcc agccattacc tgctgactgc ggtatatctt cagccacaga aaagccagac    1320
tcaaaaacaa aatggatct gggtggccac gtgaagcgta aacatttatc ctatgtggtt     1380
tctccttag                                                            1389
```

```
<210> SEQ ID NO 18
<211> LENGTH: 462
<212> TYPE: PRT
<213> ORGANISM: Homo sapiens Mig-6

<400> SEQUENCE: 18

Met Ser Ile Ala Gly Val Ala Ala Gln Glu Ile Arg Val Pro Leu Lys
1               5                   10                  15

Thr Gly Phe Leu His Asn Gly Arg Ala Met Gly Asn Met Arg Lys Thr
            20                  25                  30

Tyr Trp Ser Ser Arg Ser Glu Phe Lys Asn Asn Phe Leu Asn Ile Asp
        35                  40                  45

Pro Ile Thr Met Ala Tyr Ser Leu Asn Ser Ser Ala Gln Glu Arg Leu
    50                  55                  60

Ile Pro Leu Gly His Ala Ser Lys Ser Ala Pro Met Asn Gly His Cys
65                  70                  75                  80

Phe Ala Glu Asn Gly Pro Ser Gln Lys Ser Ser Leu Pro Pro Leu Leu
                85                  90                  95

Ile Pro Pro Ser Glu Asn Leu Gly Pro His Glu Glu Asp Gln Val Val
            100                 105                 110

Cys Gly Phe Lys Lys Leu Thr Val Asn Gly Val Cys Ala Ser Thr Pro
        115                 120                 125

Pro Leu Thr Pro Ile Lys Asn Ser Pro Ser Leu Phe Pro Cys Ala Pro
    130                 135                 140

Leu Cys Glu Arg Gly Ser Arg Pro Leu Pro Pro Leu Pro Ile Ser Glu
145                 150                 155                 160

Ala Leu Ser Leu Asp Asp Thr Asp Cys Glu Val Glu Phe Leu Thr Ser
                165                 170                 175

Ser Asp Thr Asp Phe Leu Leu Glu Asp Ser Thr Leu Ser Asp Phe Lys
            180                 185                 190

Tyr Asp Val Pro Gly Arg Arg Ser Phe Arg Gly Cys Gly Gln Ile Asn
        195                 200                 205

Tyr Ala Tyr Phe Asp Thr Pro Ala Val Ser Ala Ala Asp Leu Ser Tyr
    210                 215                 220

Val Ser Asp Gln Asn Gly Gly Val Pro Asp Pro Asn Pro Pro Pro Pro
225                 230                 235                 240

Gln Thr His Arg Arg Leu Arg Arg Ser His Ser Gly Pro Ala Gly Ser
                245                 250                 255

Phe Asn Lys Pro Ala Ile Arg Ile Ser Asn Cys Cys Ile His Arg Ala
            260                 265                 270

Ser Pro Asn Ser Asp Glu Asp Lys Pro Glu Val Pro Pro Arg Val Pro
        275                 280                 285

Ile Pro Pro Arg Pro Val Lys Pro Asp Tyr Arg Arg Trp Ser Ala Glu
    290                 295                 300

Val Thr Ser Ser Thr Tyr Ser Asp Glu Asp Arg Pro Lys Val Pro
305                 310                 315                 320

Pro Arg Glu Pro Leu Ser Pro Ser Asn Ser Arg Thr Pro Ser Pro Lys
                325                 330                 335

Ser Leu Pro Ser Tyr Leu Asn Gly Val Met Pro Pro Thr Gln Ser Phe
            340                 345                 350
```

```
Ala Pro Asp Pro Lys Tyr Val Ser Ser Lys Ala Leu Gln Arg Gln Asn
            355                 360                 365

Ser Glu Gly Ser Ala Ser Lys Val Pro Cys Ile Leu Pro Ile Ile Glu
        370                 375                 380

Asn Gly Lys Lys Val Ser Ser Thr His Tyr Tyr Leu Leu Pro Glu Arg
385                 390                 395                 400

Pro Pro Tyr Leu Asp Lys Tyr Glu Lys Phe Phe Arg Glu Ala Glu Glu
                405                 410                 415

Thr Asn Gly Gly Ala Gln Ile Gln Pro Leu Pro Ala Asp Cys Gly Ile
            420                 425                 430

Ser Ser Ala Thr Glu Lys Pro Asp Ser Lys Thr Lys Met Asp Leu Gly
        435                 440                 445

Gly His Val Lys Arg Lys His Leu Ser Tyr Val Ser Pro
    450                 455                 460

<210> SEQ ID NO 19
<211> LENGTH: 5061
<212> TYPE: DNA
<213> ORGANISM: Mus musculus Mig-6

<400> SEQUENCE: 19
aggtcatcta gtggaggcaa gaacacacaa accatccttt ctttgcatcc ttttggacag      60
catttatgaa atatttgctg aagctatcac atcttacttg attccatgca tgagcactgt     120
agttgtgttt tattttagaa gtcattcatg cagctaatat aaaggcgagt tctgcttttc     180
tatggtaaac ttataacaaa gaagtttcct tagcctggct cccttctttc cttaacccca     240
aatcatagct tttaaaatta aatctgaaaa actttgaatt caggcctttg ctcttgaaat     300
atctgtgcaa acgcccttttt gctttcagta ataagtgta gattatatca cctgcttgat     360
tcaaagacac agaagagtct tgctgcgtt taacagtttg ttaccttaac ttccacaaac     420
caggaagaca catgctcgct atttacagcc aaaatgtgta agacattgac tagaagtatg     480
atggatccca tgatttttag atcctcctgt gtaacaggat aatgctgagt gcaggtagat     540
gctaagtcat ttttctccgt tattaattta agtccacaac acagcaaata aaactgattt     600
ccatttcctc tcattttctc ggcgagcata ggaagtagta tatttgagga agatccaaag     660
taatgaaagg tggcaacgtt tctaatcggt gtcttccgat aaacttggct ctatagtgaa     720
gttgtcttcc ctgattatgg aagtagctag gtaggcaatt gttaaacgca gctggaaaga     780
ccatttatca ctctgaataa acagaaatca ggttctagaa ccagattgaa agaaggaaat     840
tacatcacac tcttaaataa ggaagcactg ggcagaactg gatgagttgt aagacaaaaa     900
tgtgcccctc ctcctctcat ggactgctcc tgagatgtat taataagatc ttgtggcaag     960
gtaagcatat ctaggttact gccttaaggt agcctagctt tgtgtgttaa agcagtttca    1020
aagtaagtat tttcaagata aagacatgtg agttcacctt agaaagtgtg cagtgtgcta    1080
ttggtatatt gtgactttttt tatttttaaa gtgtcaataa aacaaagata gatagattac    1140
aagcccaaag gaacagtatg taagaaaagg tgaaaagtct gtagtaagaa gccattgaga    1200
aagccacgcc agcagccatt gatgctgacc ttttactcag ccacacactg tcactgagga    1260
cccagaaggt gaactcggga tattctaaat gtgttaggtt attacaggcc taacttacat    1320
acagtacatt cagagttgat ccctgaacaa atctgtgctt ttcccttagc tttcctcttc    1380
agcctgggga gaatcttaca taattacatt ttaaaacatg agatggctat tttctcagtt    1440
cacttaatat gatctacagg ggggaggaaa tgtcaggcac cagtcctaga tttggagggt    1500
```

```
aggaggggaa cctggcgtag cacagaatag ctagactggc cctggatttt aataacagga   1560
ggggcttgtt gaaggagcac agtgtgagaa caagccttaa agctcaaagc agctagagct   1620
gaacagggca ggttagggaa aggccattgt gaggtctttt gtgccagctg aggcgctttt   1680
agaggctttt acaggttctt ttgggggtgg caattaagga atattgattt gatcctgttg   1740
gctgtagtat ggtttaaata tcttcagact aaaaattgga accaatagga gaaggaagag   1800
agttttgaga agaagtttaa aaactttgta tggatgttgg cagttgaatg tatattggcc   1860
ttaactcagg ctcacagtgg taggtacctc aggaagtatg atcctcttgg atcaagaaag   1920
ggtgggaggt aagttaagag acccaaagaa tcgggtttgg aacttgtgag ataccagagg   1980
cccatccaag tggaaagata atcaccagac agacaataag aaatgcacag tggaagtgga   2040
agtcagactg cacgtacctc cttaggaact gtctgtggat ttgaagccat agaaatgaat   2100
taaagatttt aagagcaaa atcttaaagt taaaatatag tgcaattagc agaaatgagg   2160
tactggtatt taactacatt ttggtcactt cacattaaaa ttgttttatg attatgtaaa   2220
ttgttatact gaaggttatt tgggtcctgg tttacacagt gaacctgtat cgacattcat   2280
tttgatcttg gctttcataa tagaatacca tattgtactt ttaaatattg acactcatac   2340
ataaatgtat ctttgcagtt agtttcttta tgaattgaaa agtagagcta gttttacagt   2400
tatgaggact tggatacaat tgtaaacact gcagcattag ttgaatttta cttgagcaaa   2460
ctgtgttgtt ttattggcta gagtgatttc tctgcctcca ccaggattat acaacctgaa   2520
tgctggcttg gcttttttg tcttgtgagg taggagactt ccaaacagtt ttctaacata   2580
accttagttt aacatcagga gggatgagag agtgtatgtg tatctaagcc ttaaacctgg   2640
ggcatgttgc tcttttgagt tttacagcct gaagttattt tccaaacgat gagagcacag   2700
cagttatatt gccctctttg cttctgccat gcaagcaagt aggaagttca gatagtttca   2760
taacatggcc cattcacaat tccccattga aatttagagg caggtcacct tctatgaata   2820
cacaaagaca actattgtgg tcagaagtga gctggcttag tgaacacaat tcttttata   2880 ctaaaaaaaa aaaatttcct taagaaagct aacaagtagg tgatggaaca atgaataaaa   2940 aataacttt tctaaaacat ataaataatt ttaagtgacc actgaagtgt aagtttagga   3000
ttccaaggca acttgagcag aggcgatagt tacacaatca ctctgttgaa agctaagatg   3060
tagatggcac tgggaggctg acacagtaat tactagtagt atttgttggc tggcctacag   3120
gtgggggctg ggcctccctc gtccccgca gcattgtcct gtaatcggga tgaaccatct   3180
tccaacgtgt gctttcaaac cacttaacca ccacagtcgt cctcccatct cgcctgcctt   3240
tcattttcat attcacagra tccttttccct gtagtctctc agtgtttgtg actatttaga   3300
aagggcttga tacaccctgg ctaagtatac actgggagag gctagcctct ttaaaaatgt   3360
gttttttaaa ttactcaatg gtaaataaca catccgtttt atttcagtaa tctaaaaaac   3420
caagactcaa agacctaata ctaaggttcc ttaagtgacg gagagactgg tttttcaaaa   3480
caaggtttga ctctttgaaa taaataact gccttgtgta ttaaaacagc tgcttttgta   3540
aacatctatg gggtatttt ttagattagc ttaaaaaagt aagaacccct atgccttcca   3600
catagtttac ctttggcaga cttactgagc caggtccctg tggttaaaag gtacttagga   3660
ccctcagcca cttgttctga agccatagtt cactgggccc agatttgtaa gtagtacatg   3720
tttagttgct gatcatttta ataagaaggt ccatctgcgt agctccttca gcacagggt   3780 cctagtcccg cactagcact tggtaggtct gcaagtattt aatggcagag ttgtgtagac   3840
aatgtgtgtg gagaactcaa aggggtctgt gttctgggca gccagcagat aacatcctgc   3900
```

```
tgtctaaagg cgaaaaggcc cagcttccta aatgctcgtg cctatctgaa gccagcagag    3960
ttggtgggtt ttagcatctg cagagtactg aatcaaaaac agaaaattag aatgcgcctg    4020
tgagaactcc aggccggtaa catctgatac aaggggattt ctaaaattaa ggaactacta    4080
gtttaagaaa aatatatttt gcttttgtag tccatgcctt atagggagga ggacatgaat    4140
tactgcgtat ttcacaaagg agaacacaaa caatgtccct taagtttgtc tttgaaagga    4200
aggaagctag ccaaagctga cactgaagcc agtaatcttg cagaacttga tttttacaag    4260
atgatagaaa tttgtatccg catatgtgac tgtatatttc ttgagcaagt aatagctgga    4320
gaatatgtct tctgtgacca accccgaaat acagagtcca aatgaatgtt aggctgtggg    4380
gaggtgggtt tcagtgctgg agactctcct gagtgggctc tagtgaatga cagctcagcc    4440
tgtgtggagc acggtacttt ctaaaattac ttaggtttgt ttgttgtttt cagggtgggg    4500
gatcagtgag ggtaagacag gacttgttat gtagtccaag caggccttga accctacctg    4560
cctcagcctc gaaagagctg ggattaccat gccagcttg aaattccttt ttaagcctgg     4620
gaaaaatggg tagtatccac tgcgcttcct tcctggtaga gccatgccat agaaagtcag    4680
tttagtgggc tgaagggggt ttgtgtgctt tggaaagcag ttgtgatttg ttgagcaact    4740
ggtaagctct gcagcaaggg ttggcttttcc tggcaattga ttctttctca ttctgtgaaa    4800
aacctttcaa gtgtcaagtt agtatttata aaaacaaaaa ttgttttttg ctggccacat    4860
tttaagtatc cttataagaa ttagaagaac gtctataacc aaattttccc atctccctcc    4920
acctctgatt atttatgcta caatatatac tatccgactt ctgaattatg ttgtttattc    4980
tctcatttgt tcttgatttc cccagggaat gaaagctact ggttgactta aaaacacctg    5040
ggctttacaa atttgaaggc a                                              5061

<210> SEQ ID NO 20
<211> LENGTH: 2809
<212> TYPE: DNA
<213> ORGANISM: Mus musculus Mig-6

<400> SEQUENCE: 20
taggatcaca taacctgggc atggtagtac atgcccataa gcccagcact tgggaggcag      60
aggctggaga atcaggagtt caaggtcatc tttggttaca catgcattcg gggttttagg     120
ccacatgaat ccctgtgaaa gaagaggggg ggtggggga aggaaaggaa aggaaaggaa      180
aggaaaggaa gaaaggagag aaattttgtg gtaaaatcaa gccttttgtt cttacctgca     240
acaactaagt aaccttggtc ccgtgcttct gtggaaacct tgagggtcag ggctgtgcag     300
tccgtagaaa ggagcattca ctgtacagat ttcttgggct tcaggattac tctgggccct     360
ttgtggcctt tgctgctgtt tgtctggac cttactctcc actgccaggc atcacagagg       420
gccctgcaca ctgctgtctg ctgggctgct gtatcagagc tggtggccct gtgtgtcggg     480
tgttagattt gggaagaaga gagtttgtgg cgatgtgatt tggaagtgtt taaaaggtac     540
tcggtaggca actgaagggc atctgacccc tggaaatgat ggtcagagtt ggagatagcg     600
atttggaagg tgtgatagca gacgaaggca agcctgtgag gccaggaagc aggaagcagc     660
tgggcacgtt ccagaagctg aaggccacgg gcgagtaggc tgagcagtgg aaaagggcag     720
tgggtgcaac tcaaagatc ctaagtggga aggaacacg atgtgatttg ttttaggaaa       780
gatgacagta gctgctgtgt ggggaacatt tcagagaagt gaaattagca gaaacactaa     840
aagctacagg ccagggccca aaactggcac cagagtgaag ggggggcggg ggagggggatg    900 gagagacaca tggctttcag agttgttagg atgacaggct ccagcctgaa agcagtctgc     960
```

```
accgcccttc ttccagaacg gcggtggctc ttgcgagctg gaaccgcctg tgtccttgta    1020
ctagcactga gcattgcctg gtacaggaag ccatggtact tacattagtt ccagcttcat    1080
ttccttacct gtttctgtgt tttcccttga acttttgcga tatactttc atggttttt     1140
ctggtcaaag aactgtcctt ggcgcccatg ctaatggcac actgctaaaa cacccaggag    1200
ccacttgccc acctatacct ccccagccgg cacaccaagc aagttgaatt ttttttttcc    1260
aacttatatg tctgggagtt ttgcctgtgt atgtctgtgc attgcatgca tgcagtacct    1320
ggtgcccaca ggcccaaaga tggcgtggga tcatggtttc tgacagccat gagctgctac    1380
atggatgctg ggaactgaac tctggttctc aggcagagca gccagtattc ttaacgacta    1440
agccatcttt acagccctgt gtgatatctt aggtaattat caaaatggga agttggtatc    1500
tgcacgatcc ttgtataatg ttttgtttag ctgcaaactg atacttggtc ataaaaacta    1560
gaaactgatt tggccattct gtcaggcatt ttgtaaaaag ctagtggaac ttttaaaaag    1620
ctgtcgtgca aagccatgca gtgctcatgg cacttgatga gatggtcctg atgctggctg    1680
gctccagagt agtctccgct cttggcatag ctggaggctt gaggttccat acctgaaatg    1740
agaaaaagcc caaagacaag aatgtacatt ttgaattgag ctctaaagct ctgaggtatt    1800
cttgccctaa tataagattt cttcaaacta gaaatggctt gaggacttgt tttctttgta    1860
gtgtaggtca tttgacagaa tgttctggcg ccttttgcgcc cttcggtgtg agtcatgcca   1920
ttcttttgag gctctgaggg gtgaagggga agagaacaga atttgtctac actgttggcc    1980
tcacctcttg ctccctgtaa ctacacaaac atggttcagg cgtgcctagc gctgcttact    2040
gtgagggtgt gagcttgctc gccttcgtct cacctgtatg gattcaactt caggatactt    2100
gtatccgagc cacggggagt ctgcggctcc cgcacgttta acaagctccc cttagctttt   2160
caagatgtct acttggaatc tgaagcagca aacatacttg tgtatgtttt tctgtacctg    2220
agcttacatc agagcaacct tgtgactcag aagtcaccgc cccatggcag tagtgggggtt   2280
ttggtaagga gtgggggggct ggggacagat gggaaggaat gtacttcaag tactagttgg   2340
cacctgtctt ggagctgctg tcaggctaga ggcttagcca gcgtgcctct tgaatgctgt    2400
catctctcac cctgtaagtt cagacacccg gaaccccaag cacaaaagcc tgtagcaatt    2460
acccacaggg atccgcgtat ctgccccccc tcccccaaaa tggagctgct taggaatgtg    2520
cactgcattc tcttcacaga tccaggcagc accttcattc cttagtaaac atctaaaccc    2580
aggcctccca tgggtttctt cacagtcatg agggttagcc agtgccttcc ctagggacag    2640
catgacttgt ccgctcccct cttgtgaaag gcagaatgag tcgtgtcatt ctggcctgca    2700
ccaagccttc ctctggccta gccatggcac cgcctcaggc acagcacaca ggaagctgta    2760
ctttgttatt ctgaattcct ggctagcctc atgttcttgg atgaaccag                2809
```

```
<210> SEQ ID NO 21
<211> LENGTH: 651
<212> TYPE: DNA
<213> ORGANISM: Artificial Sequence
<220> FEATURE:
<223> OTHER INFORMATION: probe

<400> SEQUENCE: 21
tacctgcctt attcagagga gtcaagtgtg tatcttaagt catttgttc cagtaatttg      60
aagagcctaa gactttaaaa gagaggctgt ggtatggtcg agagcataaa ctttgaggcc    120
aagcttcctg aagtaagccg tggcattact gtggctcacc ggagccgagt cagatctagt   180
tgcagaagct cctcgtctgt cattgagagt agtgtcccac ctaccttagg gctgctacaa    240
```

```
ggataaaact gaaaaccttc ctgacagaca gtatcctatg aatgtcatta tcatcaccta      300
tgtattaatt ttaactctcc tgagttgtcc attgggttat ttaaatgctt gttaaataaa      360
cttgaagttt taaagactca tttcccatca ttagcccatt gtggtcattg tcattaagat      420
tacaacagaa tccacacatc gttcacaggt acagtgcatt gcatatgtcg gaaagaaatg      480
ctcttccatg ccgtgtgtgc ttgcctgtgt ctgtggatgg tactgttgat tgttgtgctc      540
tgtaggaaaa ataccaatga caaaacaata cagtgctgtt gccctgcttg taattgtatc      600
tccctaaaat cctgagggac aaactgaatc acaaggctat tgagacagga g               651

<210> SEQ ID NO 22
<211> LENGTH: 14
<212> TYPE: PRT
<213> ORGANISM: Mus musculus Mig-6

<400> SEQUENCE: 22

Ser His Gly Lys Arg Lys His Leu Ser Tyr Val Val Ser Pro
1               5                   10
```